United States Patent
Ueng et al.

(10) Patent No.: US 10,597,378 B2
(45) Date of Patent: Mar. 24, 2020

(54) TETRAHYDROISOQUINOLINES FOR USE AS MOR/NOP DUAL AGONISTS

(71) Applicant: National Health Research Institutes, Miaoli County (TW)

(72) Inventors: Shau-Hua Ueng, Miaoli County (TW); Shiu-Hwa Yeh, Miaoli County (TW); Po-Kuan Chao, Miaoli County (TW); Chuan Shih, Carmel, IN (US)

(73) Assignee: National Health Research Institutes, Zhunan Town (TW)

( * ) Notice: Subject to any disclaimer, the term of this patent is extended or adjusted under 35 U.S.C. 154(b) by 0 days.

(21) Appl. No.: 15/699,123

(22) Filed: Sep. 8, 2017

(65) Prior Publication Data

US 2019/0077786 A1 Mar. 14, 2019

(51) Int. Cl.
| | |
|---|---|
| C07D 217/22 | (2006.01) |
| C07D 401/12 | (2006.01) |
| C07D 413/12 | (2006.01) |
| A61P 25/04 | (2006.01) |
| A61P 25/36 | (2006.01) |
| C07D 209/48 | (2006.01) |
| C07D 401/06 | (2006.01) |
| C07D 217/14 | (2006.01) |

(52) U.S. Cl.
CPC ......... *C07D 401/12* (2013.01); *C07D 209/48* (2013.01); *C07D 217/14* (2013.01); *C07D 217/22* (2013.01); *C07D 401/06* (2013.01)

(58) Field of Classification Search
CPC .................................................. C07D 217/22
See application file for complete search history.

(56) References Cited

U.S. PATENT DOCUMENTS

| | | | | |
|---|---|---|---|---|
| 4,113,867 | A | * | 9/1978 | Seubert ................ C07D 217/14 514/225.8 |
| 2005/0234044 | A1 | | 10/2005 | Groneberg et al. |
| 2007/0203118 | A1 | | 8/2007 | Hofmeister et al. |
| 2010/0196357 | A1 | * | 8/2010 | Huang ................ C07D 221/18 424/130.1 |
| 2014/0370556 | A1 | * | 12/2014 | Qian .................... C07D 471/04 435/119 |

FOREIGN PATENT DOCUMENTS

| | | |
|---|---|---|
| CN | 103160562 A | 6/2013 |
| TW | 200612940 A | 5/2006 |
| WO | WO 00/18233 | 4/2000 |
| WO | WO 02/089806 | 11/2002 |
| WO | WO-2016/078765 A1 | 5/2016 |

OTHER PUBLICATIONS

CA Registry No. 1171183-85-9, entered into the Registry File on Jul. 31, 2009, supplied by Ambinter.*
About Ambinter, 2 page retrieved from the Internet on Aug. 30, 2018 at http://www.ambinter.com/about-us.*
CA Registry No. 623909-58-0, entered into the Registry File on Dec. 5, 2003, supplied by Akos Consulting & Solutions.*
Akos Consulting & Solutions GmbH company info, 2 pages retrieved from the Internet on Aug. 30, 2018 at http://www.akosgmbh.de/akosgmbh.html.*
CA Registry No. 2040062-92-6, entered into CA Registry File on Nov. 28, 2016, supplied by FCH Group. (Year: 2016).*
FCH Group Product Guide, 1 page, retrieved from the Internet at http://fchgroup.net/products.php on Apr. 5, 2014. (Year: 2014).*
CA Registry No. 2039189-25-6 and 2039189-26-7, entered into CA Registry File on Nov. 28, 2016, supplied by FCH Group. (Year: 2016).*
CA Registry No. 2038610-53-4 and 2038610-54-5, entered into CA Registry File on Nov. 27, 2016, supplied by FCH Group. (Year: 2016).*
CA Registry No. 2037560-35-1 and 2037560-36-2, entered into CA Registry File on Nov. 25, 2016, supplied by FCH Group. (Year: 2016).*
CA Registry No. 2035303-04-7 and 2035303-05-8, entered into CA Registry File on Nov. 21, 2016, supplied by FCH Group. (Year: 2016).*
CA Registry No. 2033743-08-5 and 2033743-09-6, entered into CA Registry File on Nov. 17, 2016, supplied by FCH Group. (Year: 2016) (Year: 2016).*
Chen et al "1. Discovery, Structure-Activity Relationship Studies, and Anti-Nociceptive Effects of N-(1,2,3,4-Tetrahydro-1-Isoquinolinylmethyl)Benzamides as Novel Opioid Receptor Agents", European Journal of Medicinal Chemistry vol. 126, pp. 202-217, 2017.
Coyle et al "Dibenzo[a,g]Quinolizin-8-Ones by Acid Treatment of the Photoproducts from N-(1,2,3,4-Tetrahydroisoquinolin-2-yl-Methyl) Aromatic Dicarboximides" Journal of Chemical Research Synopses vol. 11, p. 351, 1985.
Coyle et al "Photocyclization of N-(Dialkylaminoalkyl) Aromatic 1,2-Dicarboximides. X-Ray Molecular Structure of a Stereoisomer of 4-Benzyl-2-Hydroxy-3-Phenyl-4,6-Diazatricyclo[6.5.0.0$^{2,6}$]Dodeca-1(12),8,10-Trien-7-One" Journal of the Chemical Society Perkin Transactions 1 Organic and Bio-Organic Chemistry vol. 1, pp. 121-129, 1985.

(Continued)

*Primary Examiner* — Emily A Bernhardt
(74) *Attorney, Agent, or Firm* — Cesari and McKenna, LLP

(57) ABSTRACT

Disclosed are compounds of formula (I) below or pharmaceutically acceptable salts thereof:

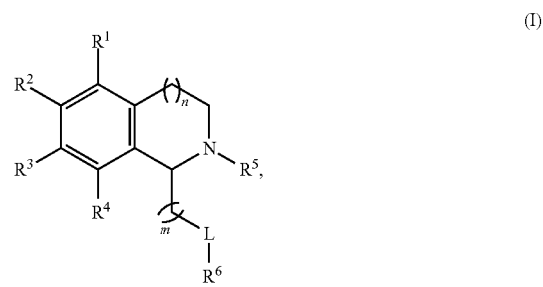

(I)

in which each of variables $R^1$-$R^6$, L, m, and n is defined herein. Also disclosed are a method for treating an opioid receptor-associated condition with a compound of formula (I) and a pharmaceutical composition containing same.

15 Claims, No Drawings

(56) References Cited

OTHER PUBLICATIONS

Guo et al. "Synthesis and Biological Evaluation of 1,2,3,4-Tetrahydroisoquinolines Derivatives as Monoamine Oxidase Inhibitors for Treatment of Alzheimer's and Parkinson's Diseases", Asian Journal of Chemistry, 2015, vol. 27, No. 10, pp. 3651-3654.
Rupe et al. "Catalytic reduction of 1-cyano-2-benzoyl-1,2-dihydroisoquinoline (Reissert's isoquinoline compound)", Helvetica Chimica Acta, 1939, vol. 22, pp. 673-683.

* cited by examiner

TETRAHYDROISOQUINOLINES FOR USE AS MOR/NOP DUAL AGONISTS

BACKGROUND

Opioids are classified into natural opioids (e.g., morphine), semi-synthetic opioids (e.g., heroin), synthetic opioids (e.g., methadone), and endogenous opioids (e.g., endorphins). See, e.g., Piestrzeniewicz et al., Postepy Biochem, 2006, 52:313-319.

They act in both central and peripheral nervous systems to produce various pharmacological effects including, among others, analgesia and decreased gastrointestinal motility. Opioids have long been used as the most effective analgesics for treating acute pain (e.g., post-operative pain) and chronic pain (e.g., cancer pain). See, e.g., Waldhoer et al., Annu Rev Biochem, 2004, 73:953-990.

Opioids primarily activate three classic subtypes of opioid receptors, namely, mu-opioid receptor (MOR), delta-opioid receptor (DOR), and kappa-opioid receptor (KOR). Various heterocyclic compounds have been used as nonselective or selective MOR agonists for treating an opioid receptor-associated condition, e.g., pain, immune function, esophageal reflux, and cough. Yet, conventional heterocyclic compounds typically produce adverse effects, such as respiratory depression. Moreover, long-term use of these compounds for controlling chronic pain develops severe side effects such as tolerance, dependence, and addiction. See, e.g., Tao et al., J Pharmacol Exp Ther, 2002, 303:549-556.

There is a need to develop new MOR modulators that have fewer and/or less deterious side effects for therapeutic use.

SUMMARY

The present invention relates to certain heterocyclic compounds as opioid receptor modulators for treating an opioid receptor-associated condition. Unexpectedly, these compounds, acting as mu-opioid receptor/nociceptin receptor (MOR/NOP) dual agonists, produce anti-nociceptive effects without developing severe side effects.

An aspect of this invention is drawn to the compounds of formula (I) below or pharmaceutically acceptable salts thereof:

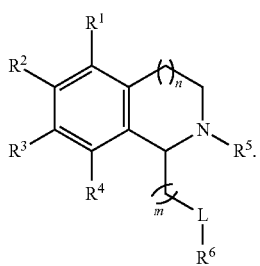

(I)

In this formula, each of $R^1$-$R^4$, independently, is H, halo, OH, CN, $CF_3$, $NH_2$, $NO_2$, $SO_2$, COOH, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, $C_{6-14}$ aryl, $C_{1-13}$ heteroaryl, —C(O)OR, —C(O)NRR', —NRC(O)R', —S(O)$_2$R, —S(O)$_2$NRR', —NRS(O)$_2$R', —C(O)R, —C(O)NRS(O)$_2$R', —C(O)NRS(O)$_2$NR'R", or —NRS(O)$_2$NR'R"; $R^5$ is H, OH, $C_{1-6}$ alkyl, $C_{1-6}$ haloalkyl, $C_{3-8}$ cycloalkyl, $C_{2-8}$ heterocycloalkyl, $C_{6-14}$ aryl, $C_{1-13}$heteroaryl, —C(O)OR, —C(O)NRR', —S(O)$_2$R, —S(O)$_2$NRR', or —C(O)R; $R^6$ is $C_{1-6}$ alkyl, $C_{3-8}$ cycloalkyl, $C_{2-8}$ heterocycloalkyl, $C_{6-14}$ aryl, or $C_{1-13}$ heteroaryl; L is O, S, NR, —CRR'—, —C(O)—, —NRC(O)—, or —C(O)NR—; m is 1 or 2; and n is 0 or 1, each of R, R', and R", independently, being H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, $C_{6-14}$ aryl, or $C_{1-13}$ heteroaryl.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "haloalkyl" refers to alkyl substituted with one or more halogen (chloro, fluoro, bromo, or idodo) atoms. Examples include trifluoromethyl, bromomethyl, and 4,4,4-trifluorobutyl. The term "alkenyl" refers to a straight or branched hydrocarbon group, containing 2-20 (e.g., 2-10 and 2-6) carbon atoms and one or more double bonds. Examples include ethylenyl, propenyl, and butenyl.

The term "cycloalkyl" refers to a saturated and partially unsaturated monocyclic, bicyclic, tricyclic, or tetracyclic hydrocarbon group having 3 to 12 carbons. Examples include cyclopropyl, cyclobutyl, cyclopentyl, cyclopentenyl, cyclohexyl, cyclohexenyl, cycloheptyl, and cyclooctyl. The term "heterocycloalkyl" refers to a nonaromatic 5-8 membered monocyclic, 8-12 membered bicyclic, or 11-14 membered tricyclic ring system having one or more heteroatoms (e.g., 0, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "alkoxy" refers to an —O-alkyl group. Examples include methoxy, ethoxy, propoxy, and isopropoxy. The term "haloalkoxy" refers to alkoxy substituted with one or more halogen atoms. Examples include —O—$CH_2Cl$ and —O—$CHClCH_2Cl$.

The term "halo" refers to a fluoro, chloro, bromo, or iodo radical. The term "amino" refers to a radical derived from amine, which is unsunstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

The term "aralkyl" refers to alkyl substituted with an aryl group. Examples include benzyl and naphthylmethyl. The term "heteroaralkyl" refers to an alkyl group substituted with a heteroaryl group. Examples include pyridylmethyl and furylmethyl.

The term "aryl" refers to a 6-carbon monocyclic, 10-carbon bicyclic, 14-carbon tricyclic aromatic ring system. Examples of aryl groups include phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (e.g., 0, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

Alkyl, alkenyl, cycloalkyl, heterocycloalkyl, aralkyl, heteroaralkyl, alkoxy, aryl, and heteroaryl mentioned herein include both substituted and unsubstituted moieties. Possible substituents on cycloalkyl, heterocycloalkyl, aralkyl, heteroaralkyl, alkoxy, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl or alkenyl include all of the above-recited substituents except $C_1$-$C_{10}$ alkyl. Cycloalkyl, heterocycloalkyl, aryl, and heteroaryl can also be fused with each other.

In addition to the compounds of formula (I) described above, their pharmaceutically acceptable salts and solvates, where applicable, are also covered by this invention. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Another aspect of this invention is a pharmaceutical composition for treating an opioid receptor-associated condition.

The pharmaceutical composition contains one of the compounds of formula (I) described above or its pharmaceutically acceptable salt and a pharmaceutically acceptable carrier.

This invention also covers use of such a composition for the manufacture of a medicament for treating an opioid receptor-associated condition.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of the present invention is a method of treating an opioid receptor-associated condition.

The method includes administering to a subject in need thereof an effective amount of a compound of formula (I) or a pharmaceutically acceptable salt thereof.

The above-described compounds or a pharmaceutical composition containing one or more of them can be administered to a subject orally, parenterally, by inhalation spray, topically, rectally, nasally, buccally, vaginally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the invention are set forth in the description below. Other features, objects, and advantages of the invention will be apparent from the description and from the claims.

DETAILED DESCRIPTION

First disclosed in detail herein are the compounds of formula (I) below or pharmaceutically acceptable salts thereof:

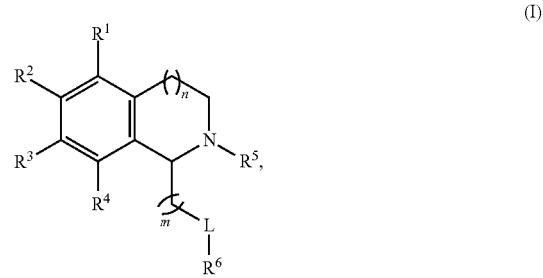

in which each of variables $R^1$-$R^6$, L, m, and n is defined as in the SUMMARY section.

Typically, each of $R^1$-$R^4$, independently, is H, halo, OH, $CF_3$, $C_{1-6}$ alkyl, $C_{3-8}$ cycloalkyl, or $C_{1-6}$ alkoxy; and $R^5$ is H, $C_{1-6}$ alkyl, $C_{1-6}$ haloalkyl, or —S(O)$_2$R. For example, each of $R^1$-$R^4$ is H and $R^5$ is H or $C_{1-6}$ alkyl.

$R^6$ can be $C_{3-8}$ cycloalkyl, $C_{2-8}$ heterocycloalkyl, or $C_{6-14}$ aryl. Examples of $R^6$ include, but are not limited to,

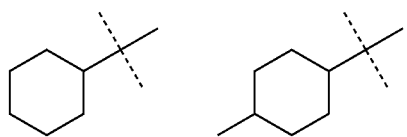

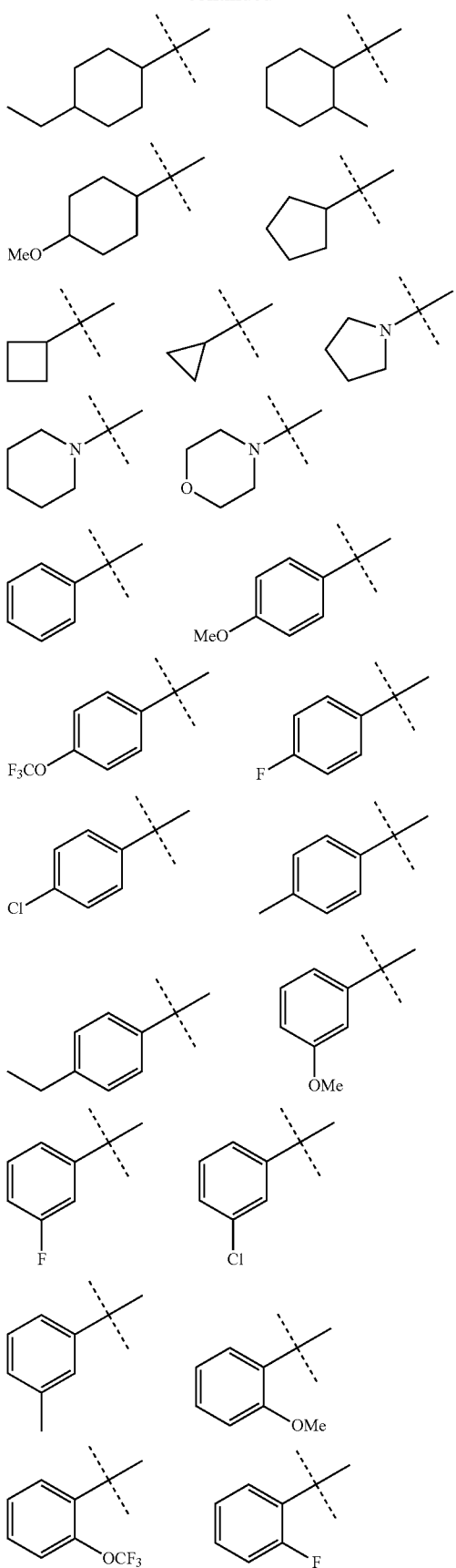
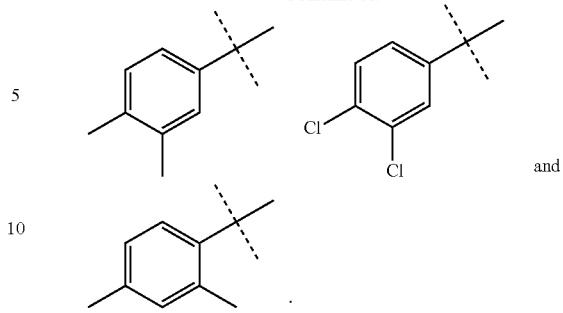

Turning to variables L, m, and n, it is preferred that L is —NRC(O)—, e.g., —NHC(O)—, and each of m and n is 1.

In exemplary compounds, each of $R^1$-$R^4$, independently, is H, halo, OH, $CF_3$, $C_{1-6}$ alkyl, $C_{3-8}$ cycloalkyl, or $C_{1-6}$ alkoxy; $R^5$ is H, $C_{1-6}$ alkyl, $C_{1-6}$ haloalkyl, or —$S(O)_2R$; $R^6$ is $C_{3-8}$ cycloalkyl, $C_{2-8}$ heterocycloalkyl, or $C_{6-14}$ aryl; L is —NHC(O)—; and each of m and n is 1. Preferably, each of $R^1$-$R^4$ is H, $R^5$ is H or $C_{1-6}$ alkyl, and $R^6$ is one of the following moieties:

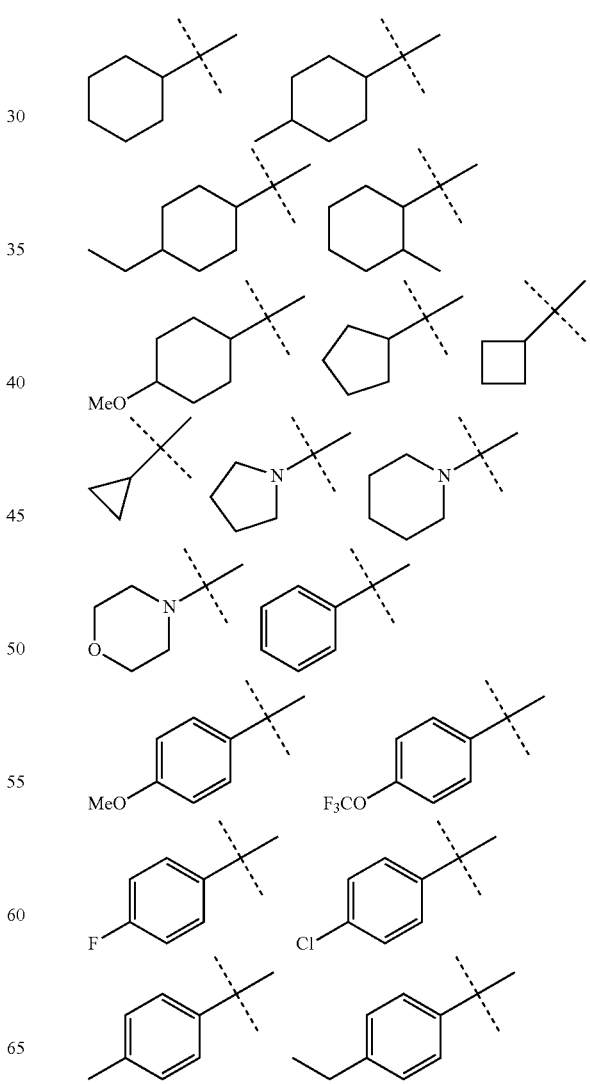

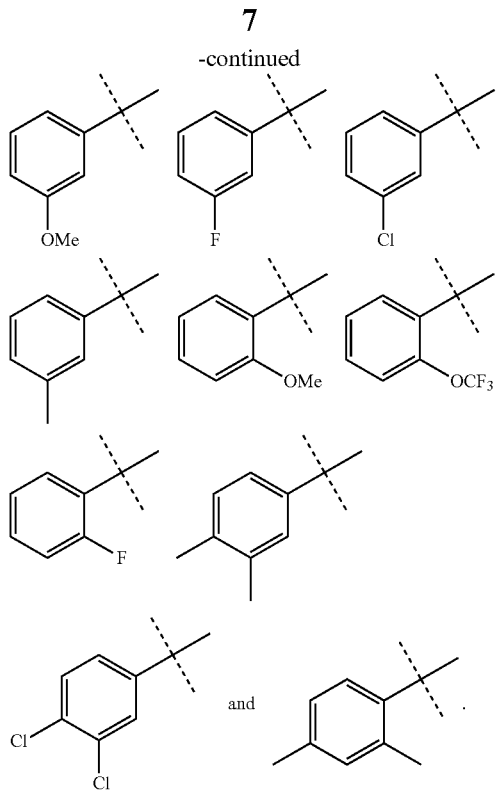

In one embodiment, referring to formula (I), the carbon attached to both the phenyl ring and the nitrogen atom has a stereoisomeric configuration of R or S, and the compound has an enantiomeric excess of 90% or higher (e.g., ≥95% and ≥99%).

This embodiment includes compounds having each of $R^1$-$R^4$, independently, as H, halo, OH, $CF_3$, $C_{1-6}$ alkyl, $C_{3-8}$ cycloalkyl, or $C_{1-6}$ alkoxy; $R^5$ as H, $C_{1-6}$ alkyl, $C_{1-6}$ haloalkyl, or —S(O)$_2$R; $R^6$ as $C_{3-8}$ cycloalkyl, $C_{2-8}$ heterocycloalkyl, or $C_{6-14}$ aryl; and L as —NRC(O)—. Preferably, these compounds have each of $R^1$-$R^4$ being H, $R^5$ being H or $C_{1-6}$ alkyl, and $R^6$ being $C_6$ aryl, in which the $C_6$ aryl is optionally mono-, di-, or tri-substituted with halo, OH, CN, $CF_3$, $NH_2$, $NO_2$, $SO_2$, COOH, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, $C_{6-14}$ aryl, $C_{1-13}$ heteroaryl, —C(O)OR, —C(O)NRR', —NRC(O)R', —S(O)$_2$R, —S(O)$_2$NRR', —NRS(O)$_2$R', or —C(O)R; or is optionally fused with $C_{3-8}$ cycloalkyl, $C_{2-8}$ heterocycloalkyl, $C_{6-14}$ aryl, or $C_{1-13}$ heteroaryl. More preferably, they have $R^6$ being one of the following moieties:

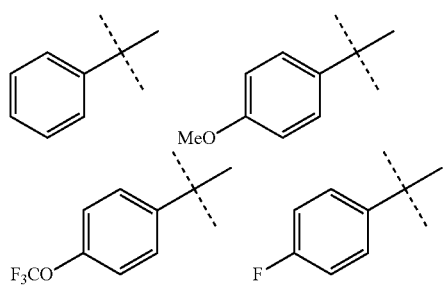

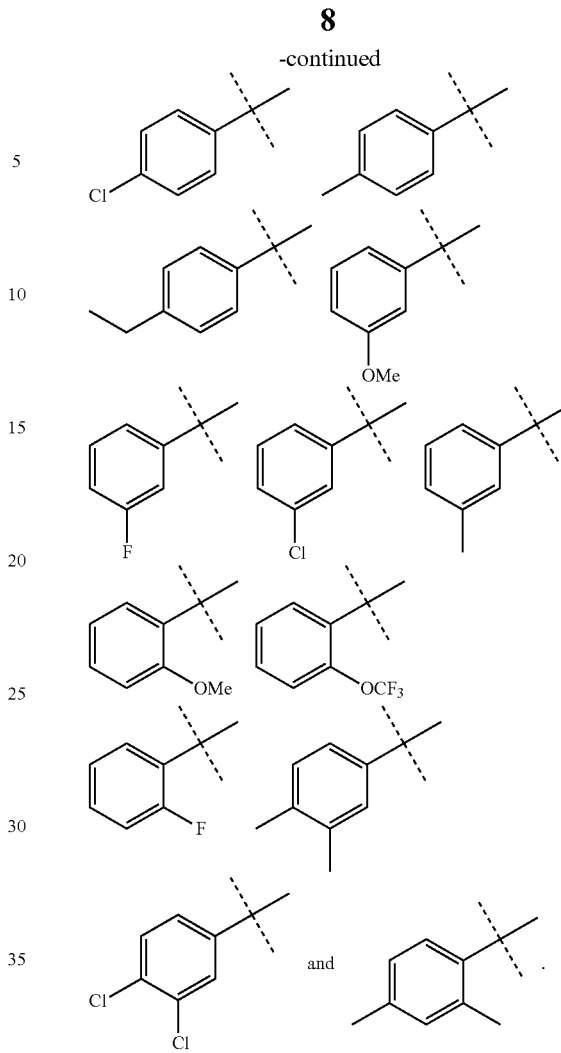

Most preferably, these compounds have L being —NHC(O)— and each of m and n being 1.

Also within this invention is a pharmaceutical composition for treating an opioid receptor-associated condition, e.g., pain, the composition containing one of the compounds of formula (I) set forth above or a pharmaceutically acceptable salt thereof and a pharmaceutically acceptable carrier.

Further covered by this invention is a method for treating an opioid receptor-associated condition, the method including administering to a subject in need thereof an effective amount of a compound of formula (I) or a pharmaceutically acceptable salt thereof.

Examples of the opioid receptor-associated condition include, but are not limited to, pain, immune disease, esophageal reflux, diarrhea, anxiety, and heroin addiction. In particular, the method is performed for treating pain, i.e., opioid receptor-associated pain. The pain can be cancer pain, post-operative pain, renal colic pain, acute pancreatitis pain, angina pain, low back pain, rheumatoid arthritis pain, osteoarthritis pain, neuropathic pain, fibromyalgia pain, or complex regional pain syndrome.

It should be pointed out that in this method the compound of formula (I) exerts anti-nociceptive effects without developing severe side effects via a dual mechanism, i.e., working as a mu-opioid receptor/nociceptin receptor (MOR/NOP) dual agonist. NOP has similar sequence homology to classical opioid receptors. It has been reported that NOP agonists produce antinociception with fewer side effects, such as abuse, respiratory depression, and gastrointestinal inhibition. See, e.g., Lin et al., ACS Chemical Neuroscience, 2013, 4:214-224. A MOR/NOP dual agonist, e.g., a compound of formula (I), can be used for treating an opioid receptor-associated condition, e.g., pain, while producing fewer side effects than conventional MOR modulators.

Referring back to formula (I), the compound used in the above-described method typically has each of $R^1$-$R^4$, independently, being H, halo, OH, $CF_3$, $C_{1-6}$ alkyl, $C_{3-8}$ cycloalkyl, or $C_{1-6}$ alkoxy; $R^5$ being H, $C_1$ alkyl, $C_{1-6}$ haloalkyl, or —$S(O)_2R$; $R^6$ being $C_{3-8}$ cycloalkyl, $C_{2-8}$ heterocycloalkyl, or $C_{6-14}$ aryl; and L being —NRC(O)—.

Methods for synthesizing the compounds of formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); P. Roszkowski, J. K. Maurin, Z. Czarnocki "Enantioselective synthesis of (R)-(−)-praziquantel (PZQ)" Tetrahedron: Asymmetry 17 (2006) 1415-1419; and L. Hu, S. Magesh, L. Chen, T. Lewis, B. Munoz, L. Wang "Direct inhibitors of keap1-nrf2 interaction as antioxidant inflammation modulators," WO2013/067036.

The compounds of formula (I) thus prepared can be initially screened using in vitro assays, e.g., the FLIPR® calcium assay described in Example 68 below, for their potency in activating MOR in cells. They can be subsequently evaluated using in vivo assays, e.g., a tail-flick test assay also described in Example 68. The selected compounds can be further tested to verify their efficacy in disease related pain and adverse effects models. Based on the results, an appropriate dosage range and administration route can be determined.

In an exemplary in vitro assay for identifying MOR agonists, cells that express a MOR are treated with a test compound in a cellular calcium fluorescent assay and calcium fluorescence intensity is then measured to determine whether the MOR is activated. A test compound is identified as a MOR agonist if the MOR is activated.

Two parameters, i.e., $EC_{50}$ and AUC, are typically used in the assay described above to measure the degree of MOR activation exerted by the test compound. $EC_{50}$ herein refers to the concentration of a compound that induces a response halfway between the baseline and the maximum after a specified exposure time. AUC refers to the area under the response curve, an indication of the compound's capability of activating a MOR.

In an exemplary in vivo assay for confirming that a test compound is a MOR agonist, a test compound is injected into a mouse pain model (e.g., via intravenous administration), basal latencies are recorded before the treatment and test latencies are recorded at various specified times after the injection, and a time-response curve is recorded and AUC values are calculated to determine whether an analgesic effect is exerted on the mouse. The test compound is confirmed to be a MOR agonist upon observation of an analgesic effect.

In an exemplary in vitro assay for identifying NOP agonists, cells are engineered to overexpress NOP and are designed to detect changes in intracellular cAMP levels in response to agonist stimulation of the receptor. The enzyme donor-cAMP complex complements with the acceptor and forms an active enzyme. The active enzyme subsequently hydrolyzes a substrate to produce a chemiluminescent signal that is directly proportional to the amount of cAMP in the cells. These cells have thus been modified to work in an agonist mode.

Without further elaboration, it is believed that one skilled in the art can, based on the above description, utilize the present invention to its fullest extent. The following specific examples, i.e., EXAMPLES 1-69, are therefore to be construed as merely illustrative, and not limitative of the remainder of the disclosure in any way whatsoever. All publications cited herein are incorporated by reference in their entirety.

Among the specific examples, EXAMPLES 1-67 set forth the procedures for preparing certain intermediates and 56 exemplary compounds of formula (I), as well as the analytical data for the compounds thus prepared; and EXAMPLES 68 and 69 set forth the protocols for testing these compounds.

Shown in the table below are the structures and names of 56 exemplary compounds of formula (I). All 56 compounds were found to activate a MOR to various degrees as indicated by their $EC_{50}$ and AUC values included in the following table.

| No. | Structure | Name | FLIPR $Ca^{2+}$ $EC_{50}$ (μM) | AUC |
|---|---|---|---|---|
| 5 | 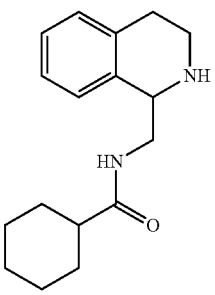 [SMILES: O=C(NCC1NCCc2ccccc21)C1CCCCC1] | N-(1,2,3,4-Tetrahydro-1-isoquinolinylmethyl) cyclohexanecarboxamide | 6.38 | 6142 |

-continued

| No. | Structure | Name | FLIPR Ca$^{2+}$ EC$_{50}$ (μM) | AUC |
|---|---|---|---|---|
| 6 | 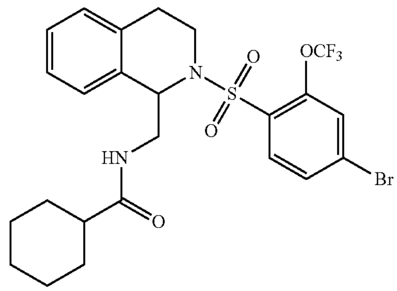 [SMILES: O=C(NCC1c2ccccc2CCN1S(=O)(=O)c1ccc(Br)cc1OC(F)(F)F)C1CCCCC1] | N-[(2-{[4-Bromo-2-(trifluoromethoxy)phenyl]sulfonyl}-1,2,3,4-tetrahydro-1-isoquinolinyl)methyl]cyclohexanecarboxamide | 1.12 | 15139 |
| 7 | 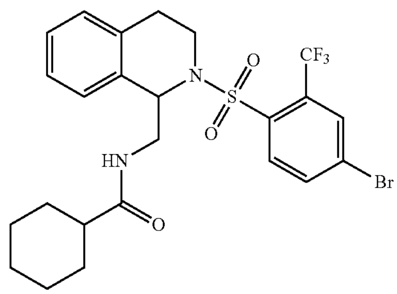 [SMILES: O=C(NCC1c2ccccc2CCN1S(=O)(=O)c1ccc(Br)cc1C(F)(F)F)C1CCCCC1] | N-[(2-{[4-Bromo-2-(trifluoromethyl)phenyl]sulfonyl}-1,2,3,4-tetrahydro-1-isoquinolinyl)methyl]cyclohexanecarboxamide | 2.56 | 7697 |
| 8 | 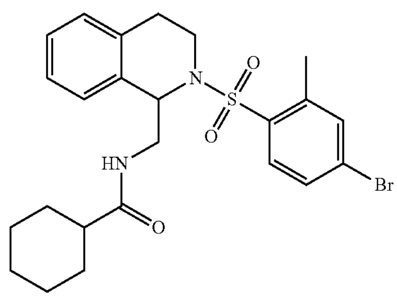 [SMILES: Cc1cc(Br)ccc1S(=O)(=O)N1CCc2ccccc2C1CNC(=O)C1CCCCC1] | N-({2-[(4-Bromo-2-methylphenyl)sulfonyl]-1,2,3,4-tetrahydro-1-isoquinolinyl}methyl)cyclohexanecarboxamide | 6.27 | 3757 |
| 9 | 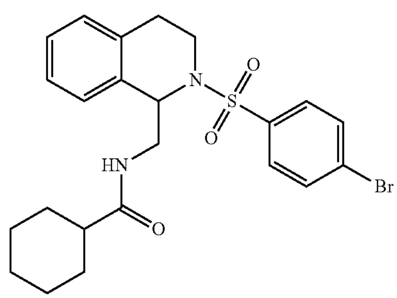 [SMILES: O=C(NCC1c2ccccc2CCN1S(=O)(=O)c1ccc(Br)cc1)C1CCCCC1] | N-({2-[(4-Bromophenyl)sulfonyl]-1,2,3,4-tetrahydro-1-isoquinolinyl}methyl)cyclohexanecarboxamide | 8.82 | 6103 |
| 10 | 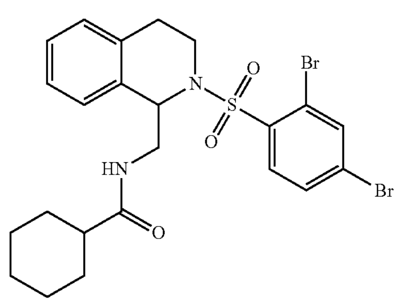 [SMILES: O=C(NCC1c2ccccc2CCN1S(=O)(=O)c1ccc(Br)cc1Br)C1CCCCC1] | N-({2-[(2,4-Dibromophenyl)sulfonyl]-1,2,3,4-tetrahydro-1-isoquinolinyl}methyl)cyclohexanecarboxamide | 3.31 | 7023 |

-continued

| No. | Structure | Name | FLIPR Ca$^{2+}$ EC$_{50}$ (μM) | AUC |
|---|---|---|---|---|
| 11 | 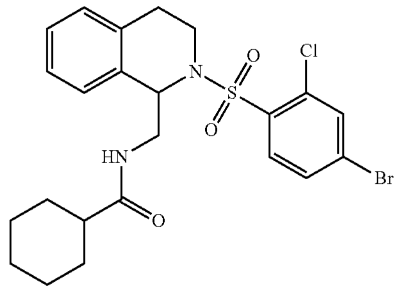 [SMILES: O=C(NCC1c2ccccc2CCN1S(=O)(=O)c1ccc(Br)cc1Cl)C1CCCCC1] | N-({2-[(4-Bromo-2-chlorophenyl)sulfonyl]-1,2,3,4-tetrahydro-1-isoquinolinyl}methyl)cyclohexanecarboxamide | 5.61 | 7597 |
| 12 | 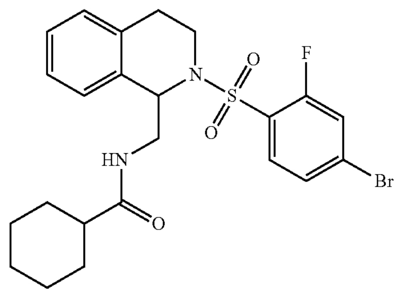 [SMILES: O=C(NCC1c2ccccc2CCN1S(=O)(=O)c1ccc(Br)cc1F)C1CCCCC1] | N-({2-[(4-Bromo-2-fluorophenyl)sulfonyl]-1,2,3,4-tetrahydro-1-isoquinolinyl}methyl)cyclohexanecarboxamide | 9.61 | 7271 |
| 13 | 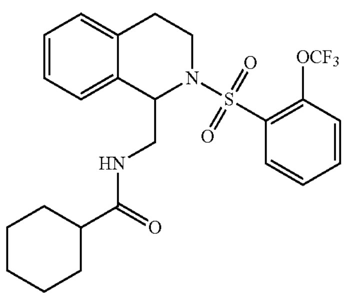 [SMILES: O=C(NCC1c2ccccc2CCN1S(=O)(=O)c1ccccc1OC(F)(F)F)C1CCCCC1] | N-[(2-{[2-(Trifluoromethoxy)phenyl]sulfonyl}-1,2,3,4-tetrahydro-1-isoquinolinyl)methyl]cyclohexanecarboxamide | 3.31 | 5152 |
| 14 | 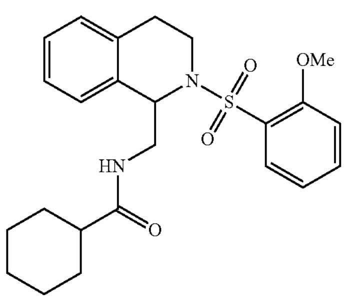 [SMILES: COc1ccccc1S(=O)(=O)N1CCc2ccccc2C1CNC(=O)C1CCCCC1] | N-({2-[(2-Methoxyphenyl)sulfonyl]-1,2,3,4-tetrahydro-1-isoquinolinyl}methyl)cyclohexanecarboxamide | 22.5 | 3327 |
| 15 | 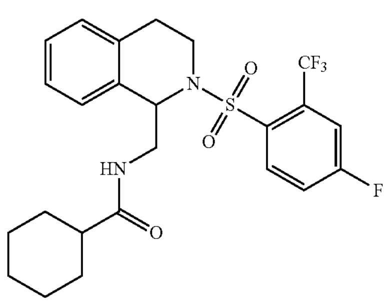 [SMILES: O=C(NCC1c2ccccc2CCN1S(=O)(=O)c1ccc(F)cc1C(F)(F)F)C1CCCCC1] | N-[(2-{[4-Fluoro-2-(trifluoromethyl)phenyl]sulfonyl}-1,2,3,4-tetrahydro-1-isoquinolinyl)methyl]cyclohexanecarboxamide | 5.88 | 5153 |

-continued

| No. | Structure | Name | FLIPR Ca²⁺ EC$_{50}$ (μM) | AUC |
|---|---|---|---|---|
| 16 | 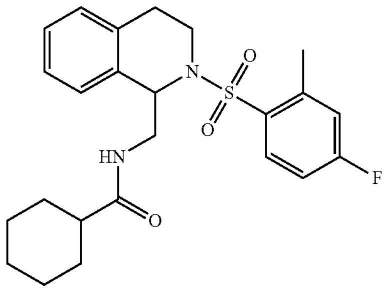 [SMILES: Cc1cc(F)ccc1S(=O)(=O)N1CCc2ccccc2C1CNC(=O)C1CCCCC1] | N-({2-[(4-Fluoro-2-methylphenyl)sulfonyl]-1,2,3,4-tetrahydro-1-isoquinolinyl}methyl)cyclohexanecarboxamide | 10.0 | 6213 |
| 17 | 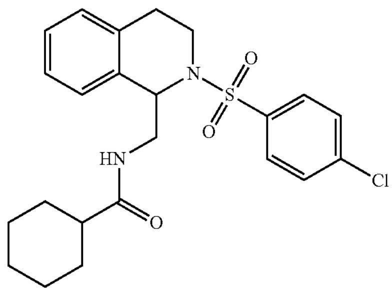 [SMILES: O=C(NCC1c2ccccc2CCN1S(=O)(=O)c1ccc(Cl)cc1)C1CCCCC1] | N-({2-[(4-Chlorophenyl)sulfonyl]-1,2,3,4-tetrahydro-1-isoquinolinyl}methyl)cyclohexanecarboxamide | 5.97 | 6144 |
| 18 | 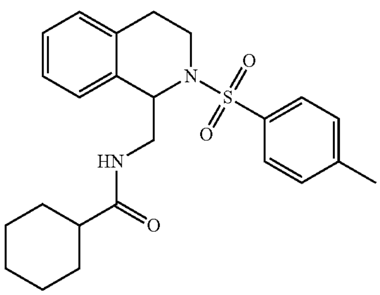 [SMILES: Cc1ccc(S(=O)(=O)N2CCc3ccccc3C2CNC(=O)C2CCCCC2)cc1] | N-({2-[(4-Methylphenyl)sulfonyl]-1,2,3,4-tetrahydro-1-isoquinolinyl}methyl)cyclohexanecarboxamide | 6.44 | 6808 |
| 19 | 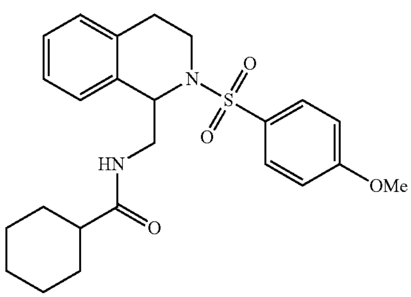 [SMILES: COc1ccc(S(=O)(=O)N2CCc3ccccc3C2CNC(=O)C2CCCCC2)cc1] | N-({2-[(4-Methoxyphenyl)sulfonyl]-1,2,3,4-tetrahydro-1-isoquinolinyl}methyl)cyclohexanecarboxamide | 7.84 | 3418 |
| 20 | 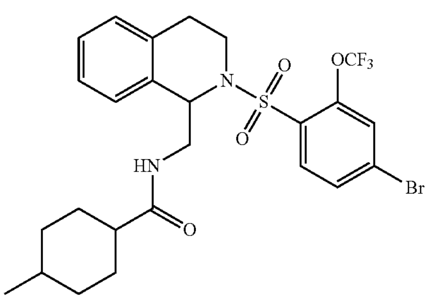 [SMILES: CC1CCC(C(=O)NCC2c3ccccc3CCN2S(=O)(=O)c2ccc(Br)cc2OC(F)(F)F)CC1] | N-[(2-{[4-Bromo-2-(trifluoromethoxy)phenyl]sulfonyl}-1,2,3,4-tetrahydro-1-isoquinolinyl)methyl]-4-methylcyclohexanecarboxamide | 0.97 | 9180 |

-continued

| No. | Structure | Name | FLIPR Ca$^{2+}$ EC$_{50}$ (μM) | AUC |
|---|---|---|---|---|
| 21 | 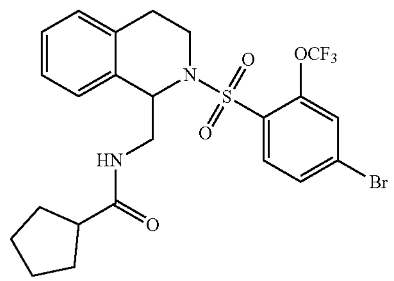 [SMILES: O=C(NCC1c2ccccc2CCN1S(=O)(=O)c1ccc(Br)cc1OC(F)(F)F)C1CCCC1] | N-[(2-{[4-Bromo-2-(trifluoromethoxy)phenyl]sulfonyl}-1,2,3,4-tetrahydro-1-isoquinolinyl)methyl]cyclopentanecarboxamide | 0.81 | 14615 |
| 24 | 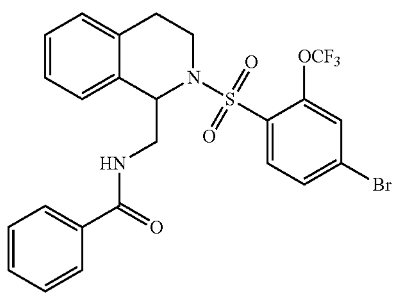 [SMILES: O=C(NCC1c2ccccc2CCN1S(=O)(=O)c1ccc(Br)cc1OC(F)(F)F)c1ccccc1] | N-[(2-{[4-Bromo-2-(trifluoromethoxy)phenyl]sulfonyl}-1,2,3,4-tetrahydro-1-isoquinolinyl)methyl]benzamide | 5.62 | 9294 |
| 25 | 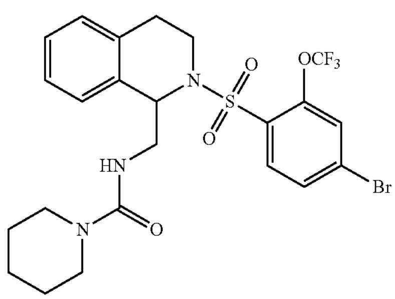 [SMILES: O=C(NCC1c2ccccc2CCN1S(=O)(=O)c1ccc(Br)cc1OC(F)(F)F)N1CCCCC1] | N-[(2-{[4-Bromo-2-(trifluoromethoxy)phenyl]sulfonyl}-1,2,3,4-tetrahydro-1-isoquinolinyl)methyl]-1-piperidinecarboxamide | 2.77 | 10498 |
| 26 | 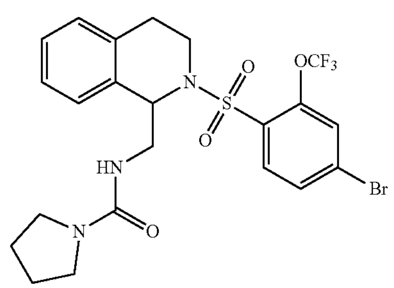 [SMILES: O=C(NCC1c2ccccc2CCN1S(=O)(=O)c1ccc(Br)cc1OC(F)(F)F)N1CCCC1] | N-[(2-{[4-Bromo-2-(trifluoromethoxy)phenyl]sulfonyl}-1,2,3,4-tetrahydro-1-isoquinolinyl)methyl]-1-pyrrolidinecarboxamide | 4.34 | 12484 |
| 27 | 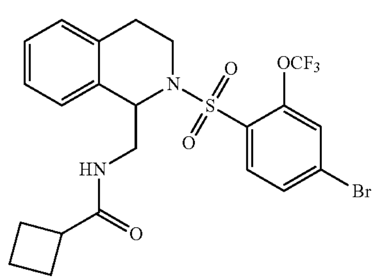 [SMILES: O=C(NCC1c2ccccc2CCN1S(=O)(=O)c1ccc(Br)cc1OC(F)(F)F)C1CCC1] | N-[(2-{[4-Bromo-2-(trifluoromethoxy)phenyl]sulfonyl}-1,2,3,4-tetrahydro-1-isoquinolinyl)methyl]cyclobutanecarboxamide | 1.34 | 13461 |

-continued

| No. | Structure | Name | FLIPR Ca²⁺ EC$_{50}$ (μM) | AUC |
|---|---|---|---|---|
| 28 | 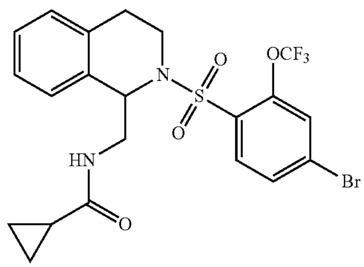 [SMILES: O=C(NCC1c2ccccc2CCN1S(=O)(=O)c1ccc(Br)cc1OC(F)(F)F)C1CC1] | N-[(2-{[4-Bromo-2-(trifluoromethoxy)phenyl]sulfonyl}-1,2,3,4-tetrahydro-1-isoquinolinyl)methyl]cyclopropanecarboxamide | 5.03 | 11880 |
| 29 | 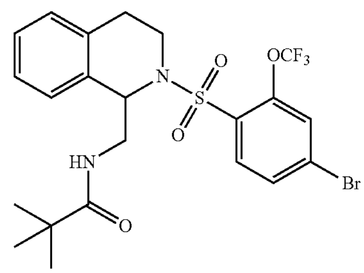 [SMILES: CC(C)(C)C(=O)NCC1c2ccccc2CCN1S(=O)(=O)c1ccc(Br)cc1OC(F)(F)F] | N-[(2-{[4-Bromo-2-(trifluoromethoxy)phenyl]sulfonyl}-1,2,3,4-tetrahydro-1-isoquinolinyl)methyl]-2,2-dimethylpropanamide | 4.61 | 12780 |
| 35 | 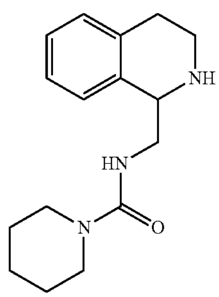 [SMILES: O=C(NCC1NCCc2ccccc21)N1CCCCC1] | N-(1,2,3,4-Tetrahydro-1-isoquinolinylmethyl)-1-piperidinecarboxamide | 3.31 | 5531 |
| 36 | 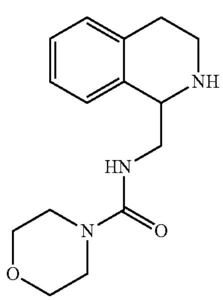 [SMILES: O=C(NCC1NCCc2ccccc21)N1CCOCC1] | N-(1,2,3,4-Tetrahydro-1-isoquinolinylmethyl)-4-morpholinecarboxamide | 8.08 | 5361 |
| 37 | 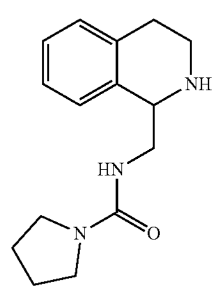 [SMILES: O=C(NCC1NCCc2ccccc21)N1CCCC1] | N-(1,2,3,4-Tetrahydro-1-isoquinolinylmethyl)-1-pyrrolidinecarboxamide | 4.02 | 3480 |

-continued

| No. | Structure | Name | FLIPR Ca$^{2+}$ EC$_{50}$ (μM) | AUC |
|---|---|---|---|---|
| 38 | 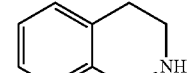 | 4-Methyl-N-(1,2,3,4-tetrahydro-1-isoquinolinylmethyl)benzamide | 0.14 | 14065 |
| 39 | 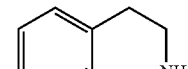 | 4-Methyl-N-(1,2,3,4-tetrahydro-1-isoquinolinylmethyl)cyclohexanecarboxamide | 1.53 | 12657 |
| 40 | 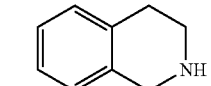 | 4-Ethyl-N-(1,2,3,4-tetrahydro-1-isoquinolinylmethyl)cyclohexanecarboxamide | 1.12 | 10059 |
| 41 | 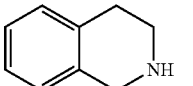 | 2-Methyl-N-(1,2,3,4-tetrahydro-1-isoquinolinylmethyl)cyclohexanecarboxamide | 10 | 5627 |
| 42 | 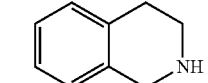 | 4-Methoxy-N-(1,2,3,4-tetrahydro-1-isoquinolinylmethyl)cyclohexanecarboxamide | 6.60 | 5538 |

-continued

| No. | Structure | Name | FLIPR Ca$^{2+}$ EC$_{50}$ (μM) | AUC |
|---|---|---|---|---|
| 43 | 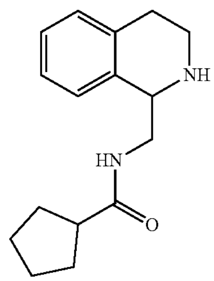 [SMILES: O=C(NCC1NCCc2ccccc21)C1CCCC1] | N-(1,2,3,4-Tetrahydro-1-isoquinolinylmethyl) cyclopentanecarboxamide | 8.91 | 5768 |
| 44 | 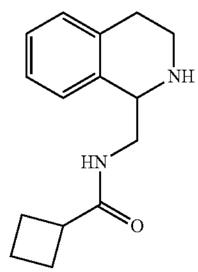 [SMILES: O=C(NCC1NCCc2ccccc21)C1CCC1] | N-(1,2,3,4-Tetrahydro-1-isoquinolinylmethyl) cyclobutanecarboxamide | 6.80 | 3646 |
| 45 | 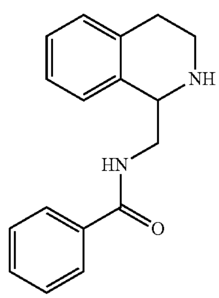 [SMILES: O=C(NCC1NCCc2ccccc21)c1ccccc1] | N-(1,2,3,4-Tetrahydro-1-isoquinolinylmethyl) benzamide | 0.75 | 8628 |
| 46 | 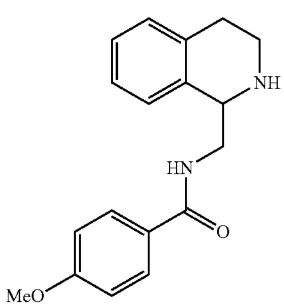 [SMILES: COc1ccc(C(=O)NCC2NCCc3ccccc32)cc1] | 4-Methoxy-N-(1,2,3,4-tetrahydro-1-isoquinolinylmethyl) benzamide | 0.37 | 12560 |
| 47 | 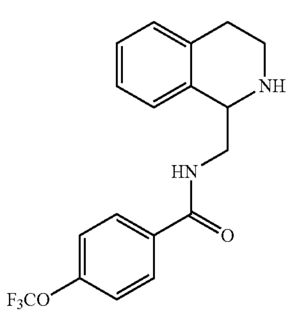 [SMILES: O=C(NCC1NCCc2ccccc21)c1ccc(OC(F)(F)F)cc1] | N-(1,2,3,4-Tetrahydro-1-isoquinolinylmethyl)-4-(trifluoromethoxy)benzamide | 0.37 | 13758 |

| No. | Structure | Name | FLIPR Ca$^{2+}$ EC$_{50}$ (μM) | AUC |
|---|---|---|---|---|
| 48 | 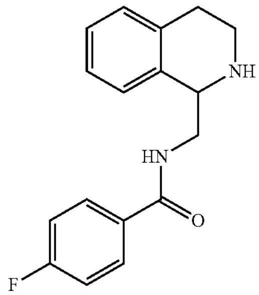 [SMILES: O=C(NCC1NCCc2ccccc21)c1ccc(F)cc1] | 4-Fluoro-N-(1,2,3,4-tetrahydro-1-isoquinolinylmethyl)benzamide | 0.54 | 13060 |
| 49 | 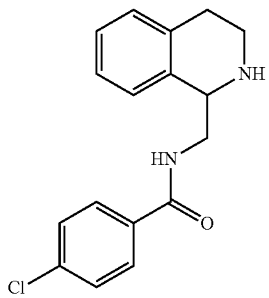 [SMILES: O=C(NCC1NCCc2ccccc21)c1ccc(Cl)cc1] | 4-Chloro-N-(1,2,3,4-tetrahydro-1-isoquinolinylmethyl)benzamide | 0.23 | 15448 |
| 50 | 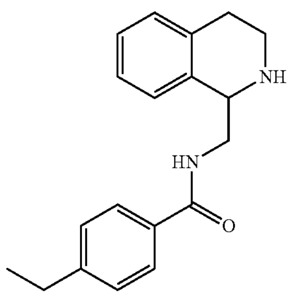 [SMILES: CCc1ccc(C(=O)NCC2NCCc3ccccc32)cc1] | 4-Ethyl-N-(1,2,3,4-tetrahydro-1-isoquinolinylmethyl)benzamide | 0.06 | 29879 |
| 51 | 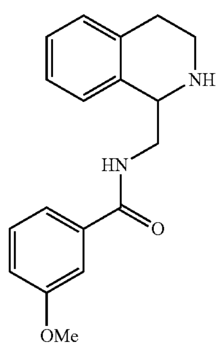 [SMILES: COc1cccc(C(=O)NCC2NCCc3ccccc32)c1] | 3-Methoxy-N-(1,2,3,4-tetrahydro-1-isoquinolinylmethyl)benzamide | 0.86 | 13302 |
| 52 | 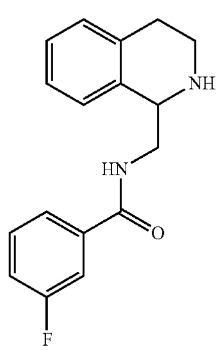 [SMILES: O=C(NCC1NCCc2ccccc21)c1cccc(F)c1] | 3-Fluoro-N-(1,2,3,4-tetrahydro-1-isoquinolinylmethyl)benzamide | 0.78 | 11425 |

-continued
| No. | Structure | Name | FLIPR Ca²⁺ EC$_{50}$ (μM) | AUC |
|---|---|---|---|---|
| 53 | 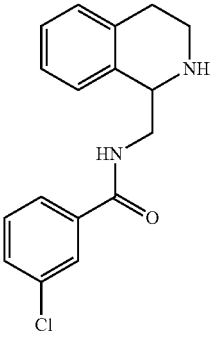 | 3-Chloro-N-(1,2,3,4-tetrahydro-1-isoquinolinylmethyl)benzamide | 0.38 | 13149 |
| 54 | 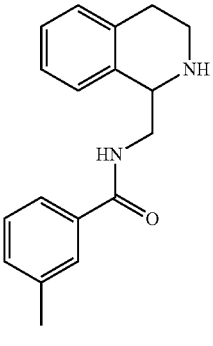 | 3-Methyl-N-(1,2,3,4-tetrahydro-1-isoquinolinylmethyl)benzamide | 0.37 | 16947 |
| 55 | 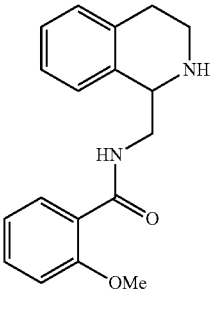 [SMILES: COc1ccccc1C(=O)NCC1NCCc2ccccc21] | 2-Methoxy-N-(1,2,3,4-tetrahydro-1-isoquinolinylmethyl)benzamide | 3.31 | 4312 |
| 56 | 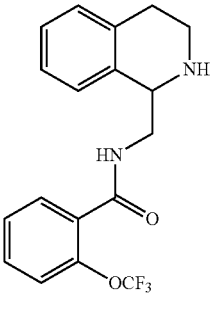 | N-(1,2,3,4-Tetrahydro-1-isoquinolinylmethyl)-2-(trifluoromethoxy)benzamide | 3.31 | 7855 |
| 57 | 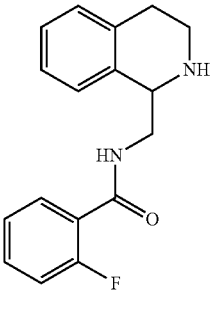 | 2-Fluoro-N-(1,2,3,4-tetrahydro-1-isoquinolinylmethyl)benzamide | 3.28 | 12102 |

| No. | Structure | Name | FLIPR Ca²⁺ EC$_{50}$ (μM) | AUC |
| --- | --- | --- | --- | --- |
| 58 | 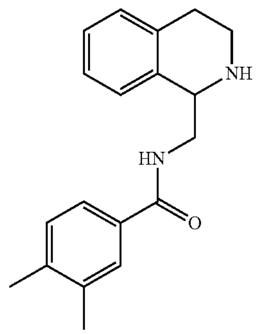 [SMILES: Cc1ccc(C(=O)NCC2NCCc3ccccc32)cc1C] | 3,4-Dimethyl-N-(1,2,3,4-tetrahydro-1-isoquinolinylmethyl)benzamide | 0.12 | 12759 |
| 59 | 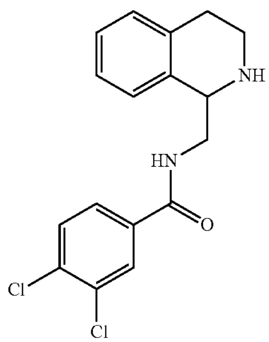 [SMILES: O=C(NCC1NCCc2ccccc21)c1ccc(Cl)c(Cl)c1] | 3,4-Dichloro-N-(1,2,3,4-tetrahydro-1-isoquinolinylmethyl)benzamide | 0.25 | 16200 |
| 60 | 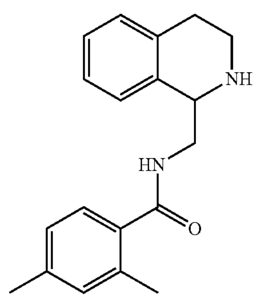 [SMILES: Cc1ccc(C(=O)NCC2NCCc3ccccc32)c(C)c1] | 2,4-Dimethyl-N-(1,2,3,4-tetrahydro-1-isoquinolinylmethyl)benzamide | 0.66 | 13375 |
| 61 | 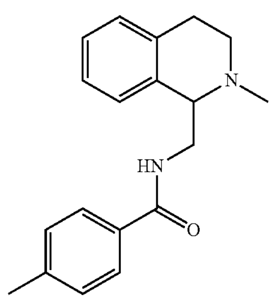 | 4-Methyl-N-[(2-methyl-1,2,3,4-tetrahydro-1-isoquinolinyl)methyl]benzamide | 0.04 | 14757 |
| 62 | 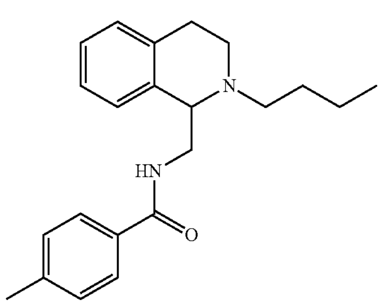 [SMILES: CCCCN1CCc2ccccc2C1CNC(=O)c1ccc(C)cc1] | N-[(2-Butyl-1,2,3,4-tetrahydro-1-isoquinolinyl)methyl]-4-methylbenzamide | 0.16 | 14669 |

| No. | Structure | Name | FLIPR Ca²⁺ EC$_{50}$ (μM) | AUC |
|---|---|---|---|---|
| 63 | 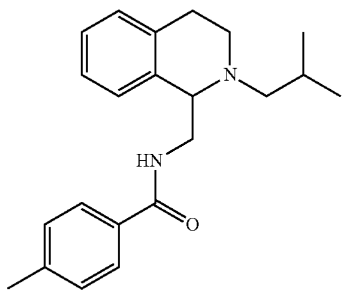 [SMILES: Cc1ccc(C(=O)NCC2c3ccccc3CCN2CC(C)C)cc1] | 4-Methyl-N-{[2-(2-methylpropyl)-1,2,3,4-tetrahydro-1-isoquinolinyl]methyl}benzamide | 0.11 | 18418 |
| 64 | 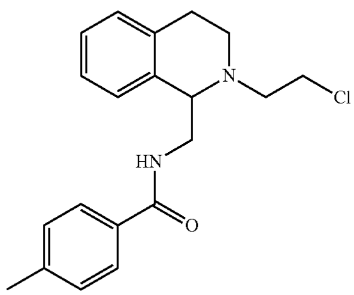 [SMILES: Cc1ccc(C(=O)NCC2c3ccccc3CCN2CCCl)cc1] | N-{[2-(2-Chloroethyl)-1,2,3,4-tetrahydro-1-isoquinolinyl]methyl}-4-methylbenzamide | 0.03 | 29079 |
| 65 | 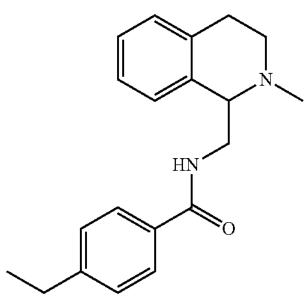 [SMILES: CCc1ccc(C(=O)NCC2c3ccccc3CCN2C)cc1] | 4-Ethyl-N-(2-methyl-1,2,3,4-tetrahydro-1-isoquinolinyl)methyl]benzamide | 0.01 | 18367 |
| 66 | 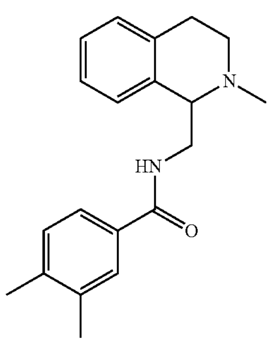 | 3,4-Dimethyl-N-[(2-methyl-1,2,3,4-tetrahydro-1-isoquinolinyl)methyl]benzamide | 0.01 | 17393 |

| No. | Structure | Name | FLIPR Ca$^{2+}$ EC$_{50}$ (μM) | AUC |
|---|---|---|---|---|
| 67 | 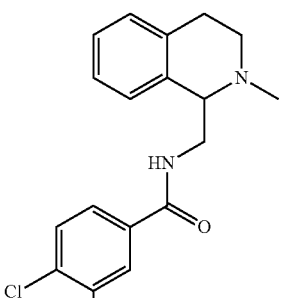 | 3,4-Dichloro-N-[(2-methyl-1,2,3,4-tetrahydro-1-isoquinolinyl)methyl]benzamide | 0.01 | 17879 |

Described below are the procedures used to synthesize the above-described 56 exemplary compounds. Note that the synthesis of these compounds was described in a grace-period inventor disclosure, i.e., Chen et al., European Journal of Medicinal Chemistry, 2017, 126, 202-217.

All the reagents and solvents were purchased from commercial sources and used without further purification unless otherwise indication. All the reactions were carried out under dry nitrogen or argon atmosphere and monitored by thin layer chromatography (TLC) using Merck Silica gel 60 F$_{254}$ glass-backed plate. Column chromatography was performed by Merck silica gel 60 (0.040-0.063 mm, 230-400 mesh). $^1$H NMR and $^{13}$C NMR spectra were measured by Varian Mercury-300 and Varian Mercury-400 spectrometers, and the chemical shifts (δ) were reported in parts per million (ppm) relative to the resonance of the solvent peak. Multiplicities are reported with the following abbreviations: s (singlet), d (doublet), t (triplet), q (quartet), quin (quintet), m (multiplet), or br (broad). Low-resolution mass spectra were measured by HP Hewlett Packard 1100 series.

The following four schemes were followed for synthesizing the compounds of formula (I).

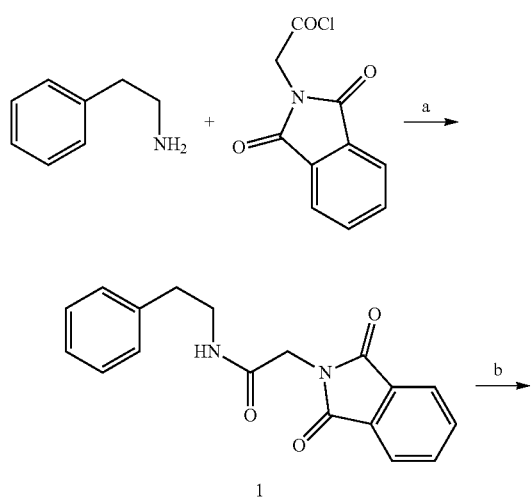

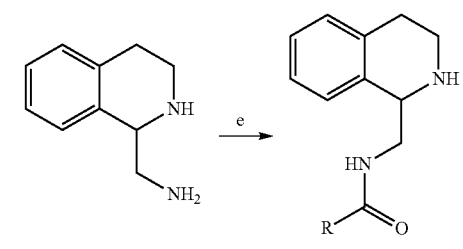

Reagents and conditions:
(a) Et$_3$N, CH$_2$Cl$_2$, room temperature, 2 h (94%);
(b) POCl$_3$, CH$_3$CN, reflux, 60 h (65%);
(c) NaBH(OAc)$_3$, CH$_2$Cl$_2$, AcOH, room temperature, 6 h (81%);
(d) 1. N$_2$H$_4$ (99%), EtOH, reflux, 40 min, and
2. 38% HCl$_{(aq)}$, reflux, 40 min (100%); and
(e) acyl chloride, CH$_3$CN, pyridine, 2N HCl$_{(aq)}$, CHCl$_3$, room temperature, 2 h (16-69%).

Scheme 2.

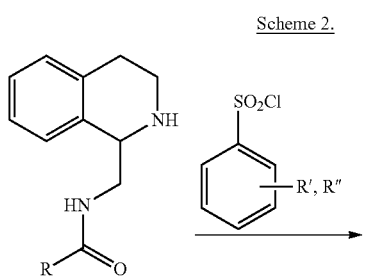

5, 35, 37, 39, 43-45

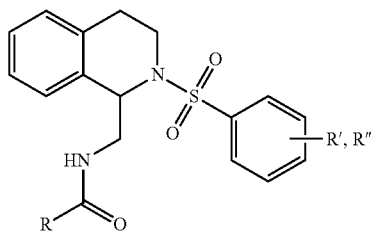

6-21, 24-29

Reagents and conditions: DIPEA, CH₂Cl₂, room temperature, 2 h.

Scheme 3.

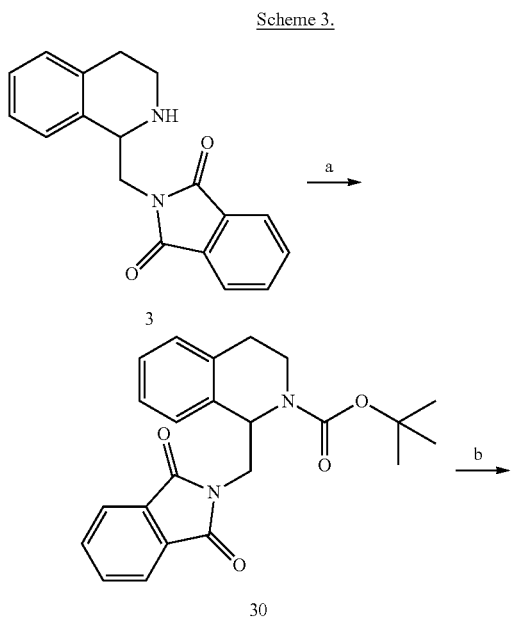

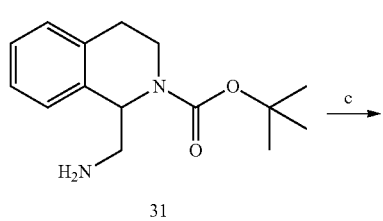

31

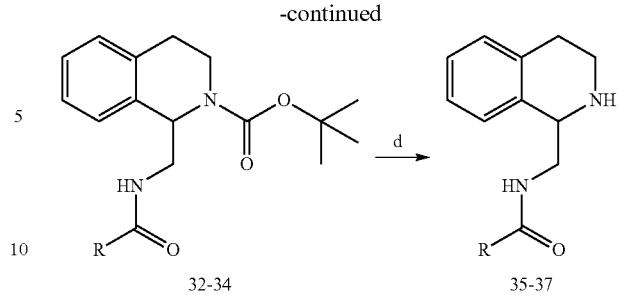

32-34 → 35-37

Reagents and conditions:
(a) Boc₂O, NaHCO₃, CH₂Cl₂, room temperature, 1 h (100%);
(b) N₂H₄ (99%), CH₃CN, reflux, 32 h (100%);
(c) acyl carbamate, Et₃N, CH₂Cl₂, room temperature, 8 h (91-95%); and
(d) TFA, CH₂Cl₂, room temperature, 3 h (41-99%).

Scheme 4.

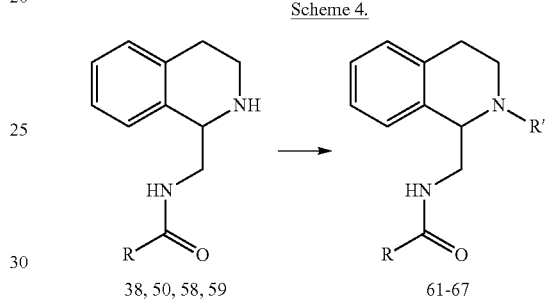

38, 50, 58, 59 → 61-67

Reagents and conditions: aldehyde, NaBH(OAc)₃, CH₃CN, room temperature, 6 h (37-96%).

Example 1

2-(1,3-Dioxo-1,3-dihydro-2H-isoindol-2-yl)-N-(2-phenylethyl)acetamide

Compound 1

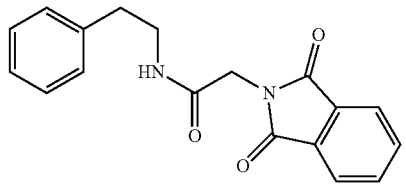

To a solution of phthalylglycyl chloride (6.46 g, 28.9 mmol) in CH₂Cl₂ (80 mL) was added β-phenylethylamine (3.55 mL, 28.2 mmol) and triethylamine (7.61 mL, 56.4 mmol). The solution was stirred at room temperature for 1.5 h. To the solution was added 30 mL of water and extracted with CH₂Cl₂ (2×40 mL). The organic layer was dried over MgSO₄ and the solvent was evaporated under reduced pressure. The crude product was purified by crystallization from 50 mL of MeOH to afford the amide as a white solid (8.20 g 94%). $^1$H NMR (300 MHz, CDCl₃) δ 7.90-7.85 (m, 2H), 7.78-7.74 (m, 2H), 7.27-7.15 (m, 5H), 5.69 (br t, 1H), 4.29 (s, 2H), 3.54 (q, 2H), 2.82 (t, 2H); MS (ESI) m/z 309.1 (M+H).

Example 2

2-(3,4-Dihydro-1-isoquinolinylmethyl)-1H-isoindole-1,3(2H)-dione

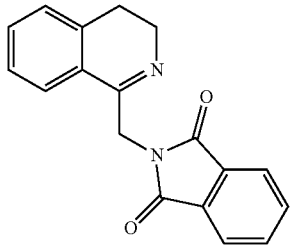

Compound 2

To a solution of 2-(1,3-dioxo-1,3-dihydro-2H-isoindol-2-yl)-N-(2-phenylethyl)acetamide 2 (12.4 g, 40.3 mmol) in CH₃CN (124 mL) was added POCl₃ (11.3 mL, 121 mmol). The solution was refluxed for 63 h, cooled to room temperature and concentrated under reduced pressure. The residue was dissolved in 50 mL of CH$_2$Cl$_2$ and washed with 100 mL of NaOH$_{(aq)}$, and brine (2×50 mL). The organic layer was dried over MgSO$_4$ and the solvent was evaporated under reduced pressure. The crude product was purified by flash column chromatography (SiO$_2$, CH$_2$Cl$_2$/MeOH=98/2) to afford the dihydroisoquinoline as a yellow solid (7.61 g, 65%). $^1$H NMR (400 MHz, CDCl$_3$) δ 7.89-7.87 (m, 2H), 7.73-7.71 (m, 2H), 7.52 (d, 1H), 7.41-7.28 (m, 2H), 7.20 (d, 1H), 4.92 (s, 2H), 3.61 (dd, 2H), 2.68 (t, 2H); MS (ESI) m/z 291.1 (M+H), 158.0.

Example 3

2-(1,2,3,4-Tetrahydro-1-isoquinolinylmethyl)-1H-isoindole-1,3(2H)-dione

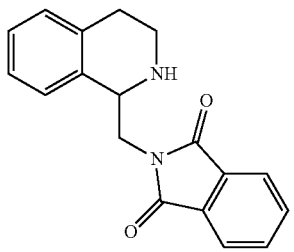

Compound 3

To a solution of 2-(3,4-dihydro-1-isoquinolinylmethyl)-1H-isoindole-1,3(2H)-dione 2 (0.100 g, 0.340 mmol) in CH$_2$Cl$_2$ (1.72 mL) was added NaBH(OAc)$_3$ (0.370 g, 1.72 mmol) and AcOH (0.02 mL). The solution was stirred at room temperature for 1 h. The solution was diluted with CH$_2$Cl$_2$ (40 mL) and washed with water (2×10 mL). The organic layer was dried over MgSO$_4$ and the solvent was evaporated under reduced pressure. The crude product was purified by flash column chromatography (SiO$_2$, CH$_2$Cl$_2$/MeOH=94/6) to afford the tetrahydroisoquinoline as a yellow solid (80.0 mg, 81%). $^1$H NMR (300 MHz, CDCl$_3$) δ 7.91-7.82 (m, 2H), 7.76-7.68 (m, 2H), 7.34-7.28 (m, 1H), 7.24-7.08 (m, 2H), 4.39 (dd, 1H), 4.09 (dd, 1H), 3.90 (dd, 1H), 3.34 (dt, 1H), 2.98 (dt, 1H), 2.81-2.78 (m, 2H); MS (ESI) m/z 293.0 (M+H).

Example 4

1-(1,2,3,4-Tetrahydro-1-isoquinolinyl)methanamine

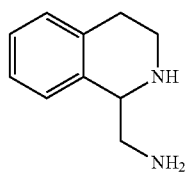

Compound 4

To a solution of 2-(1,2,3,4-tetrahydro-1-isoquinolinylmethyl)-1H-isoindole-1,3(2H)-dione 3 (1.01 g, 3.46 mmol) in ethanol (29.6 mL) was added hydrazine. The solution was refluxed for 40 min, cooled to room temperature, concentrated under reduced pressure and then refluxed again for 40 min with 17.4 mL of 37% HCl$_{(aq)}$. The precipitate was filtered off and the filtrate was neutralized with solid NaOH and extracted with CH$_2$Cl$_2$ (3×100 mL). The organic layer was dried over MgSO$_4$, and concentrated to afford the diamine as a yellow liquid (0.560 g, 100%). $^1$H NMR (300 MHz, CDCl$_3$); δ 7.22-7.03 (m, 4H), 4.10-3.98 (m, 1H), 3.25-3.17 (m, 1H), 3.11-2.98 (m, 3H), 2.91-2.69 (m, 2H); MS (ESI) m/z 163.1 (M+H).

The procedure for preparing Compound 5 below ("procedure A") wag followed to synthesize Compounds 38-60.

Example 5

N-(1,2,3,4-Tetrahydro-1-isoquinolinylmethyl)cyclohexanecarboxamide

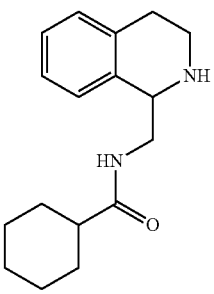

Compound 5

To a solution of 1-(1,2,3,4-tetrahydro-1-isoquinolinyl)methanamine 4 (0.900 g, 5.54 mmol), pyridine (0.600 mL) and 2N HCl (2.70 mL, 5.39 mmol) in CH$_3$CN (8.99 mL), was added a solution of cyclohexanecarbonyl chloride (1.10 mL, 8.31 mmol) dissolved in 4.24 mL of CHCl$_3$ slowly during 45 min. The solution was stirred at room temperature for 2 h and then concentrated under reduced pressure. Diethyl ether (50 mL) was added to the residue and the solution was extracted with 1N HCl (3×30 ml). The water layer was neutralized with solid NaOH and extracted with CH$_2$Cl$_2$ (3×30 ml). The organic layer was dried over MgSO$_4$ and the solvent was evaporated under reduced pressure. The crude product was purified by flash column chromatography (SiO$_2$, CH$_2$Cl$_2$/MeOH=95/5) to afford the amide as a yellow solid (1.04 g, 69%). $^1$H NMR (300 MHz, CDCl$_3$) δ 7.22-7.05 (m, 4H), 6.32 (br t, 1H), 4.11 (dd, 1H), 3.78 (ddd, 1H), 3.36 (ddd, 1H), 3.22-3.11 (m, 1H), 3.09-2.99 (m, 1H), 2.88-2.70 (m, 2H), 2.07 (tt, 1H), 1.88-1.59 (m, 5H), 1.48-1.00 (m, 5H); MS (ESI) m/z 273.1 (M+H).

The procedure for preparing Compound 6 below ("procedure B") was followed to synthesize Compounds 7-19 and 22.

Example 6

N-[(2-{[4-Bromo-2-(trifluoromethoxy)phenyl]sulfonyl}-1,2,3,4-tetrahydro-1-isoquinolinyl)methyl]cyclohexanecarboxamide

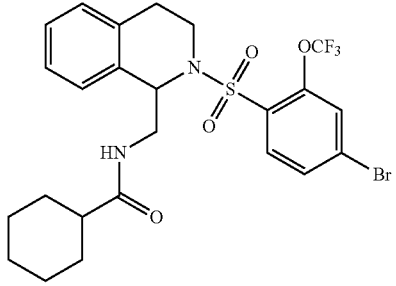

Compound 6

To a solution of N-(1,2,3,4-tetrahydro-1-isoquinolinylmethyl)cyclohexanecarboxamide 5 (40.0 mg, 150 μmol) and N,N-diisopropylethylamine (30.0 μL, 150 μmol) in 0.4 mL of CH$_2$Cl$_2$ was added 4-bromo-2-(trifluoromethoxy)benzene-1-sulfonyl chloride (30.0 μL, 150 μmol). The solution was stirred at room temperature for 2 h. To the solution was added 10 mL of water and extracted with CH$_2$Cl$_2$ (3×10 mL). The organic layer was dried over MgSO$_4$ and the solvent was evaporated under reduced pressure. The crude product was purified by flash column chromatography (SiO$_2$, CH$_2$Cl$_2$/MeOH=98/2) to afford the sulfonamide as a white solid (80.0 mg, 97%). $^1$H NMR (300 MHz, CDCl$_3$) δ 7.91 (d, 1H), 7.48 (d, 1H), 7.34 (s, 1H), 7.22-7.10 (m, 3H), 6.99 (d, 1H), 6.12 (br t, 1H), 5.15 (dd, 1H), 3.83 (dd, 1H), 3.67-3.48 (m, 3H), 2.60 (ddd, 1H), 2.42 (ddd, 1H), 2.14 (tt, 1H), 2.02-1.75 (m, 4H), 1.71-1.62 (m, overlapped with br s at 1.66, 1H), 1.46 (q, 2H), 1.37-1.13 (m, 3H); MS (ESI) m/z 575.0 (M+H).

Example 7

N-[(2-{[4-Bromo-2-(trifluoromethyl)phenyl]sulfonyl}-1,2,3,4-tetrahydro-1-isoquinolinyl)methyl]cyclohexanecarboxamide

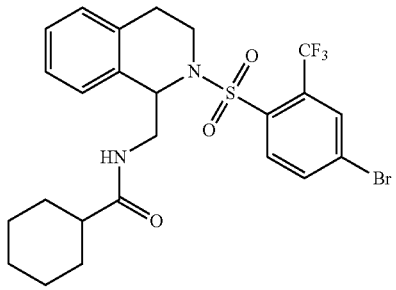

Compound 7

The reaction of N-(1,2,3,4-tetrahydro-1-isoquinolinylmethyl)cyclohexanecarboxamide 5 (60.0 mg, 0.220 mmol) with 4-bromo-2-(trifluoromethyl)benzenesulfonyl chloride (80.0 mg, 0.240 mmol) was performed by following procedure B. The crude product was purified by flash column chromatography (SiO$_2$, CH$_2$Cl$_2$/MeOH=99/1) to afford the sulfonamide as a white solid (0.110 g, 90%). $^1$H NMR (300 MHz, CDCl$_3$) δ 7.93 (d, 1H), 7.86 (d, 1H), 7.68 (dd, 1H), 7.25-7.15 (m, 3H), 7.04-7.02 (m, 1H), 6.04 (br t, 1H), 5.09 (t, 1H), 3.87 (dd, 1H), 3.61-3.51 (m, 3H), 2.72-2.52 (m, 2H), 2.08 (tt, 1H), 1.97-1.74 (m, 4H), 1.70-1.51 (m, overlapped with br s at 1.60, 1H), 1.42 (q, 2H), 1.32-1.12 (m, 3H); MS (ESI) m/z 581.0 (M+Na).

Example 8

N-({2-[(4-Bromo-2-methylphenyl)sulfonyl]-1,2,3,4-tetrahydro-1-isoquinolinyl}methyl)cyclohexanecarboxamide

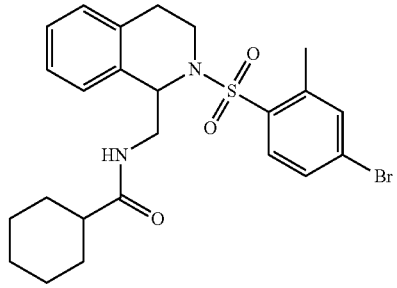

Compound 8

The reaction of N-(1,2,3,4-tetrahydro-1-isoquinolinylmethyl)cyclohexanecarboxamide 5 (60.0 mg, 0.220 mmol) with 4-bromo-2-methylbenzenesulfonyl chloride (70.0 mg, 0.240 mmol) was performed by following procedure B. The crude product was purified by flash column chromatography (SiO$_2$, CH$_2$Cl$_2$/MeOH=99/1) to afford the sulfonamide as a white solid (0.100 g, 92%). $^1$H NMR (300 MHz, CDCl$_3$) δ 7.79 (d, 1H), 7.39 (d, overlapped with s at 7.37, 2H), 7.25-7.13 (m, 3H), 7.03 (d, 1H), 6.13 (br t, 1H), 5.14 (d, 1H), 3.74-3.61 (m, 2H), 3.52-3.39 (m, 2H), 2.65-2.42 (m, 2H), 2.35 (s, 3H), 2.18-2.06 (m, 1H), 2.00-1.75 (m, 4H), 1.71-1.58 (m, overlapped with br s at 1.63, 1H), 1.46 (q, 2H), 1.36-1.19 (m, 3H); MS (ESI) m/z 527.1 (M+Na).

Example 9

N-({2-[(4-Bromophenyl)sulfonyl]-1,2,3,4-tetrahydro-1-isoquinolinyl}methyl)cyclohexanecarboxamide

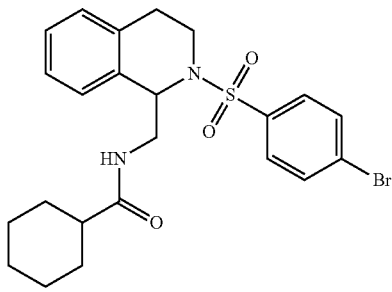

Compound 9

The reaction of N-(1,2,3,4-tetrahydro-1-isoquinolinylmethyl)cyclohexanecarboxamide 5 (60.0 mg, 0.220 mmol) with 4-bromobenzene-1-sulfonyl chloride (60.0 m g, 0.220 mmol) was performed by following procedure B. The crude product was purified by flash column chromatography (SiO$_2$, CH$_2$Cl$_2$/MeOH=98/2) to afford the sulfonamide as a white solid (0.100 g, 97%). $^1$H NMR (300 MHz, CDCl$_3$) δ 7.56 (d, 2H), 7.46 (d, 2H), 7.22-7.08 (m, 3H), 6.92 (d, 1H), 6.20 (br t, 1H), 5.04 (dd, 1H), 3.96-3.84 (m, 1H), 3.67 (ddd, 1H), 3.57-3.32 (m, 2H), 2.62-2.35 (m, 2H), 2.16 (tt, 1H), 2.03-1.58 (m, overlapped with br s at 1.69, 5H), 1.48 (q, 2H), 1.38-1.13 (m, 3H); MS (ESI) m/z 491.3 (M+H).

Example 10

N-({2-[(2,4-Dibromophenyl)sulfonyl]-1,2,3,4-tetrahydro-1-isoquinolinyl}methyl)cyclohexanecarboxamide

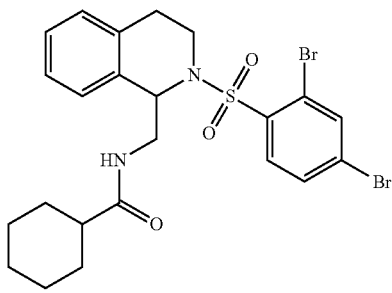

Compound 10

The reaction of N-(1,2,3,4-tetrahydro-1-isoquinolinylmethyl)cyclohexanecarboxamide 5 (50.0 mg, 0.180 mmol) with 2,4-dibromobenzenesulfonyl chloride (70.0 mg, 0.200 mmol) was performed by following procedure B. The crude product was purified by flash column chromatography (SiO$_2$, CH$_2$Cl$_2$/MeOH=98/2) to afford the sulfonamide as a white solid (90.0 mg, 88%). $^1$H NMR (300 MHz, CDCl$_3$) δ 8.02 (d, 1H), 7.81 (s, 1H), 7.56 (d, 1H), 7.23-7.15 (m, 3H), 7.08-7.01 (m, 1H), 6.04 (br t, 1H), 5.24 (dd, 1H), 3.76 (dt, 1H), 3.66 (ddd, 1H), 3.56-3.45 (m, 2H), 2.64-2.59 (m, 2H), 2.07 (tt, 1H), 1.99-1.75 (m, 4H), 1.72-1.62 (m, 1H), 1.44 (q, 2H), 1.37-1.14 (m, 3H); MS (ESI) m/z 591.0 (M+Na).

Example 11

N-({2-[(4-Bromo-2-chlorophenyl)sulfonyl]-1,2,3,4-tetrahydro-1-isoquinolinyl}methyl)cyclohexanecarboxamide

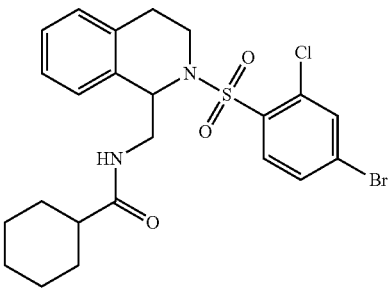

Compound 11

The reaction of N-(1,2,3,4-tetrahydro-1-isoquinolinylmethyl)cyclohexanecarboxamide 5 (50.0 mg, 0.180 mmol) with 4-bromo-2-chlorobenzenesulfonyl chloride (60.0 mg, 0.200 mmol) was performed by following procedure B. The crude product was purified by flash column chromatography (SiO$_2$, CH$_2$Cl$_2$/MeOH=98/2) to afford the sulfonamide as a white solid (90.0 mg, 90%). $^1$H NMR (300 MHz, CDCl$_3$) δ 7.97 (d, 1H), 7.57 (s, 1H), 7.51 (d, 1H), 7.21-7.14 (m, 3H), 7.03 (d, 1H), 6.08 (br t, 1H), 5.23 (dd, 1H), 3.82-3.71 (m, 1H), 3.67-3.47 (m, 3H), 2.66-2.49 (m, 2H), 2.09 (tt, 1H), 2.00-1.75 (m, 4H), 1.71-1.53 (m, overlapped with br s at 1.59, 1H), 1.44 (q, 2H), 1.37-1.13 (m, 3H); MS (ESI) m/z 547.0 (M+Na).

Example 12

N-({2-[(4-Bromo-2-fluorophenyl)sulfonyl]-1,2,3,4-tetrahydro-1-isoquinolinyl}methyl)cyclohexanecarboxamide

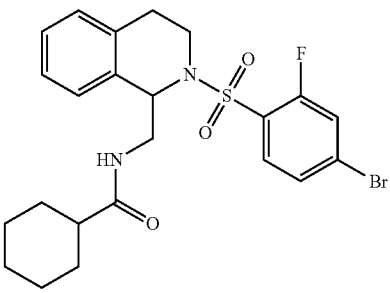

Compound 12

The reaction of N-(1,2,3,4-tetrahydro-1-isoquinolinylmethyl)cyclohexanecarboxamide 5 (50.0 mg, 0.180 mmol) with 4-bromo-2-fluorobenzenesulfonyl chloride (60.0 mg, 0.200 mmol) was performed by following procedure B. The crude product was purified by flash column chromatography (SiO$_2$, CH$_2$Cl$_2$/MeOH=98/2) to afford the sulfonamide as a white solid (80.0 mg, 89%). $^1$H NMR (300 MHz, CDCl$_3$) δ 7.76 (t, 1H), 7.35 (d, 1H), 7.21-7.12 (m, 4H), 6.99 (d, 1H), 6.14 (br t, 1H), 5.14 (dd, 1H), 3.91 (ddd, 1H), 3.63-3.47 (m, 3H), 2.68-2.47 (m, 2H), 2.14 (tt, 1H), 2.02-1.74 (m, 4H), 1.71-1.59 (m, overlapped with br s at 1.65, 1H), 1.46 (q, 2H), 1.37-1.14 (m, 3H); MS (ESI) m/z 531.1 (M+Na).

Example 13

N-[(2-{[2-(Trifluoromethoxy)phenyl]sulfonyl}-1,2,3,4-tetrahydro-1-isoquinolinyl)methyl]cyclohexanecarboxamide

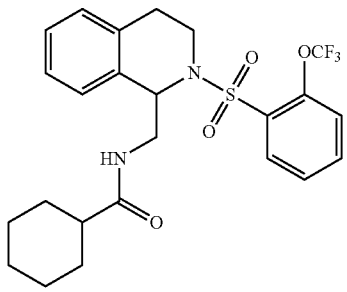

Compound 13

The reaction of N-(1,2,3,4-tetrahydro-1-isoquinolinylmethyl)cyclohexanecarboxamide 5 (50.0 mg, 0.180 mmol) with 2-(trifluoromethoxy)benzenesulfonyl chloride (50.0 mg, 0.200 mmol) was performed by following procedure B. The crude product was purified by flash column chromatography (SiO$_2$, CH$_2$Cl$_2$/MeOH=98/2) to afford the sulfonamide as a white solid (80.0 mg, 87%). $^1$H NMR (300 MHz, CDCl$_3$) δ 8.05 (d, 1H), 7.53 (t, 1H), 7.34 (t, 1H), 7.21-7.10 (m, 4H), 6.96 (d, 1H), 6.16 (br t, 1H), 5.24-5.10 (m, 1H), 3.86 (dd, 1H), 3.64-3.48 (m, 3H), 2.59-2.50 (m, 1H), 2.59-2.50 (m, 1H), 2.39 (ddd, 1H), 2.14 (tt, 1H), 2.03-1.74 (m, 4H), 1.71-1.58 (m, overlapped with br s at 1.64, 1H), 1.46 (q, 2H), 1.37-1.14 (m, 3H); MS (ESI) m/z 519.1 (M+Na).

Example 14

N-({2-[(2-Methoxyphenyl)sulfonyl]-1,2,3,4-tetrahydro-1-isoquinolinyl}methyl)cyclohexanecarboxamide

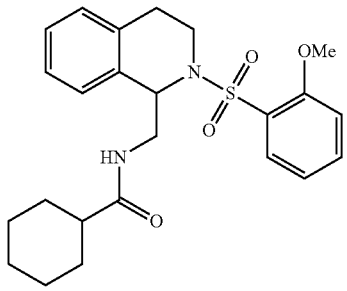

Compound 14

The reaction of N-(1,2,3,4-tetrahydro-1-isoquinolinylmethyl)cyclohexanecarboxamide 5 (40.0 mg, 0.150 mmol) with 4-methoxybenzenesulfonyl chloride (30.0 mg, 0.160 mmol) was performed by following procedure B. The crude product was purified by flash column chromatography (SiO$_2$, CH$_2$Cl$_2$/MeOH=98/2) to afford the sulfonamide as a white solid (30.0 mg, 45%). $^1$H NMR (300 MHz, CDCl$_3$) δ 7.99 (d, 1H), 7.45 (t, 1H), 7.28 (d, 1H), 7.20 (t, 1H), 7.12 (t, 1H), 7.01 (t, 1H), 6.95 (d, 1H), 6.72 (d, 1H), 6.30 (br t, 1H), 5.35 (dd, 1H), 3.84-3.70 (m, 2H), 3.50-3.37 (m, 2H), 3.16 (s, 3H), 2.41 (dd, 1H), 2.24-2.14 (m, 2H), 2.06-1.94 (m, 2H), 1.87-1.75 (m, 2H), 1.70-1.55 (m, overlapped with br s at 1.59, 1H), 1.49 (q, 2H), 1.38-1.14 (m, 3H); MS (ESI) m/z 465.1 (M+Na).

Example 15

N-[(2-{[4-Fluoro-2-(trifluoromethyl)phenyl]sulfonyl}-1,2,3,4-tetrahydro-1-isoquinolinyl)methyl]cyclohexanecarboxamide

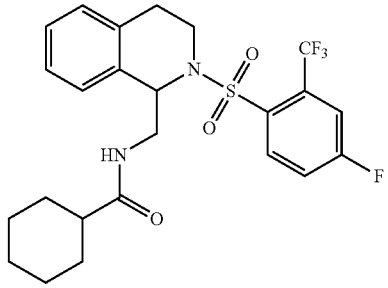

Compound 15

The reaction of N-(1,2,3,4-tetrahydro-1-isoquinolinylmethyl)cyclohexanecarboxamide (60.0 mg, 0.220 mmol) with 4-fluoro-2-(trifluoromethyl)benzenesulfonyl chloride 5 (60.0 mg, 0.220 mmol) was performed by following procedure B. The crude product was purified by flash column chromatography (SiO$_2$, CH$_2$Cl$_2$/MeOH=99/1) to afford the sulfonamide as a white solid (0.100 g, 90%). $^1$H NMR (300 MHz, CDCl$_3$) δ 8.04 (dd, 1H), 7.51 (dd, 1H), 7.26-7.14 (m, 4H), 7.02 (d, 1H), 6.07 (br t, 1H), 5.11 (t, 1H), 3.86 (dd, 1H), 3.61-3.51 (m, 3H), 2.70-2.48 (m, 2H), 2.10 (tt, 1H), 2.00-1.78 (m, 4H), 1.73-1.60 (m, overlapped with br s at 1.66, 1H), 1.43 (q, 2H) 1.34-1.18 (m, 3H); MS (ESI) m/z 499.2 (M+H).

Example 16

N-({2-[(4-Fluoro-2-methylphenyl)sulfonyl]-1,2,3,4-tetrahydro-1-isoquinolinyl}methyl)cyclohexanecarboxamide

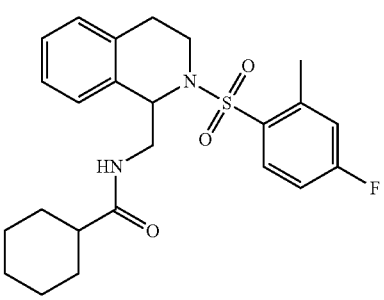

Compound 16

The reaction of N-(1,2,3,4-tetrahydro-1-isoquinolinylmethyl)cyclohexanecarboxamide 5 (60.0 mg, 0.220 mmol) with 4-fluoro-2-methylbenzenesulfonyl chloride (40.0 mg, 0.240 mmol) was performed by following procedure B. The crude product was purified by flash column chromatography (SiO$_2$, CH$_2$Cl$_2$/MeOH=99/1) to afford the sulfonamide as a white solid (90.0 mg, 96%). $^1$H NMR (300 MHz, CDCl$_3$) δ 7.97 (dd, 1H), 7.28-7.15 (m, overlapped with s at 7.26, 3H), 7.02 (d, 1H), 6.98-6.89 (m, 2H), 6.15 (br t, 1H), 5.15 (dd, 1H), 3.76-3.63 (m, 2H), 3.50-3.39 (m, 2H), 2.62-2.40 (m, 2H), 2.36 (s, 3H), 2.13 (tt, 1H), 1.98-1.78 (m, 4H), 1.72-1.58 (m, overlapped with br s at 1.63, 1H), 1.46 (q, 2H), 1.38-1.14 (m, 3H); MS (ESI) m/z 467.1 (M+Na).

Example 17

N-({2-[(4-Chlorophenyl)sulfonyl]-1,2,3,4-tetrahydro-1-isoquinolinyl}methyl)cyclohexanecarboxamide

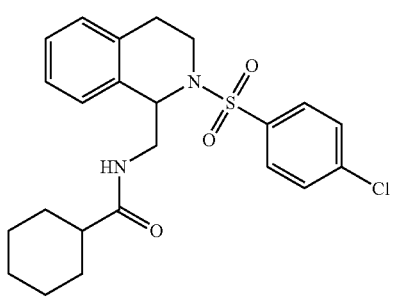

Compound 17

The reaction of N-(1,2,3,4-tetrahydro-1-isoquinolinylmethyl)cyclohexanecarboxamide 5 (60.0 mg, 0.220 mmol) with 4-chlorobenzenesulfonyl chloride (60.0 mg, 0.260 mmol) was performed by following procedure B. The crude product was purified by flash column chromatography (SiO$_2$, CH$_2$Cl$_2$/MeOH=98.5/1.5) to afford the sulfonamide as a white solid (0.110 g, 100%). $^1$H NMR (300 MHz, CDCl$_3$) δ 7.64 (d, 2H), 7.30 (d, 2H), 7.20-7.10 (m, 3H), 6.92 (d, 1H), 6.18 (br t, 1H), 5.05 (dd, 1H), 3.91 (dd, 1H), 3.68 (ddd, 1H), 3.50 (ddd, 1H), 3.39 (ddd, 1H), 2.61-2.50 (m, 1H), 2.43 (ddd, 1H), 2.17 (tt, 1H), 2.04-1.73 (m, 5H), 1.48 (q, 2H), 1.38-1.14 (m, 3H); MS (ESI) m/z 469.1 (M+Na).

Example 18

N-({2-[(4-Methylphenyl)sulfonyl]-1,2,3,4-tetrahydro-1-isoquinolinyl}methyl)cyclohexanecarboxamide

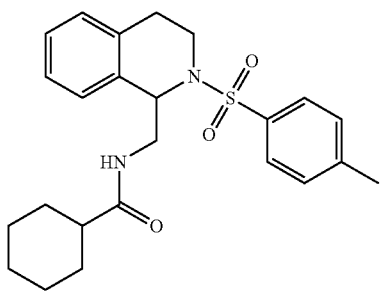

Compound 18

The reaction of N-(1,2,3,4-tetrahydro-1-isoquinolinylmethyl)cyclohexanecarboxamide 5 (40.0 mg, 0.150 mmol) with p-toluenesulfonyl chloride (30.0 mg, 0.160 mmol) was performed by following procedure B. The crude product was purified by flash column chromatography (SiO$_2$, CH$_2$Cl$_2$/MeOH=98/2) to afford the sulfonamide as a white solid (40.0 mg, 69%). $^1$H NMR (300 MHz, CDCl$_3$) δ 7.58 (d, 2H), 7.20-7.07 (m, 5H), 6.90 (d, 1H), 6.28 (br t, 1H), 5.04 (dd, 1H), 3.91 (ddd, 1H), 3.69 (ddd, 1H), 3.48 (ddd, 1H), 3.36 (ddd, 1H), 2.58-2.37 (m, 2H), 2.32 (s, 3H), 2.17 (tt, 1H), 2.04-1.75 (m, 4H), 1.71-1.58 (m, overlapped with br s at 1.63, 1H), 1.48 (q, 2H), 1.37-1.14 (m, 3H); MS (ESI) m/z 449.2 (M+Na).

Example 19

N-({2-[(4-Methoxyphenyl)sulfonyl]-1,2,3,4-tetrahydro-1-isoquinolinyl}methyl)cyclohexanecarboxamide

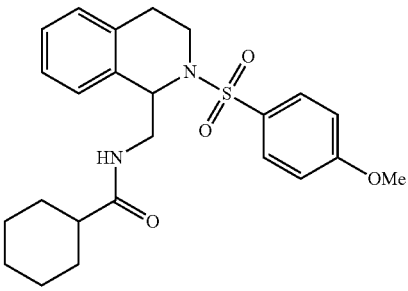

Compound 19

The reaction of N-(1,2,3,4-tetrahydro-1-isoquinolinylmethyl)cyclohexanecarboxamide 5 (60.0 mg, 0.220 mmol) with 4-methoxybenzenesulfonyl chloride (50.0 mg, 0.220 mmol) was performed by following procedure B. The crude product was purified by flash column chromatography (SiO$_2$, CH$_2$Cl$_2$/MeOH=98/2) to afford the sulfonamide as a white solid (70.0 mg, 76%). $^1$H NMR (300 MHz, CDCl$_3$) δ 7.66-7.61 (m, 2H), 7.25-7.07 (m, 3H), 6.91 (d, 1H), 6.81-6.76 (m, 2H), 6.28 (br t, 1H), 5.03 (dd, 1H), 3.89 (ddd, 1H), 3.78 (s, 3H), 3.70 (ddd, 1H), 3.46 (ddd, 1H), 3.35 (ddd, 1H), 2.57-2.39 (m, 2H), 2.17 (tt, 2H), 2.04-1.91 (m, 2H), 1.86-1.75 (m, 2H), 1.72-1.62 (m, overlapped with br s at 1.67, 1H), 1.48 (q, 2H), 1.38-1.18 (m, 3H); MS (ESI) m/z 443.2 (M+H).

Example 20

N-[(2-{[4-Bromo-2-(trifluoromethoxy)phenyl]sulfonyl}-1,2,3,4-tetrahydro-1-isoquinolinyl)methyl]-4-methylcyclohexanecarboxamide

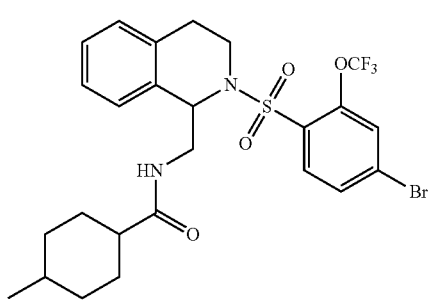

Compound 20

To a solution of 4-methyl-N-(1,2,3,4-tetrahydro-1-isoquinolinylmethyl)cyclohexanecarboxamide 42 (50.0 mg, 0.170 mmol) and N,N-diisopropylethylamine (30.0 µL, 0.170 mmol) in CH$_2$Cl$_2$ (0.5 mL) was added 4-bromo-2-(trifluoromethoxy)benzene-1-sulfonyl chloride (40.0 µL, 0.190 mmol). The solution was stirred at room temperature for 2 h. To the solution was added 5 mL of water and extracted with CH$_2$Cl$_2$ (2×10 mL). The organic layer was dried over MgSO$_4$ and the solvent was evaporated under reduced pressure. The crude product was purified by flash column chromatography (SiO$_2$, CH$_2$Cl$_2$/MeOH=99/1) to afford the sulfonamide as a white solid (90.0 mg, 88%). $^1$H NMR (300 MHz, CDCl$_3$) δ 7.91 (dd, 1H), 7.48 (d, 1H), 7.34 (s, 1H), 7.23-7.11 (m, 3H), 6.99 (d, 1H), 6.25-6.03 (m, 1H), 5.16 (dd, 1H), 3.83 (dd, 1H), 3.68-3.47 (m, 3H), 2.66-2.54 (m, 1H), 2.43 (ddd, 1H), 2.30 (tt, 1H), 2.13-1.18 (m, overlapped with br s at 1.61, 9H), 0.96 (d, 2H), 0.89 (d, 1H); MS (ESI) m/z 611.1 (M+Na).

Example 21

N-[(2-{[4-Bromo-2-(trifluoromethoxy)phenyl]sulfonyl}-1,2,3,4-tetrahydro-1-isoquinolinyl)methyl]cyclopentanecarboxamide

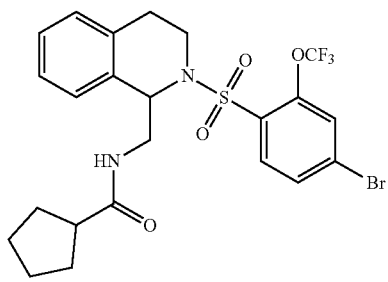

Compound 21

To a solution of N-(1,2,3,4-tetrahydro-1-isoquinolinylmethyl)cyclopentanecarboxamide 47 (50.0 mg, 0.190 mmol) and N,N-diisopropylethylamine (30.0 µL, 0.190 mmol) in CH$_2$Cl$_2$ (0.5 mL) was added 4-bromo-2-(trifluoromethoxy)benzene-1-sulfonyl chloride (40.0 µL, 0.200 mmol). The solution was stirred at room temperature for 2 h. To the solution was added 5 mL of water and extracted with CH$_2$Cl$_2$ (2×10 mL). The organic layer was dried over MgSO$_4$ and the solvent was evaporated under reduced pressure. The crude product was purified by flash column chromatography (SiO$_2$, CH$_2$Cl$_2$/MeOH=98.5/1.5) to afford the sulfonamide as a white solid (80.0 mg, 75%). $^1$H NMR (300 MHz, CDCl$_3$) δ 7.91 (d, 1H), 7.48 (d, 1H), 7.34 (s, 1H), 7.22-7.13 (m, 3H), 6.99 (d, 1H), 6.10 (br t, 1H), 5.15 (dd, 1H), 3.83 (dd, 1H), 3.67-3.50 (m, 3H), 2.65-2.51 (m, 2H), 2.50-2.36 (m, 1H), 2.01-1.68 (m, 6H), 1.68-1.47 (m, overlapped with br s at 1.64, 2H); MS (ESI) m/z 561.0 (M+H).

Example 22

2-[(2-{[4-Bromo-2-(trifluoromethoxy)phenyl]sulfonyl}-1,2,3,4-tetrahydro-1-isoquinolinyl)methyl]-1H-isoindole-1,3(2H)-dione

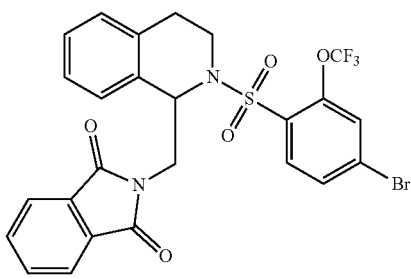

Compound 22

The reaction of 2-(1,2,3,4-tetrahydro-1-isoquinolinylmethyl)-1H-isoindole-1,3(2H)-dione 3 (40.0 mg, 0.150 mmol) with 4-bromo-2-(trifluoromethoxy)benzene-1-sulfonyl chloride (30.0 µL, 0.160 mmol) was performed by following procedure B. The crude product was purified by flash column chromatography (SiO$_2$, ethyl acetate/hexane=1/3) to afford the sulfonamide as a white solid (60.0 mg, 63%). $^1$H NMR (300 MHz, CDCl$_3$) δ 7.82-7.72 (m, 5H), 7.32-7.27 (m, 2H), 7.26-7.20 (m, 2H), 7.18-7.10 (m, 1H), 6.97 (s, 1H), 5.37 (dd, 1H), 4.14-4.01 (m, 2H), 3.86-3.73 (m, 2H), 2.81-2.76 (m, 2H); MS (ESI) m/z 595.0 (M+H).

Example 23

1-(2-{[4-Bromo-2-(trifluoromethoxy)phenyl]sulfonyl}-1,2,3,4-tetrahydro-1-isoquinolinyl)methanamine

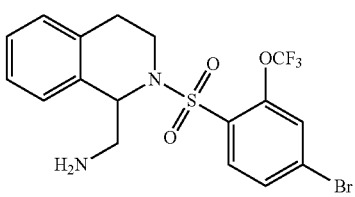

Compound 23

To a solution of 2-[(2-{[4-bromo-2-(trifluoromethoxy)phenyl]sulfonyl}-1,2,3,4-tetrahydro-1-isoquinolinyl)methyl]-1H-isoindole-1,3(2H)-dione 22 (2.35 g, 3.95 mmol) in ethanol/CHCl$_3$ (10.2/24.1 mL) was added hydrazine. The solution was refluxed for 72 h, cooled to room temperature and concentrated under reduced pressure. The residue was dissolved in 100 mL of CH$_2$Cl$_2$ and filtered. The filtrate was added 50 mL of water and extracted with CH$_2$Cl$_2$ (2×100 mL). The organic layer was dried over MgSO$_4$ and the solvent was evaporated under reduced pressure to afford the amine as a brown solid (1.89 g, 100%). $^1$H NMR (300 MHz, CDCl$_3$) δ 7.95 (d, 1H), 7.49 (d, 1H), 7.35 (s, 1H), 7.20-7.07 (m, 3H), 6.99 (d, 1H), 4.96 (dd, 1H), 3.86 (ddd, 1H), 3.51 (ddd, 1H), 3.04-2.90 (m, 2H), 2.63-2.49 (m, 2H); MS (ESI) m/z 465.0 (M+H).

The procedure for preparing Compound 24 below ('procedure C") was followed to synthesize Compounds 25-29.

Example 24

N-[(2-{[4-Bromo-2-(trifluoromethoxy)phenyl]sulfonyl}-1,2,3,4-tetrahydro-1-isoquinolinyl)methyl]benzamide

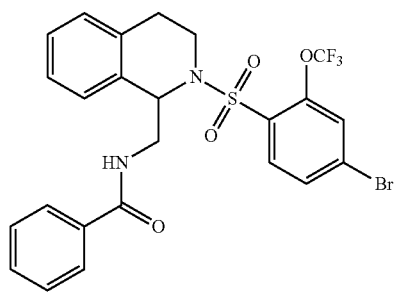

Compound 24

To a solution of 1-(2-{[4-bromo-2-(trifluoromethoxy)phenyl]sulfonyl}-1,2,3,4-tetrahydro-1-isoquinolinyl)methananamine 23 (0.100 g, 0.210 mmol) and N,N-diisopropylethylamine (70.0 μL, 0.410 mmol) in CH$_2$Cl$_2$ (2.15 mL) was added benzoyl chloride (30.0 μL, 0.250 mmol). The solution was stirred at room temperature for 1.5 h. To the solution was added 5 mL of water and extracted with CH$_2$Cl$_2$ (2×10 mL). The organic layer was dried over MgSO$_4$ and the solvent was evaporated under reduced pressure. The crude product was purified by flash column chromatography (SiO$_2$, CH$_2$Cl$_2$) to afford the amide as a powder (0.120 g, 98%). $^1$H NMR (400 MHz, CDCl$_3$) δ 7.90 (d, 1H), 7.85 (d, 2H), 7.54-7.43 (m, 4H), 7.30 (s, 1H), 7.23-7.17 (m, 3H), 7.05 (d, 1H), 6.85 (br t, 1H), 5.34-5.24 (m, 1H), 3.92 (dd, 1H), 3.80-3.77 (m, 2H), 3.61 (ddd, 1H), 2.67 (ddd, 1H), 2.55 (ddd, 1H); MS (ESI) m/z 569.0 (M+H).

Example 25

N-[(2-{[4-Bromo-2-(trifluoromethoxy)phenyl]sulfonyl}-1,2,3,4-tetrahydro-1-isoquinolinyl)methyl]-1-piperidinecarboxamide

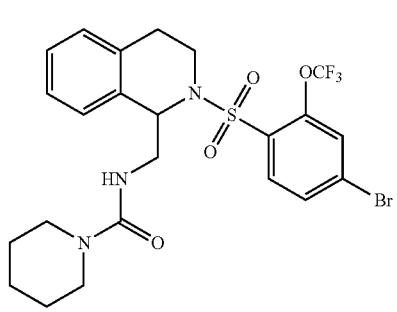

Compound 25

The reaction of 1-(2-{[4-bromo-2-(trifluoromethoxy)phenyl]sulfonyl}-1,2,3,4-tetrahydro-1-isoquinolinyl)methanamine 23 (70.0 mg, 0.150 mmol) with 1-piperidinecarbonyl chloride (20.0 μL, 0.180 mmol) and triethylamine (40.0 μL, 0.300 mmol) was performed by following procedure C. The crude product was purified by flash column chromatography (SiO$_2$, CH$_2$Cl$_2$/MeOH=97/3) to afford the amide as a yellow solid (80.0 mg, 89%). $^1$H NMR (300 MHz, (CD$_3$)$_2$CO) δ 7.96 (d, 1H), 7.73 (d, 1H), 7.57 (s, 1H), 7.23-7.13 (m, 3H), 7.05 (d, 1H), 5.95 (br t, 1H), 5.20 (t, 1H), 3.99 (dd, 1H), 3.66 (ddd, 1H), 3.44 (t, 2H), 3.34-3.20 (m, 4H), 2.75-2.54 (m, 2H), 1.62-1.42 (m, 6H); MS (ESI) m/z 576.0 (M+H).

Example 26

N-[(2-{[4-Bromo-2-(trifluoromethoxy)phenyl]sulfonyl}-1,2,3,4-tetrahydro-1-isoquinolinyl)methyl]-1-pyrrolidinecarboxamide

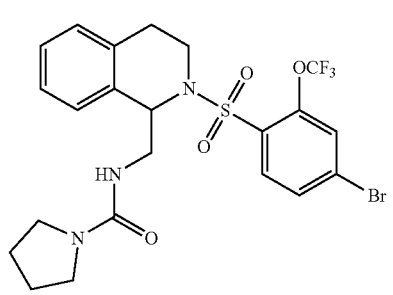

Compound 26

The reaction of 1-(2-{[4-bromo-2-(trifluoromethoxy)phenyl]sulfonyl}-1,2,3,4-tetrahydro-1-isoquinolinyl)methanamine 23 (70.0 mg, 0.150 mmol) with 1-pyrrolidinecarbonyl chloride (20.0 μL, 0.180 mmol) and triethylamine (40.0 μL, 0.300 mmol) was performed by following procedure C. The crude product was purified by flash column chromatography (SiO$_2$, CH$_2$Cl$_2$/MeOH=96/4) to afford the amide as a yellow solid (70.0 mg, 85%). $^1$H NMR (300 MHz, CDCl$_3$) δ 7.90 (d, 1H), 7.48 (d, 1H), 7.35 (s, 1H), 7.22-7.12 (m, 3H), 7.00 (d, 1H), 5.15 (t, 1H), 4.87 (br t, 1H), 3.84 (dd, 1H), 3.62-3.54 (m, 3H), 3.45-3.24 (m, 4H), 2.66-2.55 (m, 1H), 2.46 (ddd, 1H), 2.00-1.79 (m, 4H); MS (ESI) m/z 562.0 (M+H).

Example 27

N-[(2-{[4-Bromo-2-(trifluoromethoxy)phenyl]sulfonyl}-1,2,3,4-tetrahydro-1-isoquinolinyl)methyl]cyclobutanecarboxamide

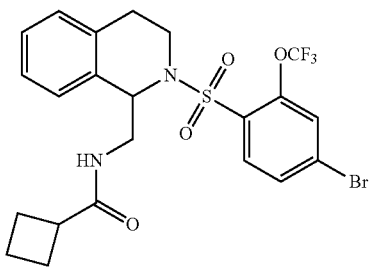

Compound 27

The reaction of 1-(2-{[4-bromo-2-(trifluoromethoxy)phenyl]sulfonyl}-1,2,3,4-tetrahydro-1-isoquinolinyl)methanamine 23 (70.0 mg, 0.150 mmol) with cyclobutanecarbonyl chloride (20.0 μL, 0.170 mmol) was performed by following procedure C. The crude product was purified by flash column chromatography (SiO$_2$, CH$_2$Cl$_2$/MeOH=98/2) to afford the amide as a yellow liquid (50.0 mg, 61%). $^1$H NMR (300 MHz, CDCl$_3$) δ 7.91 (d, 1H), 7.48 (d, 1H), 7.34 (s, 1H), 7.22-7.13 (m, 3H), 7.00 (d, 1H), 6.00 (br t, 1H), 5.14 (dd, 1H), 3.81 (dd, 1H), 3.68-3.48 (m, 3H), 3.07 (quin, 1H), 2.66-2.55 (m, 1H), 2.49-2.12 (m, 5H), 2.04-1.80 (m, 2H); MS (ESI) m/z 547.0 (M+H).

Example 28

N-[(2-{[4-Bromo-2-(trifluoromethoxy)phenyl]sulfonyl}-1,2,3,4-tetrahydro-1-isoquinolinyl)methyl]cyclopropanecarboxamide

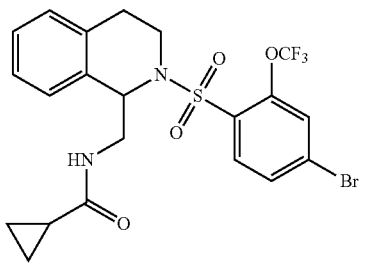

Compound 28

The reaction of 1-(2-{[4-bromo-2-(trifluoromethoxy)phenyl]sulfonyl}-1,2,3,4-tetrahydro-1-isoquinolinyl)methanamine 23 (60.0 mg, 0.130 mmol) with cyclopropanecarbonyl chloride (10.0 μL, 0.150 mmol) was performed by following procedure C. The crude product was purified by flash column chromatography (SiO$_2$, CH$_2$Cl$_2$/MeOH=97/3) to afford the amide as a yellow solid (60.0 mg, 93%). $^1$H NMR (300 MHz, CDCl$_3$) δ 7.92 (d, 1H), 7.50 (d, 1H), 7.37 (s, 1H), 7.25-7.13 (m, 3H), 7.01 (d, 1H), 6.16 (br t, 1H), 5.14 (t, 1H), 3.89 (dd, 1H), 3.60-3.49 (m, 3H), 2.63 (ddd, 1H), 2.51 (ddd, 1H), 1.37 (tt, 1H), 1.05-0.93 (m, 2H), 0.84-0.71 (m, 2H); MS (ESI) m/z 533.0 (M+H).

Example 29

N-[(2-{[4-Bromo-2-(trifluoromethoxy)phenyl]sulfonyl}-1,2,3,4-tetrahydro-1-isoquinolinyl)methyl]-2,2-dimethylpropanamide

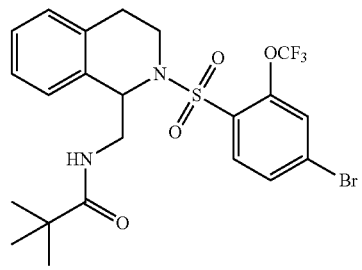

Compound 29

The reaction of 1-(2-{[4-bromo-2-(trifluoromethoxy)phenyl]sulfonyl}-1,2,3,4-tetrahydro-1-isoquinolinyl)methanamine 23 (60.0 mg, 0.130 mmol) with trimethyl acetyl chloride (20.0 μL, 0.150 mmol) was performed by following procedure C. The crude product was purified by flash column chromatography (SiO$_2$, CH$_2$Cl$_2$/MeOH=98/2) to afford the amide as a yellow solid (60.0 mg, 88%). $^1$H NMR (300 MHz, CDCl$_3$) δ 7.91 (d, 1H), 7.48 (d, 1H), 7.33 (s, 1H), 7.22-7.13 (m, 3H), 6.99, (d, 1H), 6.40 (br t, 1H), 5.18 (dd, 1H), 3.81 (dd, 1H), 3.67-3.50 (m, 3H), 2.59 (ddd, 1H), 2.39 (ddd, 1H), 1.26 (s, 9H); MS (ESI) m/z 549.0 (M+H).

Example 30

2-Methyl-2-propanyl 1-[(1,3-dioxo-1,3-dihydro-2H-isoindol-2-yl)methyl]-3,4-dihydro-2(1H)-isoquinolinecarboxylate

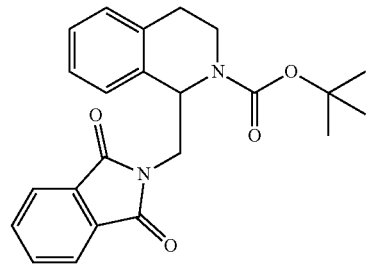

Compound 30

To a solution of 2-(1,2,3,4-tetrahydro-1-isoquinolinylmethyl)-1H-isoindole-1,3(2H)-dione 3 (0.100 g, 0.340 mmol) in CH$_2$Cl$_2$ (2.08 mL) was added di-tert-butyl dicarbonate (0.330 mL, 14.5 mmol) and NaHCO$_3$ (0.130 g, 1.59 mL). The solution was stirred at room temperature for 1 h. The solution was diluted with 25 mL of CH$_2$Cl$_2$ and washed with water (2×25 mL). The organic layer was dried over MgSO$_4$ and the solvent was evaporated under reduced pressure. The crude product was purified by flash column chromatography (SiO$_2$, CH$_2$Cl$_2$/MeOH=94/6) to afford the carbamate as a yellow solid (0.140 g, 100%). $^1$H NMR (300 MHz, CDCl$_3$) δ 7.91-7.82 (m, 2H), 7.78-7.65 (m, 2H), 7.40-7.33 (m, 1H), 7.29-7.16 (m, 3H), 5.59 (dd, 0.4H), 5.43 (dd, 0.6H), 4.26

(dd, 0.6H), 4.14-3.94 (m, 1.4H), 3.86 (td, 1H), 3.52-3.34 (m, 1H), 3.01-2.75 (m, 2H), 1.12 (s, 3.5H), 1.03 (s, 5.5H); MS (ESI) m/z 415.1 (M+Na).

Example 31

2-Methyl-2-propanyl 1-(aminomethyl)-3,4-dihydro-2(1H)-isoquinolinecarboxylate

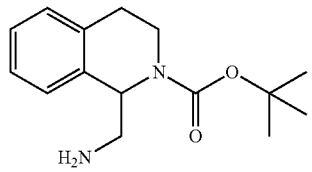

Compound 31

To a solution of 2-methyl-2-propanyl 1-[(1,3-dioxo-1,3-dihydro-2H-isoindol-2-yl)methyl]-3,4-dihydro-2(1H)-isoquinolinecarboxylate 30 (2.35 g, 5.99 mmol) in CH$_3$CN (24 mL) was added hydrazine (1.14 mL, 35.9 mmol). The solution was refluxed for 40 h. The solution was concentrated under reduced pressure. The residue was added 25 mL of water and extracted with CH$_2$Cl$_2$ (2×25 mL). The organic layer was dried over MgSO$_4$ and the solvent was evaporated under reduced pressure to afford the primary amine as a yellow liquid (1.57 g, 100%). $^1$H NMR (300 MHz, CDCl$_3$) δ 7.24-6.99 (m, 4H), 5.20-4.85 (m, 1H), 4.29-3.67 (m, 1H), 3.45-3.11 (m, 1H), 3.08-2.79 (m, 3H), 2.76 (t, 0.6H), 2.71 (t, 0.4H), 1.48 (s, 9H); MS (ESI) m/z 263.1 (M+H).

The procedure for preparing Compound 32 below ("procedure D") was followed to synthesize Compounds 33-34.

Example 32

2-Methyl-2-propanyl 1-[(1-piperidinylcarbonyl)amino]methyl)-3,4-dihydro-2(1H)-isoquinolinecarboxylate

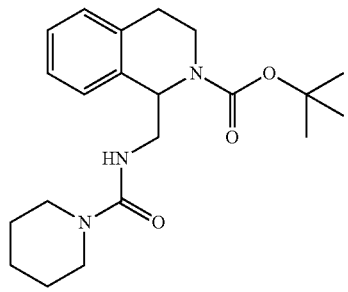

Compound 32

To a solution of 2-methyl-2-propanyl 1-(aminomethyl)-3,4-dihydro-2(1H)-isoquinolinecarboxylate 31 (80.0 mg, 0.290 mmol) in CH$_2$Cl$_2$ (0.960 mL) was added piperdinecarbonyl chloride (40.0 µL, 0.340 mmol) and triethylamine (80.0 µL, 0.570 mmol). The solution was stirred at room temperature for 8 h. To the solution was added 10 mL of water and extracted with CH$_2$Cl$_2$ (3×15 mL). The organic layer was dried over MgSO$_4$ and the solvent was evaporated under reduced pressure. The crude product was purified by flash column chromatography (SiO$_2$, CH$_2$Cl$_2$/MeOH=98/2) to afford the urea as a yellow solid (0.100 g, 91%). $^1$H NMR (300 MHz, CDCl$_3$) δ 7.24-7.08 (m, 4H), 5.76 (br t, 0.6H), 5.30 (dd, 1H), 4.76 (br s, 0.2H), 4.25 (br s, 0.2H), 4.01-3.85 (m, 0.6H), 3.79-3.52 (m, 1H), 3.50-3.03 (m, 6.4H), 3.03-2.56 (m, 2H), 1.66-1.49 (m, overlapped with br s at 1.61, 6H), 1.47 (s, 9H); MS (ESI) m/z 374.1 (M+H).

Example 33

2-Methyl-2-propanyl 1-{[(1-pyrrolidinylcarbonyl)amino]methyl}-3,4-dihydro-2(1H)-isoquinolinecarboxylate

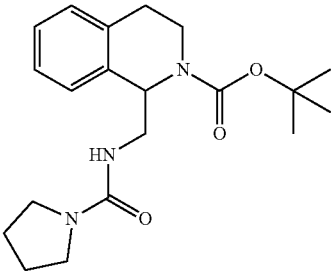

Compound 33

The reaction of 2-methyl-2-propanyl 1-(aminomethyl)-3,4-dihydro-2(1H)-isoquinolinecarboxylate 31 (0.400 g, 1.52 mmol) with pyrrolidinecarbonyl chloride (0.200 mL, 1.83 mmol) was performed by following procedure D. The crude product was purified by flash column chromatography (SiO$_2$, CH$_2$Cl$_2$/MeOH=96/4) to afford the urea as a yellow solid (0.520 g, 95%). $^1$H NMR (300 MHz, CDCl$_3$) δ 7.24-7.08 (m, 4H), 5.34-5.13 (m, 1.6H), 4.50 (br t, 0.2H), 4.36-3.20 (m, 0.2H), 4.02-3.87 (m, 0.6H), 3.82-3.53 (m, 1H), 3.50-3.06 (m, 6.4H), 3.03-2.64 (m, 2H), 1.99-1.76 (m, 4H), 1.46 (s, 9H); MS (ESI) m/z 360.2 (M+H).

Example 34

2-Methyl-2-propanyl 1-[(4-morpholinylcarbonyl)amino]methyl)-3,4-dihydro-2(1H)-isoquinolinecarboxylate

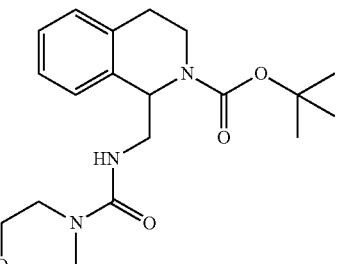

Compound 34

The reaction of 2-methyl-2-propanyl 1-(aminomethyl)-3,4-dihydro-2(1H)-isoquinolinecarboxylate 31 (0.400 g, 1.52 mmol) with 4-morpholinecarbonyl chloride (0.210 mL, 1.83 mmol) was performed by following procedure D. The crude product was purified by flash column chromatography (SiO$_2$, CH$_2$Cl$_2$/MeOH=96/4) to afford the urea as a yellow solid (0.540 g, 95%). $^1$H NMR (300 MHz, CDCl$_3$) δ 7.24-7.03 (m, 4H), 5.94 (br s, 1H), 5.40-5.20 (m, 1H), 4.03-3.81 (m, 1H), 3.81-3.52 (m, 5H), 3.52-3.01 (m, 6H), 3.01-2.54 (m, 2H), 1.48 (s, 9H); MS (ESI) m/z 376.2 (M+H).

The procedure for preparing Compound 35 below ("procedure E") was followed to synthesize Compounds 36 and 37.

Example 35

N-(1,2,3,4-Tetrahydro-1-isoquinolinylmethyl)-1-piperidinecarboxamide

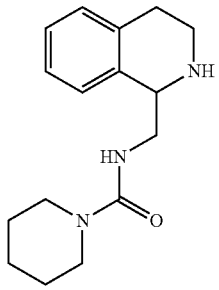

Compound 35

To a solution of 2-methyl-2-propanyl 1-{[(1-piperidinylcarbonyl)amino]methyl}-3,4-dihydro-2(1H)-isoquinolinecarboxylate 32 (0.200 g, 0.530 mmol) in CH$_2$Cl$_2$ (7.96 mL) was added trifluoroacetic acid (1.33 mL). The solution was stirred at room temperature for 3 h. To the solution was added 50 mL of NaHCO$_{3(aq)}$ and extracted with 50 mL of CH$_2$Cl$_2$. The organic layer was dried over MgSO$_4$ and the solvent was evaporated under reduced pressure to afford the urea as a yellow liquid (0.140 g, 96%). $^1$H NMR (300 MHz, CDCl$_3$) δ 7.24-7.04 (m, 4H), 5.67 (br t, 1H), 4.29 (dd, 1H), 3.79 (ddd, 1H), 3.39 (ddd, 1H), 3.31 (t, 4H), 3.27-3.05 (m, 2H), 2.93-2.77 (m, 2H), 1.64-1.45 (m, 6H); MS (ESI) m/z 274.1 (M+H).

Example 36

N-(1,2,3,4-Tetrahydro-1-isoquinolinylmethyl)-4-morpholinecarboxamide

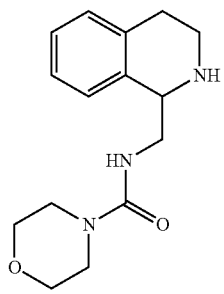

Compound 36

The reaction of 2-methyl-2-propanyl 1-{[(4-morpholinylcarbonyl)amino]methyl}-3,4-dihydro-2(1H)-isoquinolinecarboxylate 34 (0.460 g, 1.21 mmol) with trifluoroacetic acid (3.04 mL) was performed by following procedure E to afford the urea as a yellow liquid (0.140 g, 41%). $^1$H NMR (300 MHz, CDCl$_3$) δ 7.24-7.05 (m, 4H), 5.75 (br t, 1H), 4.20 (dd, 1H), 3.78 (ddd, 1H), 3.64 (t, 4H), 3.40-3.22 (m, 5H), 3.22-3.13 (m, 1H), 3.11-3.03 (m, 1H), 2.80 (t, 2H); MS (ESI) m/z 276.1 (M+H).

Example 37

N-(1,2,3,4-Tetrahydro-1-isoquinolinylmethyl)-1-pyrrolidinecarboxamide

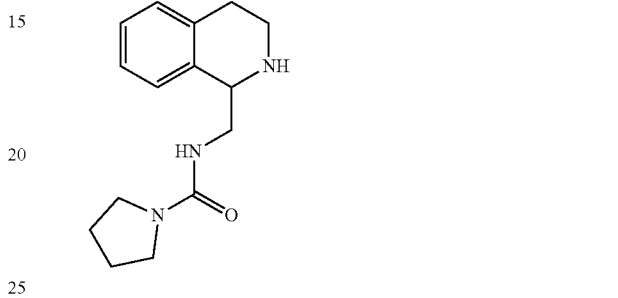

Compound 37

The reaction of 2-methyl-2-propanyl 1-{[(1-pyrrolidinylcarbonyl)amino]methyl}-3,4-dihydro-2(1H)-isoquinolinecarboxylate 33 (0.430 g, 1.21 mmol) with trifluoroacetic acid (3.02 mL) was performed by following procedure E to afford the urea as a yellow solid (0.310 g, 99%). $^1$H NMR (400 MHz, CDCl$_3$) δ 7.25-7.09 (m, 4H), 5.97 (br t, 1H), 4.58 (d, overlapped with br s at 4.43, 1H), 3.82-3.73 (m, 1H), 3.54 (ddd, 1H), 3.43-3.15 (m, 6H), 2.96 (t, 2H), 1.92-1.75 (m, 4H); MS (ESI) m/z 260.1 (M+H).

Example 38

4-Methyl-N-(1,2,3,4-tetrahydro-1-isoquinolinylmethyl)benzamide

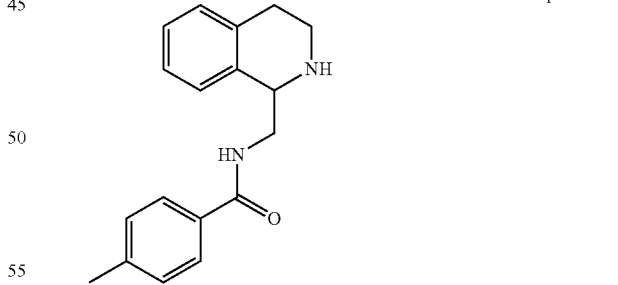

Compound 38

The reaction of 1-(1,2,3,4-tetrahydro-1-isoquinolinyl)methanamine 4 (0.300 g, 1.85 mmol) with p-toluoyl chloride (0.260 mL, 1.94 mmol) was performed by following procedure A. The crude product was purified by flash column chromatography (SiO$_2$, CH$_2$Cl$_2$/MeOH=94/6) to afford the amide as a yellow liquid (0.280 g, 53%). $^1$H NMR (300 MHz, CDCl$_3$) δ 7.70 (d, 1H), 7.28-7.07 (m, overlapped with s at 7.26, 7H), 4.25 (dd, 1H), 4.03 (ddd, 1H), 3.51 (ddd, 1H), 3.24-3.04 (m, 2H), 2.90-2.72 (m, 2H), 2.38 (s, 3H); MS (ESI) m/z 281.1 (M+H).

Example 39

4-Methyl-N-(1,2,3,4-tetrahydro-1-isoquinolinylmethyl)cyclohexanecarboxamide

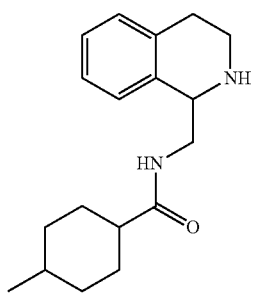

Compound 39

The reaction of 1-(1,2,3,4-tetrahydro-1-isoquinolinyl)methanamine 4 (0.300 g, 1.85 mmol) with 4-methylcyclohexanecarbonyl chloride (0.300 mL, 1.94 mmol) was performed by following procedure A. The crude product was purified by flash column chromatography ($SiO_2$, $CH_2Cl_2$/MeOH=95/5) to afford the amide as a yellow liquid (0.320 g, 61%). $^1$H NMR (300 MHz, $CDCl_3$) δ 7.24-7.03 (m, 4H), 6.42 (br t, 0.6H), 6.39 (br t, 0.4H), 4.16 (td, 1H), 3.83-3.70 (m, 1H), 3.48 (ddd, 0.7H), 3.38 (ddd, 0.3H), 3.25-3.00 (m, 2H), 2.92-2.71 (m, 2H), 2.24 (tt, 0.7H), 2.01 (tt, 0.3H), 1.89-1.15 (m, 9H), 0.91-0.89 (m, 3H); MS (ESI) m/z 287.2 (M+H).

Example 40

4-Ethyl-N-(1,2,3,4-tetrahydro-1-isoquinolinylmethyl)cyclohexanecarboxamide

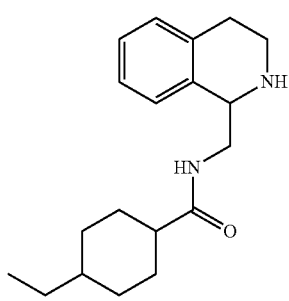

Compound 40

The reaction of 1-(1,2,3,4-tetrahydro-1-isoquinolinyl)methanamine 4 (0.100 g, 0.620 mmol) with 4-ethylcyclohaxanecarbonyl chloride (0.110 mL, 0.650 mmol) was performed by following procedure A. The crude product was purified by flash column chromatography ($SiO_2$, $CH_2Cl_2$/MeOH=95/5) to afford the amide as a yellow liquid (60.0 mg, 30%). $^1$H NMR (300 MHz, $CDCl_3$) δ 7.22-7.03 (m, 4H), 6.28 (br s, 0.5H, 6.22 (br s, 0.5H), 4.11 (td, 1H), 3.83-3.70 (m, 1H), 3.44 (ddd, 0.5H), 3.34 (ddd, 0.5H), 3.22-3.00 (m, 2H), 2.88-2.69 (m, 2H), 2.25 (tt, 0.5H), 2.02 (tt, 0.5H), 1.91-1.61 (m, overlapped with br s at 1.72, 2H), 1.58-1.04 (m, 9H), 0.96-0.78 (m, 3H); MS (ESI) m/z 301.2 (M+H).

Example 41

2-Methyl-N-(1,2,3,4-tetrahydro-1-isoquinolinylmethyl)cyclohexanecarboxamide

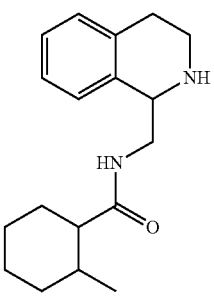

Compound 41

The reaction of 1-(1,2,3,4-tetrahydro-1-isoquinolinyl)methanamine 4 (0.100 g, 0.620 mmol) with 2-methylcyclohaxanecarbonyl chloride (0.100 mL, 0.650 mmol) was performed by following procedure A. The crude product was purified by flash column chromatography ($SiO_2$, $CH_2Cl_2$/MeOH=94/6) to afford the amide as a yellow solid (90.0 mg, 50%). $^1$H NMR (300 MHz, $CDCl_3$) δ 7.23-7.05 (m, 4H), 6.22 (br s, 1H), 4.15 (d, 1H), 3.85-3.70 (m, 1H), 3.52-3.34 (m, 1H), 3.24-2.98 (m, 2H), 2.90-2.69 (m, 2H), 2.34-1.99 (m, 1H), 1.93-1.11 (m, overlapped with br sat 1.63, 8H), 1.02-0.68 (m, 4H); MS (ESI) m/z 287.2 (M+H).

Example 42

4-Methoxy-N-(1,2,3,4-tetrahydro-1-isoquinolinylmethyl)cyclohexanecarboxamide

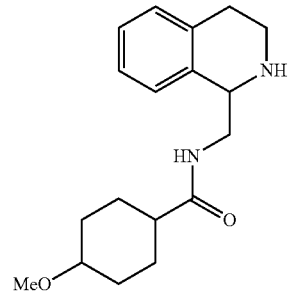

Compound 42

The reaction of 1-(1,2,3,4-tetrahydro-1-isoquinolinyl)methanamine 4 (0.100 g, 0.620 mmol) with 4-methoxycyclohaxanecarbonyl chloride (0.100 mL, 0.650 mmol) was performed by following procedure A. The crude product was purified by flash column chromatography ($SiO_2$, $CH_2Cl_2$/MeOH=92/8) to afford the amide as a yellow liquid (40.0 mg, 19%). $^1$H NMR (300 MHz, $CDCl_3$) δ 7.21-7.06 (m, 4H), 6.39 (br s, 1H), 4.15 (dd, 1H), 3.79 (ddd, 1H), 3.40 (ddd, 1H), 3.34 (s, 3H), 3.23-3.02 (m, 3H), 2.91-2.72 (m, 2H), 2.15-1.66 (m, overlapped with br s at 1.86, 5H), 1.57-1.37 (m, 2H), 1.30-1.09 (m, 2H); MS (ESI) m/z 303.1 (M+H).

Example 43

N-(1,2,3,4-Tetrahydro-1-isoquinolinylmethyl)cyclopentanecarboxamide

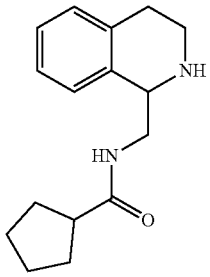

Compound 43

The reaction of 1-(1,2,3,4-tetrahydro-1-isoquinolinyl)methanamine 4 (0.580 g, 3.59 mmol) with cyclopentanecarbonyl chloride (0.460 mL, 3.76 mmol) was performed by following procedure A. The crude product was purified by flash column chromatography (SiO$_2$, CH$_2$Cl$_2$/MeOH=95/5) to afford the amide as a yellow liquid (0.400 g, 43%). $^1$H NMR (300 MHz, CDCl$_3$) δ 7.23-7.05 (m, 4H), 6.29 (br s, 1H), 4.12 (dd, 1H), 3.79 (ddd, 1H), 3.37 (ddd, 1H), 3.22-3.11 (m, 1H), 3.09-2.99 (m, 1H), 2.87-2.70 (m, 2H), 2.52 (quin, 1H), 2.27-1.44 (m, overlapped with br s at 1.97, 8H); MS (ESI) m/z 259.1 (M+H).

Example 44

N-(1,2,3,4-Tetrahydro-1-isoquinolinylmethyl)cyclobutanecarboxamide

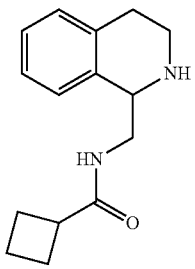

Compound 44

The reaction of 1-(1,2,3,4-tetrahydro-1-isoquinolinyl)methanamine 4 (0.100 g, 0.640 mmol) with cyclobutanecarbonyl chloride (80.0 μL, 0.670 mmol) was performed by following procedure A. The crude product was purified by flash column chromatography (SiO$_2$, CH$_2$Cl$_2$/MeOH=94/6) to afford the amide as a yellow liquid (80.0 mg, 53%). $^1$H NMR (300 MHz, CDCl$_3$) δ 7.23-7.04 (m, 4H), 6.27 (br s, 1H), 4.09 (d, 1H), 3.84-3.72 (m, 1H), 3.40-3.27 (m, 1H), 3.20-2.92 (m, 3H), 2.85-2.68 (m, 2H), 2.33-1.74 (m, 6H); MS (ESI) m/z 245.1 (M+H).

Example 45

N-(1,2,3,4-Tetrahydro-1-isoquinolinylmethyl)benzamide

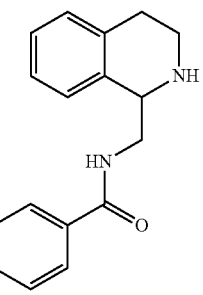

Compound 45

The reaction of 1-(1,2,3,4-tetrahydro-1-isoquinolinyl)methanamine 4 (0.100 g, 0.620 mmol) with benzoyl chloride (80.0 μL, 0.650 mmol) was performed by following procedure A. The crude product was purified by flash column chromatography (SiO$_2$, CH$_2$Cl$_2$/MeOH=94/6) to afford the amide as a yellow solid (70.0 mg, 40%). $^1$H NMR (400 MHz, CDCl$_3$) δ 7.80-7.77 (m, 2H), 7.52-7.38 (m, 3H), 7.26-7.24 (m, overlapped with s at 7.26, 1H), 7.22-7.13 (m, 2H), 7.13-7.02 (m, overlapped with br s at 7.07, 2H), 4.20 (dd, 1H), 4.02 (ddd, 1H), 3.49 (ddd, 1H), 3.21-3.13 (m, 1H), 3.11-3.04 (m, 1H), 2.86-2.72 (m, 2H); MS (ESI) m/z 267.1 (M+H).

Example 46

4-Methoxy-N-(1,2,3,4-tetrahydro-1-isoquinolinylmethyl)benzamide

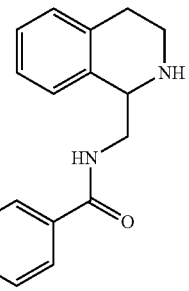

Compound 46

The reaction of 1-(1,2,3,4-tetrahydro-1-isoquinolinyl)methanamine 4 (0.100 g, 0.620 mmol) with 4-methoxybenzoyl chloride (90.0 μL, 0.650 mmol) was performed by following procedure A. The crude product was purified by flash column chromatography (SiO$_2$, CH$_2$Cl$_2$/MeOH=92/8) to afford the amide as a yellow liquid (90.0 mg, 48%). $^1$H NMR (400 MHz, CDCl$_3$) δ 7.78 (d, 2H), 7.28-7.23 (m, overlapped with s at 7.26, 1H), 7.22-7.08 (m, 4H), 6.92-6.90 (d, 2H), 4.26 (dd, 1H), 4.03 (ddd, 1H), 3.84 (s, 3H), 3.51 (ddd, 1H), 3.25-3.16 (m, 1H), 3.13-3.05 (m, 1H), 2.89-2.76 (m, 2H); MS (ESI) m/z 297.1 (M+H).

Example 47

N-(1,2,3,4-Tetrahydro-1-isoquinolinylmethyl)-4-(trifluoromethoxy)benzamide

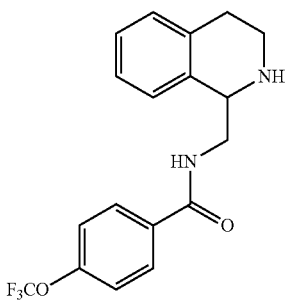

Compound 47

The reaction of 1-(1,2,3,4-tetrahydro-1-isoquinolinyl) methanamine 4 (0.100 g, 0.620 mmol) with 4-trifluoromethoxybenzoyl chloride (0.100 mL, 0.650 mmol) was performed by following procedure A. The crude product was purified by flash column chromatography (SiO$_2$, CH$_2$Cl$_2$/MeOH=94/6) to afford the amide as a yellow solid (60.0 mg, 28%). $^1$H NMR (400 MHz, CDCl$_3$) δ 7.82 (d, 2H), 7.32-7.09 (m, overlapped with s at 7.26, 6H), 7.00 (br s, 1H), 4.17 (dd, 1H), 4.00 (ddd, 1H), 3.48 (ddd. 1H), 3.20-3.04 (m, 2H), 2.87-2.73 (m, 2H); MS (ESI) m/z 351.1 (M+H).

Example 48

4-Fluoro-N-(1,2,3,4-tetrahydro-1-isoquinolinylmethyl)benzamide

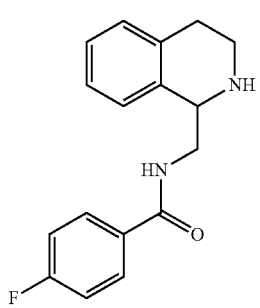

Compound 48

The reaction of 1-(1,2,3,4-tetrahydro-1-isoquinolinyl) methanamine 4 (0.100 g, 0.620 mmol) with 4-fluorobenzoyl chloride (80.0 µL, 0.650 mmol) was performed by following procedure A. The crude product was purified by flash column chromatography (SiO$_2$, CH$_2$Cl$_2$/MeOH=93/7) to afford the amide as a yellow solid (80.0 mg, 47%). $^1$H NMR (300 MHz, CDCl$_3$) δ 7.79 (dd, 2H), 7.24-7.07 (m, 6H), 6.99 (br s, 1H), 4.19 (dd, 1H), 4.01 (ddd, 1H), 3.48 (ddd, 1H), 3.22-3.04 (m, 2H), 2.82-2.78 (m, 2H); MS (ESI) m/z 285.1 (M+H).

Example 49

4-Chloro-N-(1,2,3,4-tetrahydro-1-isoquinolinylmethyl)benzamide

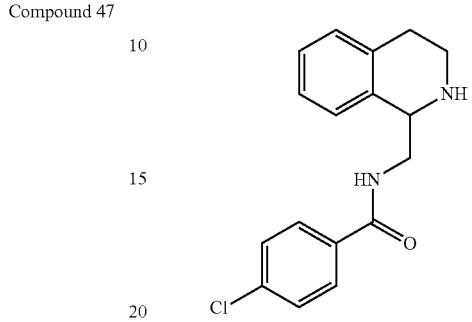

Compound 49

The reaction of 1-(1,2,3,4-tetrahydro-1-isoquinolinyl) methanamine 4 (0.100 g, 0.620 mmol) with 4-chlorobenzoyl chloride (80.0 µL, 0.650 mmol) was performed by following procedure A. The crude product was purified by flash column chromatography (SiO$_2$, CH$_2$Cl$_2$/MeOH=93/7) to afford the amide as a yellow liquid (30.0 mg, 16%). $^1$H NMR (300 MHz, CDCl$_3$) δ 7.75 (d, 2H), 7.38 (d, 2H), 7.29-7.07 (m, overlapped with s at 7.26, 5H), 4.25 (dd, 1H), 4.02 (ddd, 1H), 3.52 (ddd, 1H), 3.25-3.05 (m, 2H), 2.89-2.74 (m, 2H); MS (ESI) m/z 301.1 (M+H).

Example 50

4-Ethyl-N-(1,2,3,4-tetrahydro-1-isoquinolinylmethyl)benzamide

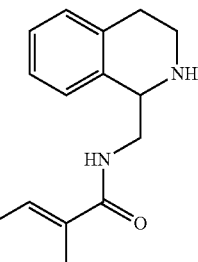

Compound 50

The reaction of 1-(1,2,3,4-tetrahydro-1-isoquinolinyl) methanamine 4 (0.200 g, 1.23 mmol) with 4-ethylbezoyl chloride (0.220 mL, 1.48 mmol) was performed by following procedure A. The crude product was purified by flash column chromatography (SiO$_2$, CH$_2$Cl$_2$/MeOH=96/4) to afford the amide as a yellow solid (0.170 g, 48%). $^1$H NMR (300 MHz, CDCl$_3$) δ 7.71 (d, 2H), 7.31-7.08 (m, overlapped with s at 7.26, 6H), 6.98 (br s, 1H), 4.19 (dd, 1H), 4.03 (ddd, 1H), 3.48 (ddd, 1H), 3.23-3.02 (m, 2H), 2.87-2.75 (m, 2H), 2.69 (q, 2H), 1.24 (t, 3H); MS (ESI) m/z 295.1 (M+H).

Example 51

3-Methoxy-N-(1,2,3,4-tetrahydro-1-isoquinolinylmethyl)benzamide

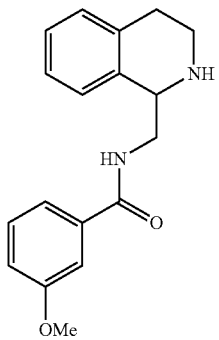

Compound 51

The reaction of 1-(1,2,3,4-tetrahydro-1-isoquinolinyl) methanamine 4 (0.100 g, 0.620 mmol) with 3-methoxybenzoyl chloride (90.0 µL, 0.650 mmol) was performed by following procedure A. The crude product was purified by flash column chromatography (SiO$_2$, CH$_2$Cl$_2$/MeOH=94/6) to afford the amide as a yellow liquid (60.0 mg, 32%). $^1$H NMR (400 MHz, CDCl$_3$) δ 7.37 (d, 1H), 7.35-6.99 (m, overlapped with s at 7.26, 8H), 4.21 (dd, 1H), 4.02 (ddd, 1H), 3.84 (s, 3H), 3.50 (ddd, 1H), 3.22-3.03 (m, 2H), 2.87-2.74 (m, 2H); MS (ESI) m/z 297.1 (M+H).

Example 52

3-Fluoro-N-(1,2,3,4-tetrahydro-1-isoquinolinylmethyl)benzamide

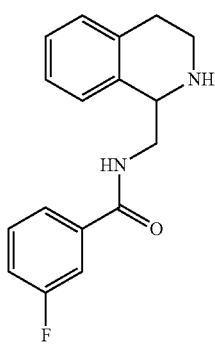

Compound 52

The reaction of 1-(1,2,3,4-tetrahydro-1-isoquinolinyl) methanamine 4 (0.100 g, 0.620 mmol) with 3-fluorobenzoyl chloride (80.0 µL, 0.650 mmol) was performed by following procedure A. The crude product was purified by flash column chromatography (SiO$_2$, CH$_2$Cl$_2$/MeOH=94/6) to afford the amide as a yellow liquid (60.0 mg, 37%). $^1$H NMR (300 MHz, CDCl$_3$) δ 7.54-7.48 (m, 2H), 7.43-7.36 (m, 1H), 7.24-7.10 (m, 5H), 7.02 (br s, 1H), 4.18 (dd, 1H), 4.01 (ddd, 1H), 3.48 (ddd, 1H), 3.21-3.04 (m, 2H), 2.82-2.78 (m, 2H); MS (ESI) m/z 285.1 (M+H).

Example 53

3-Chloro-N-(1,2,3,4-tetrahydro-1-isoquinolinylmethyl)benzamide

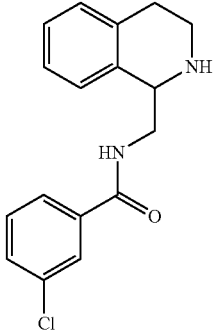

Compound 53

The reaction of 1-(1,2,3,4-tetrahydro-1-isoquinolinyl) methanamine 4 (0.100 g, 0.620 mmol) with 3-chlorobenzoyl chloride (80.0 µL, 0.650 mmol) was performed by following procedure A. The crude product was purified by flash column chromatography (SiO$_2$, CH$_2$Cl$_2$/MeOH=95/5) to afford the amide as a yellow solid (60.0 mg, 31%). $^1$H NMR (300 MHz, CDCl$_3$) δ 7.80 (t, 1H), 7.67 (dt, 1H), 7.45 (dt, 1H), 7.35 (t, 1H), 7.29-7.08 (m, overlapped with s at 7.26, 5H), 4.25 (dd, 1H), 4.03 (ddd, 1H), 3.52 (ddd, 1H), 3.25-3.06 (m, 2H), 2.90-2.74 (m, 2H); MS (ESI) m/z 301.1 (M+H).

Example 54

3-Methyl-N-(1,2,3,4-tetrahydro-1-isoquinolinylmethyl)benzamide

Compound 54

The reaction of 1-(1,2,3,4-tetrahydro-1-isoquinolinyl) methanamine 4 (0.100 g, 0.620 mmol) with m-toluoyl chloride (90.0 µL, 0.650 mmol) was performed by following procedure A. The crude product was purified by flash column chromatography (SiO$_2$, CH$_2$Cl$_2$/MeOH=94/6) to afford the amide as a yellow liquid (70.0 mg, 40%). $^1$H NMR (300 MHz, CDCl$_3$) δ 7.62 (s, 1H), 7.57 (t, 1H), 7.33-7.04 (m, overlapped with s at 7.26, 7H), 4.23 (dd, 1H), 4.03 (ddd, 1H), 3.50 (ddd, 1H), 3.25-3.02 (m, 2H), 2.90-2.73 (m, 2H), 2.34 (s, 3H); MS (ESI) m/z 281.1 (M+H).

Example 55

2-Methoxy-N-(1,2,3,4-tetrahydro-1-isoquinolinylmethyl)benzamide

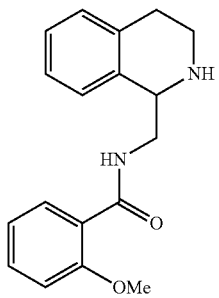

Compound 55

The reaction of 1-(1,2,3,4-tetrahydro-1-isoquinolinyl)methanamine 4 (0.100 g, 0.620 mmol) with 2-methoxybenzoyl chloride (90.0 μL, 0.650 mmol) was performed by following procedure A. The crude product was purified by flash column chromatography ($SiO_2$, $CH_2Cl_2$/MeOH=94/6) to afford the amide as a yellow liquid (90.0 mg, 50%). $^1$H NMR (300 MHz, $CDCl_3$) δ 8.31 (br s, 1H), 8.17 (dd, 1H), 7.42 (td, 1H), 7.30-7.26 (m, 1H), 7.24-7.09 (m, 3H), 7.05 (t, 1H), 6.92 (d, 1H), 4.33 (dd, 1H), 4.07 (ddd, 1H), 3.83 (s, 3H), 3.63 (ddd, 1H), 3.32-3.22 (m, 1H), 3.12-3.01 (m, 1H), 2.93-2.73 (m, 2H); MS (ESI) m/z 297.1 (M+H).

Example 56

N-(1,2,3,4-Tetrahydro-1-isoquinolinylmethyl)-2-(trifluoromethoxy)benzamide

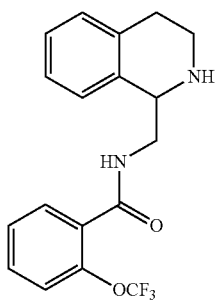

Compound 56

The reaction of 1-(1,2,3,4-tetrahydro-1-isoquinolinyl)methanamine 4 (0.100 g, 0.620 mmol) with 2-trifluoromethoxybenzoyl chloride (0.100 mL, 0.650 mmol) was performed by following procedure A. The crude product was purified by flash column chromatography ($SiO_2$, $CH_2Cl_2$/MeOH=96/4) to afford the amide as a yellow solid (80.0 mg, 37%). $^1$H NMR (300 MHz, $CDCl_3$) δ 7.96 (dd, 1H), 7.48 (td, 1H), 7.42-7.31 (m, 2H), 7.31-7.07 (m, 5H), 4.17 (dd, 1H), 4.05 (ddd, 1H), 3.50 (ddd, 1H), 3.25-3.02 (m, 2H), 2.85-2.71 (m, 2H); MS (ESI) m/z 351.1 (M+H).

Example 57

2-Fluoro-N-(1,2,3,4-tetrahydro-1-isoquinolinylmethyl)benzamide

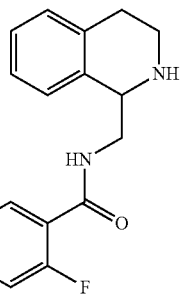

Compound 57

The reaction of 1-(1,2,3,4-tetrahydro-1-isoquinolinyl)methanamine 4 (0.100 g, 0.620 mmol) with 2-fluorobenzoyl chloride (80.0 μL, 0.650 mmol) was performed by following procedure A. The crude product was purified by flash column chromatography ($SiO_2$, $CH_2Cl_2$/MeOH=95/5) to afford the amide as a yellow solid (70.0 mg, 41%). $^1$H NMR (400 MHz, $CDCl_3$) δ 8.07 (td, 1H), 7.48-7.42 (m, 2H), 7.26-7.07 (m, overlapped with s at 7.26, 6H), 4.23 (dd, 1H), 4.04 (ddd, 1H), 3.56 (ddd, 1H), 3.20 (ddd, 1H), 3.07 (dt, 1H), 2.87-2.74 (m, 2H); MS (ESI) m/z 285.1 (M+H).

Example 58

3,4-Dimethyl-N-(1,2,3,4-tetrahydro-1-isoquinolinylmethyl)benzamide

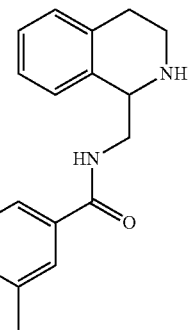

Compound 58

The reaction of 1-(1,2,3,4-tetrahydro-1-isoquinolinyl)methanamine 4 (0.100 g, 0.620 mmol) with 3,4-dimethylbezoyl chloride (0.100 mL, 0.650 mmol) was performed by following procedure A. The crude product was purified by flash column chromatography ($SiO_2$, $CH_2Cl_2$/MeOH=95/5) to afford the amide as a yellow solid (0.100 g, 56%). $^1$H NMR (300 MHz, $CDCl_3$) δ 7.59 (s, 1H), 7.51 (d, 1H), 7.29-7.06 (m, overlapped with s at 7.26, 6H), 4.23 (dd, 1H), 4.01 (ddd, 1H), 3.49 (ddd, 1H), 3.25-3.02 (m, 2H), 2.89-2.74 (m, 2H), 2.28 (s, 6H); MS (ESI) m/z 295.1 (M+H).

Example 59

3,4-Dichloro-N-(1,2,3,4-tetrahydro-1-isoquinolinyl-methyl)benzamide

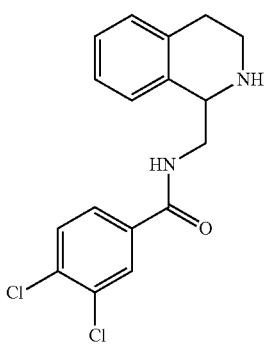

Compound 59

The reaction of 1-(1,2,3,4-tetrahydro-1-isoquinolinyl) methanamine 4 (1.90 g, 6.16 mmol) with 3,4-dichlorobenzoyl chloride (1.55 g, 7.40 mmol) was performed by following procedure A. The crude product was purified by flash column chromatography (SiO$_2$, CH$_2$Cl$_2$/MeOH=96/4) to afford the amide as a yellow solid (1.01 g, 49%). $^1$H NMR (300 MHz, CDCl$_3$) δ 7.89 (d, 1H), 7.61 (dd, 1H), 7.48 (d, 1H), 7.25-7.08 (m, 5H), 4.19 (dd, 1H), 3.99 (ddd, 1H), 3.47 (ddd, 1H), 3.22-3.03 (m, 2H), 2.87-2.75 (m, 2H); MS (ESI) m/z 335.0 (M+H).

Example 60

2,4-Dimethyl-N-(1,2,3,4-tetrahydro-1-isoquinolinyl-methyl)benzamide

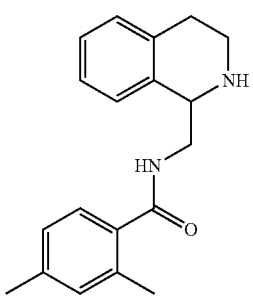

Compound 60

The reaction of 1-(1,2,3,4-tetrahydro-1-isoquinolinyl) methanamine 4 (0.100 g, 0.620 mmol) with 2,4-dimethylbezoyl chloride (0.100 mL, 0.650 mmol) was performed by following procedure A. The crude product was purified by flash column chromatography (SiO$_2$, CH$_2$Cl$_2$/MeOH=95/5) to afford the amide as a yellow solid (80.0 mg, 46%). $^1$H NMR (300 MHz, CDCl$_3$) δ 7.31-7.07 (m, overlapped with s at 7.26, 5H), 7.03-6.93 (m, 2H), 6.65 (br t, 1H), 4.25 (dd, 1H), 3.91 (ddd, 1H), 3.64 (ddd, 1H), 3.23-3.10 (m, 1H), 3.08-2.95 (m, 1H), 2.89-2.69 (m, 2H), 2.33 (s, 3H), 2.30 (s, 3H); MS (ESI) m/z 295.1 (M+H).

The procedure for preparing Compound 61 below ("procedure F") was followed to synthesize Compounds 62-67.

Example 61

4-Methyl-N-[(2-methyl-1,2,3,4-tetrahydro-1-isoquinolinyl)methyl]benzamide

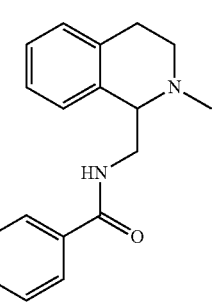

Compound 61

To a solution of 4-methyl-N-(1,2,3,4-tetrahydro-1-isoquinolinylmethyl)benzamide 38 (0.100 g, 0.360 mmol) in CH$_3$CN (5.1 mL) was added formaldehyde (90.0 µL, 1.25 mmol) and NaBH(OAc)$_3$ (0.300 g, 1.43 mmol). The solution was stirred at room temperature for 7 h and then concentrated under reduced pressure. The residue was dissolved in 30 mL of CH$_2$Cl$_2$ and washed with NaHCO$_{3(aq)}$ (2×10 mL). The organic layer was dried over MgSO$_4$ and the solvent was evaporated under reduced pressure. The crude product was purified by flash column chromatography (SiO$_2$, CH$_2$Cl$_2$/MeOH=97/3) to afford the tertiary amines as a yellow liquid (90.0 mg, 85%). $^1$H NMR (400 MHz, CDCl$_3$) δ 7.61 (dd, 2H), 7.25-7.08 (m, 6H), 6.91 (br s, 1H), 3.91 (ddd, 1H), 3.71 (dd, 1H), 3.62 (ddd, 1H), 3.21-3.11 (m, 1H), 2.95-2.85 (m, 1H), 2.81-2.72 (m, 2H), 2.53 (s, 3H), 2.37 (s, 3H); MS (ESI) m/z 295.1 (M+H).

Example 62

N-[(2-Butyl-1,2,3,4-tetrahydro-1-isoquinolinyl)methyl]-4-methylbenzamide

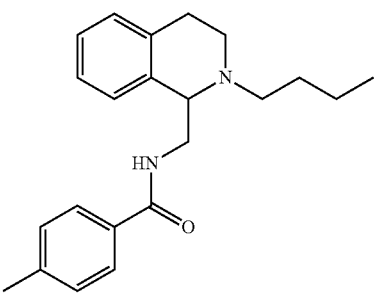

Compound 62

The reaction of 4-methyl-N-(1,2,3,4-tetrahydro-1-isoquinolinylmethyl)benzamide 38 (0.100 g, 0.360 mmol) with butyraldehyde (0.110 mL, 1.25 mmol) was performed by following procedure F. The crude product was purified by flash column chromatography (SiO$_2$, CH$_2$Cl$_2$/MeOH=98/2) to afford the tertiary amines as a yellow solid (80.0 mg, 66%). $^1$H NMR (400 MHz, CDCl$_3$) δ 7.68 (d, 2H), 7.25-6.98 (m, 7H), 3.98 (ddd, 1H), 3.81 (dd, 1H), 3.32 (ddd, 1H), 3.22

(ddd, 1H), 3.02-2.86 (m, 2H), 2.72-2.50 (m, 3H), 2.40 (s, 3H), 1.61-1.44 (m, 2H), 1.37 (sextet, 2H), 0.90 (t, 3H); MS (ESI) m/z 337.2 (M+H).

Example 63

4-Methyl-N-{[2-(2-methylpropyl)-1,2,3,4-tetrahydro-1-isoquinolinyl]methyl}benzamide

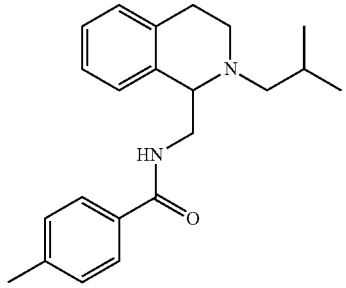

Compound 63

The reaction of 4-methyl-N-(1,2,3,4-tetrahydro-1-isoquinolinylmethyl)benzamide 38 (0.100 g, 0.360 mmol) with isobutyraldehyde (0.110 mL, 1.25 mmol) was performed by following procedure F. The crude product was purified by flash column chromatography (SiO$_2$, CH$_2$Cl$_2$/MeOH=99/1) to afford the tertiary amines as a yellow liquid (80.0 mg, 69%). $^1$H NMR (300 MHz, CDCl$_3$) δ 7.67 (d, 2H), 7.25-7.00 (m, 7H), 4.01-3.92 (m, 1H), 3.75 (dd, 1H), 3.39-3.16 (m, 2H), 3.04-2.80 (m, 2H), 2.61-2.30 (m, overlapped with s at 2.41, 6H), 1.83 (heptet, 1H), 0.96 (d, 3H), 0.92 (d, 3H); MS (ESI) m/z 337.2 (M+H).

Example 64

N-{[2-(2-Chloroethyl)-1,2,3,4-tetrahydro-1-isoquinolinyl]methyl}-4-methylbenzamide

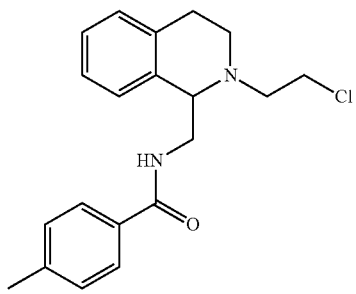

Compound 64

The reaction of 4-methyl-N-(1,2,3,4-tetrahydro-1-isoquinolinylmethyl)benzamide 38 (0.100 g, 0.360 mmol) with chloroacetaldehyde (0.160 mL, 1.25 mmol) was performed by following procedure F. The crude product was purified by flash column chromatography (SiO$_2$, CH$_2$Cl$_2$/MeOH=98/2) to afford the tertiary amines as a yellow solid (50.0 mg, 37%). $^1$H NMR (300 MHz, CDCl$_3$) δ 7.68 (d, 2H), 7.33-7.09 (m, overlapped with s at 7.26, 6H), 6.79 (br s, 1H), 4.08-3.96 (m, 1H), 3.94-3.85 (m, 1H), 3.70 (t, 2H), 3.48-3.25 (m, 2H), 3.01-2.78 (m, 4H), 2.68-2.54 (m, 1H), 2.38 (s, 3H).

Example 65

4-Ethyl-N-[(2-methyl-1,2,3,4-tetrahydro-1-isoquinolinyl)methyl]benzamide

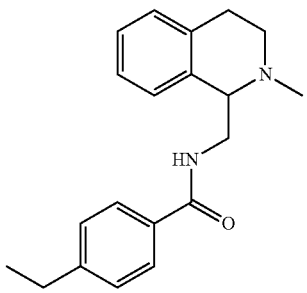

Compound 65

The reaction of 4-ethyl-N-(1,2,3,4-tetrahydro-1-isoquinolinylmethyl)benzamide 50 (0.170 g, 0.590 mmol) with formaldehyde (0.150 mL, 2.05 mmol) was performed by following procedure F. The crude product was purified by flash column chromatography (SiO$_2$, CH$_2$Cl$_2$/MeOH=97/3) to afford the tertiary amines as a yellow liquid (0.170 g, 96%). $^1$H NMR (300 MHz, CDCl$_3$) δ 7.62 (d, 2H), 7.32-7.07 (m, overlapped with s at 7.26, 6H), 6.86 (br s, 1H), 3.91 (dt, 1H), 3.73-3.55 (m, 2H), 3.22-3.08 (m, 1H), 2.97-2.83 (m, 1H), 2.82-2.73 (m, 2H), 2.67 (q, 2H), 2.52 (s, 3H), 1.23 (t, 3H); MS (ESI) m/z 309.1 (M+H).

Example 66

3,4-Dimethyl-N-[(2-methyl-1,2,3,4-tetrahydro-1-isoquinolinyl)methyl]benzamide

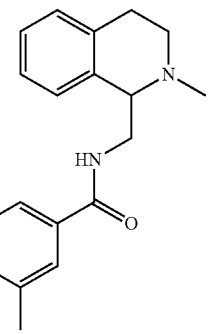

Compound 66

The reaction of 3,4-dimethyl-N-(1,2,3,4-tetrahydro-1-isoquinolinylmethyl)benzamide 58 (0.100 g, 0.340 mmol) with formaldehyde (90.0 µL, 1.19 mmol) was performed by following procedure F to afford the tertiary amines as a yellow solid (0.100 g, 91%). $^1$H NMR (300 MHz, CDCl$_3$) δ 7.50 (s, 1H), 7.40 (dd, 1H), 7.29-7.05 (m, overlapped with s at 7.26, 5H), 6.84 (br s, 1H), 3.91 (ddd, 1H), 3.74-3.67 (m, 1H), 3.65-3.55 (m, 1H), 3.22-3.10 (m, 1H), 2.97-2.83 (m, 1H), 2.83-2.69 (m, 2H), 2.53 (s, 3H), 2.28 (s, 6H); MS (ESI) m/z 309.1 (M+H).

Example 67

3,4-Dichloro-N-[(2-methyl-1,2,3,4-tetrahydro-1-isoquinolinyl)methyl]benzamide

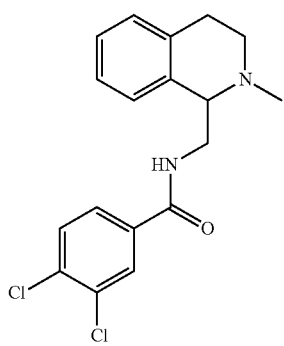 [SMILES: CN1CCc2ccccc2C1CNC(=O)c1ccc(Cl)c(Cl)c1]

Compound 67

The reaction of 3,4-dichloro-N-(1,2,3,4-tetrahydro-1-isoquinolinylmethyl)benzamide 59 (0.100 g, 0.300 mmol) with formaldehyde (80.0 μL, 1.04 mmol) was performed by following procedure F to afford the tertiary amines as a yellow solid (90.0 mg, 90%). $^1$H NMR (300 MHz, CDCl$_3$) δ 7.78 (d, 1H), 7.55-7.42 (m, 2H), 7.24-7.09 (m, 4H), 6.89 (br t, 1H), 3.89 (ddd, 1H), 3.73-3.56 (m, 2H), 3.22-3.08 (m, 1H), 2.97-2.84 (m, 1H), 2.83-2.70 (m, 2H), 2.53 (s, 3H); MS (ESI) m/z 349.0 (M+H).

Example 68

Animals

Male wild-type C57BL/6 (B6) mice (25-30 g) and mu-opioid receptor-knockout mice (provided by National Health Research Institutes, Taiwan) were randomized to an study group. Animal protocols were approved by the Institutional Animal Care and Use Committee of the National Health Research Institutes, Taiwan. All Animal studies were conducted in accordance with the Policies on the Use of Animals in Neuroscience Research and the ethical guidelines for investigations of pain in conscious animals established by the International Association for the Study of Pain. Animals were kept in a temperature-controlled animal room with a 12:12 h light-dark cycle.

Materials

Morphine hydrochloride was obtained from the Food and Drug Administration, Ministry of Health and Welfare, Taipei, Taiwan. [$^3$H]diprenorphine and [$^3$H]nociceptin was obtained from PerkinElmer Inc., Boston, Mass., USA. [Met5]enkephalin (Met-5) and oxaliplatin was obtained from Sigma Chemical Co., St. Louis, Mo., USA. Orphanin FQ, cyprodime, and were obtained from Tocris Biosciences, Bristol, UK. BANORL24 were obtained from Abcam; Cambridge, Mass., USA.

FLIPR® Calcium Assay

One day before the assay, CORNING® black with clear flat bottom 96-well assay plates were coated with a 0.1 mg/mL Poly-L-Lysine solution. CHO-K1/MOR/Ga15 cells were suspended in the F12 medium and plated at a density of about 8×10$^4$ cells/well in 200 pt medium. Cells were incubated in a humidified atmosphere of 10% CO$_2$ at 37° C. overnight so as to reach an 80-90% confluent cell monolayer before the assay. On the day of the assay, 150 μL medium/well was removed from plate. To each well, 50 μL FLIPR® calcium assay reagent dissolved in 1× assay buffer (Hank's buffered salt solution or HBSS: KCl 5 mM, KH$_2$PO$_4$ 0.3 mM, NaCl 138 mM, NaHCO$_3$ 4 mM, Na$_2$HPO$_4$ 0.3 mM, d-glucose 5.6 mM, with additional 20 mM HEPES and 13 mM CaCl$_2$, pH 7.4), with 2.5 mM probenecid was added and the plate was incubated at 37° C. for 1 h. Compounds and other reagents were dissolved in the assay buffer. Using a FlexStationlll (Molecular Devices Corp.), the [Ca$^{2+}$]$_i$ fluorescence increased after robotic injections of compounds or other reagents were monitored every 1.52 s interval with an excitation wavelength at 485 nm and with an emission wavelength at 525 nm. The [Ca$^{2+}$]$_i$ fluorescence was measured up to 90 s after agonist injection. The fluorescence intensity from 6 to 12 wells of cells were averaged and the relative amount of [Ca$^{2+}$]$_i$ release was determined by integrating the AUC of the [Ca$^{2+}$]$_i$ fluorescence averages.

Among the tested compounds, Compounds 5-13, 8, 15, 17-21, 24-29, 35-40, and 42-67 each showed an EC$_{50}$ less than 10 μM; and Compounds 5-7, 9-13, 15-18, 20, 21, 24-29, 35, 36, 38-43, 45-54, and 56-67 each showed an AUC higher than 5000.

Cyclic Adenosine Monophosphate (cAMP) Assay

Human embryonic kidney 293 cells expressing human mu-opioid receptor were cultured in high-glucose Dulbecco's modified Eagle medium (DMEM, GIBCO) supplemented with 10% fetal bovine serum, 100 units/mL penicillin, 100 μg/mL streptomycin, 400 μg/mL G418, and 2 mM L-glutamine in T-175 tissue culture flasks and harvested with trypsin/ethylenediaminetetraacetic acid (EDTA) solution (GIBCO). Chinese hamster ovary cells expressing human NOP receptor were cultured in F12 medium (GIBCO) containing 10% fetal bovine serum, 100 units/mL penicillin, 100 g/mL streptomycin, 200 g/mL G418, and 20 g/mL Hygromycin B in T-175 tissue culture flasks and harvested with Cell Detachment Reagent (DiscoveRx). Cells (72,000 per well) were plated in 100 μl/well of DMEM in 96-well solid-bottom white plates (GIBCO) and 50 μl/well of drug in HBSS in the presence of forskolin and 3-isobutyl-1-methylxanthine at final concentrations of 1 μM and 500 μM, respectively. After 30 min of incubation at room temperature, the concentration of cyclic adenosine monophosphate was determined using a LANCE Ultra cAMP Assay kit (PerkinElmer). Two hours later, plate fluorescence was measured using a Victor 2 plate reader with excitation at 330 nm and emission at 615 nm and 665 nm.

Internalization Assay

MOR internalization was measured by an enzyme complementation assay in human osteosarcoma U2OS cells expressing human MOR (U2OS-MOR). Note that U2OS cells express human MOR with complementary pieces of β-galactosidase that are genetically fused to the receptor and to a component of the endocytic vesicle. When activated, MOR then interacts with the endosomes in this study and the 2 fusion proteins form a complete enzyme whose activity can be detected by chemiluminescence.

The PathHunter G protein-coupled receptor internalization assay (DiscoveRx, Fremont, Calif., USA) was performed according to the manufacturer's protocol. Cells were grown to confluence in McCoy's 5A medium (GIBCO, Waltham, Mass., USA) containing 10% fetal bovine serum, 100 units/mL penicillin, 100 μg/mL streptomycin, 20 μg/mL G418 (Sigma), 5 μg/mL Hygromycin B (InvivoGen, San Diego, Calif., USA), and 25 mM HEPES in T-175 tissue culture flasks (Corning, Corning, N.Y., USA) and harvested with Cell Detachment Reagent (DiscoveRx). Cells (5,000 per well) were then seeded in black 384-well assay plates (Corning) with a CP5 reagent (DiscoveRx) and incubated for 24 h before running the assay. After each treatment, cells were incubated at room temperature for 1.5 h, followed by the addition of 8 μl of the PathHunter Detection kit (DiscoveRx) for 1 h, and analyzed for chemiluminescence on a Victor 2 plate reader (PerkinElmer, Waltham, Mass., USA). Studies were performed on the same day, using the same generation of cells to ensure accurate comparison of data.

β-Arrestin-2 Recruitment (β-Arrestin) Assay

The PathHunter G protein-coupled receptor β-arrestin-2 assay (DiscoveRx) was performed according to the manufacturer's protocol. Briefly, when β-arrestin-2 translocates to the active receptor, complementary β-galactosidase fragments fused to the receptor and β-arrestin-2 interact to form a functional enzyme, which can be detected by chemiluminescence.

Chinese hamster ovary cells expressing human MOR or human NOP receptor were grown to confluence in F12 medium (GIBCO) containing 10% fetal bovine serum, 100 units/mL penicillin, 100 μg/mL streptomycin, 200 μg/mL G418, and 20 μg/mL Hygromycin B in T-175 tissue culture flasks and harvested with Cell Detachment Reagent (DiscoveRx). Cells (5,000 per well) were then seeded in black 384-well assay plates with a CP2 reagent (DiscoveRx) and incubated for 24 h before running the assay. After each treatment, cells were incubated at room temperature for 1.5 h, followed by the addition of 8 μl of the PathHunter Detection reagent (DiscoveRx) and incubated for 1 h. Luminescence was detected using a Victor 2 plate reader. Studies were performed on the same day and the same passage of cells was used to ensure accurate comparisons of data.

Membrane Potential Assay

In a membrane potential assay, the activation of G-protein-coupled inwardly rectifying potassium (GIRK) channels was tested in myc-MOR expressing mouse pituitary AtT-20 cells. AtT-20 cells were cultured in DMEM containing 10% fetal bovine serum, 100 units/mL penicillin, and 100 μg/mL streptomycin in T-175 tissue culture flasks and harvested with a trypsin/EDTA solution. Cells (25,000 per well) were transiently transfected with myc-tagged human MOR plasmid (provided by Dr. Ping-Yee Law, University of Minnesota, USA) using NEPA21 electroporator gene transfection system (Nepa Gene, Ichikawa-City, Japan) and subsequently seeded in black 96-well clear, flat-bottomed assay plates (Corning). The poring pulse conditions for electroporation were as follows: 110 V, pulse length of 7.5 ms, inter-pulse intervals of 50 ms, and a 10% decay rate with plus polarity. The transfer pulse conditions were as follows: 20 V, 50-ms pulse length, 50-ms pulse interval, and a 40% decay rate with plus and minus polarities. After 24 h, cells were serum-starved for 3 h to detect potassium conductance changes using a fluorometric imaging plate reader (FLIPR) membrane potential assay according to the manufacturer's instructions (Molecular Devices, Sunnyvale, Calif., USA). Briefly, cells were treated with blue membrane potential dye for 0.5 h at 25° C. The fluorescence signal (excitation: 485 nm, emission: 525 nm) was monitored at intervals of 1.52 s, up to 150 s after the treatment on a FlexStation 3 bench-top multi-mode microplate reader (Molecular Devices).

Tail Flick Test

Drug-induced antinociception against acute thermal pain hypersensitivity was evaluated using the Tail-Flick Analgesia Meter (Columbia Instruments, Columbus, Ohio, USA). A basal latency was recorded before treatment and mice with the basal latency between 2.5-3.5 s were collected and randomly divided into each group. The tail-flick latencies were recorded at different time points after intravenous, intraperitoneal, subcutaneous, or oral administration of drugs. Morphine and naloxone were dissolved in saline. The subcutaneous and oral dosing solution of Compound 67 was prepared in 5% DMA, 5% solutol, 4.5% Captisol and 85.5% saline. Cyprodime and naloxone hydrochloride were prepared in 5% DMSO, and 95% saline. The solution of BANORL24 was prepared in saline. To avoid tissue damage, the cutoff time was 10 sec. The antinociceptive effect was defined as the difference between the tail-flick latency and the basal latency at each time point. The area under the curve (AUC) value was obtained by calculating the area under the time-response curve of the antinociceptive effect after treatment of the drugs. The percentage of the maximum possible effect (% of MPE) was calculated according to the following equation: % of MPE=[(tail-flick latency−basal latency)÷(cutoff time−basal latency)]×100. See, e.g., Mathews et al., the Journal of Neuroscience: the official journal of the Society for Neuroscience, 2008, 28:12183-12189.

Tail-Clip Test

Each B6 mouse was placed in an acrylic box (10 cm in diameter, 30 cm high) and allowed to acclimate for 5 min before testing, and then a clip was applied 1-cm from the base of the tail. The latency to bite or grasp the clip was measured during the clip was applied to the tail. See, e.g., Cao et al., Nature, 1998, 392:390-394. Regardless of the response to 20 s, a cut off time was set to avoid tissue damage.

Oxaliplatin- and Cancer-Induced Pain and Mechanical Allodynia Test

To induce neuropathic pain, each B6 mouse was intraperitoneally injected with either oxaliplatin (3.0 mg/kg), or vehicle (saline) after habituation to the test environment and baseline measurements of pain sensitivity. See, e.g., Ta et al., Molecular Pain, 2009, 5:9-9. For cancer pain model, mouse B16-F1 melanoma cells were cultured in DMEM containing 10% fetal bovine serum, 100 units/mL penicillin, and 100 μg/mL streptomycin in T-175 tissue culture flasks and harvested with trypsin/EDTA solution. To induce cancer pain, each B6 mouse was injected with either 20 μL phosphate-buffered saline or cells ($6\times10^5$ cells/20 μL phosphate-buffered saline) in the footpad of the right hind paw under isoflurane anesthesia on post-inoculation day 0. On post-inoculation day 19, i.e., the test day, mice were placed on a mesh floor with 5×5 mm holes, covered with a cup to prevent visual stimulation, and allowed to adapt for 1 h prior to testing. Melanoma cell-injected mice were intravenously administered vehicle, morphine, or Compound 67, and 50% withdrawal threshold was subsequently evaluated using a classical up-and-down method with von Frey filaments (range: 0.1-1 g; IITC Life Science). See, e.g., Chaplan et al., Journal of Neuroscience Methods, 1994, 53:55-63. The tests were initiated with 0.5 g force. Briefly, whenever a withdrawal response occurred, the next weaker von Frey filament was applied. On the other hand, whenever no withdrawal response occurred, the next stronger filament was applied. Mechanical allodynia was defined as changes in the amount of pressure to induce the hind paw withdrawal.

Colonic Transit Analysis

B6 mice were fasted for at least 16 h before the study with free access to water. In a charcoal meal test, various doses of drugs were administered to the mice 30 min prior to the administration of an aqueous activated charcoal suspension (10% activated charcoal+5% gum Arabic; 0.3 mL). After 30 min, the mice were euthanized by intraperitoneal administration of a ketamine/xylazine cocktail (Sigma) followed by cervical dislocation and the total length of migration of the charcoal meal was measured from the pylorus to the ileocecal junction of the small intestine. The length of the intestine from pylorus to the caecum and the distance traveled by the charcoal were measured. The migration index was expressed as percentage of the distance traveled by the peristaltic charcoal meal relative to the total length of the small intestine, calculated according to the following formula.

% of Gastrointestinal transit=Distance Travelled by Charcoal Meal/Full Length of the Small Intestine×100%

Gastrointestinal propulsion was calculated as the percentage of the distance travelled by the charcoal meal relative to the total length of the small intestine, to control for individual variations. The percentage inhibition relative to the control was also calculated as:

% Gastrointestinal Inhibition (GI)=(Control group−Drug-treated group)/Control group×100%

In bead expulsion test, mice were fasted as described above for the charcoal meal test. Mice were given a subcutaneous injection of saline, morphine (7.2 mg/kg) or Compound 67 (1.8 mg/kg). After 20 min, animals were anesthetized with isoflurane (1-2 min) in order to insert a single 2 mm glass bead into the distal colon at a distance of 3 cm from the anus. Mice were placed into individual cages and monitored the bead expulsion time. See, e.g., Ross et al., the Journal of Pharmacology and Experimental Therapeutics, 2008, 327:561-572.

Respiratory Function Test

The respiratory depression is the major side effect of most traditional opioids, such as acute morphine treatment. The respiratory analysis, including respiratory frequency and tidal volume was determined after mice are acutely or subchronically treated with morphine or Compound 67. Mice were habituated to the Buxco chamber for 15 min prior to drug injection and at the same time the respiratory activity was recorded for 5 min which served as a baseline. The study was conducted by outsourcing services (Taiwan Mouse Clinic).

Cardiovascular Function Test

The effects of morphine and Compound 67 on cardiovascular function were determined after mice are habituated to the chamber for 15 min. Blood pressure and pulse rate were measured in conscious mice by tail cuff plethysmography using a BP-2000 blood pressure analysis system. The rate-pressure product was calculated as the product of heart rate and systolic pressure. The study was conducted by outsourcing services (Taiwan Mouse Clinic).

Acetone Drop Test

In cancer-induced pain model, cold allodynia in mice was assessed by using the acetone test. Absolute acetone (100%) in a volume of 5 µL was placed on the base of the paw in mice. The duration of withdrawal in the 30 seconds immediately following acetone application to the surface of the hindpaws was measured to assess cold allodynia. See, e.g., Kukkar et al., Journal of the Formosan Medical Association, 2014, 113:921-928.

Conditioned Place Preference (CPP) Test

To examine the effects of Compound 67 on the reinstatement of morphine CPP, the available CPP apparatus (MED Associates, East Fairfield, Vt.) was used. The system consisted of an 18 cm×20 cm white chamber with a rough floor and an 18 cm×20 cm black chamber with a smooth floor. The mice were injected with equivalent volume of saline in the morphine and placed in the saline-paired side and were subcutaneously injected with and 10 mg/kg morphine every afternoon and placed in the pre-assigned morphine-paired side, with the chamber door closed for 30 minutes. In the post-conditioning day (expression test), the mice received no drug or saline and were placed in the side passage and allowed free access to the entire box for 15 minutes. For the extinction procedure, the animals were put in the side passage and given free access to the box for 30 minutes. After 15 days of extinction testing there was no evidence of extinction. Following extinction the mice were distributed equally to 3 groups be assigned in the low dose morphine (2.5 mg/kg)-induced reinstatement group, high dose morphine (5 mg/kg)-induced reinstatement group, or Compound 67 induced-reinstatement group. The mice in the drug-induced reinstatement group received treatment on reinstatement day (Day 21). See, e.g., Homji et al., International Journal of Clinical and Experimental Medicine, 2012, 5:105-123.

Statistical Analysis

All in vitro and in vivo studies were repeated multiple times to ensure the reliability of the individual values. The sample size used in all studies was based on previous experience. No samples, mice, or data points were excluded from the reported analysis. Investigators were blinded to the test conditions. In all studies, an individual administered drugs to the cells or animals, and another individual, who was blinded to the drug administeration, observed the response and analyzed the data. Data are presented as the mean±standard error of mean (SEM) (GraphPad Prism version 5.0, GraphPad Software, San Diego, Calif., USA). For the time-response curves, the two-way analysis of variance (ANOVA) with a Bonferroni's post-hoc test was used. For the quantitative results from the time-response curves, the Student's t-test or the one-way ANOVA with Newman-Keuls post-hoc tests was used. $p<0.05$ was considered statistically significant.

Example 69

Regulation of Opioid Receptor Signaling Pathways by Compound 67

Opioid receptors activate two directional G protein-coupled receptor (GPCR) signaling pathways: one is through second messengers such as cAMP which leads to a decrease of the cAMP level; and the other is via β-arrestin which leads to induction of receptor internalization.

A study was performed to evaluate the effect of Compound 67 on MOR- and NOP-mediated signaling pathways.

As MOR belongs to the GPCR family, activation of MOR leads to a decrease in intracellular cAMP level. The effect of Compound 67 on intracellular cAMP level was assessed to investigate whether Compound 67 was an agonist of MOR. The G protein coupling was measured by the inhibition of cAMP accumulation in human embryonic kidney 293 (HEK-293) cells constitutively expressing MOR (HEK-MOR). Cells were simultaneously treated with Compound 67, Met-5, and morphine; and the amount of intracellular cAMP was traced by luminescence intensity. Compound 67, Met-5, and morphine significantly decreased cAMP production in HEK-MOR cells in a dose-dependent manner.

It was observed that Compound 67 ($EC_{50}=0.63$ nM) unexpectedly exhibited G protein-coupling potency similar to Met-5 ($EC_{50}=0.38$ nM) but higher than morphine ($EC_{50}=3.7$ nM).

Opioid receptors have been reported to couple to G protein-independent β-arrestin-2-mediated pathways. See, e.g., Al-Hasani et al, Anesthesiology, 2011, 115:1363-1381. The potency of the above three molecules in a β-arrestin-2 recruitment assay (PathHunter), which was based on enzyme complementation in Chinese hamster ovary (CHO)-

K1 cells expressing human MOR (CHO-K1-MOR), was further examined. Compound 67, Met-5, and morphine all triggered β-arrestin-2 recruitment. Compound 67 induced more β-arrestin recruitment than that in morphine but induced less β-arrestin recruitment than Met-5. The $EC_{50}$ of Compound 67, Met-5, and morphine on β-arrestin recruitment, were determined to be 1.9 μM, 0.28 μM, and 1.6 μM, respectively, and Emax of Compound 67 was 3 fold higher than that of morphine.

Compound 67 was also studied to examine its effect on the G protein-coupled inwardly rectifying potassium (GIRK) channels, as this is another MOR G protein-dependent signaling pathway that contributes to opioid receptor-mediated analgesia. The pituitary cells (AtT-20 cell line) highly express the endogenous GIRK1/GIRK2 channel, which were transfected with a myc-MOR expression plasmid for preforming a potassium channel assay. See, e.g., Lee et al., Nucleic Acids Research, 2014, 42:13012-13025. It was observed that Compound 67 exhibited high GIRK channels activation efficacy with an $EC_{50}$ of 59.9 nM, higher than 140.6 nM exhibited by morphine. Also, Compound 67 and morphine both caused a MOR-dependent membrane potential hyperpolarization in myc-tagged MOR-expressing AtT-20 cells, and Compound 67 had an Emax slightly higher than that of morphine.

Moreover, MOR internalization was measured by a highly sensitive enzyme complementation assay in U2OS cells expressing human MOR (U2OS-MOR). It was observed that morphine exhibited minimal receptor internalization and, by contrast, Compound 67 caused significant internalization of the MOR in this assay, at a level approximately two-fold that of the maximal responses of morphine. The efficacy and potency of Compound 67 to trigger MOR internalization were both higher than those of morphine.

The results set forth above demonstrate that Compound 67 was a MOR agonist.

Compound 67 was studied as a NOP agonist to examine its effect on NOP-mediated intracellular cAMP content. It was measured using the PathHunter enzyme complementation assay in CHO-K1 cells expressing human NOP (CHO-K1-NOP). As orphanin FQ, Compound 67 induced more NOP-mediated cAMP inhibition in CHO-K1-NOP cells than that with morphine. The $EC_{50}$ of Compound 67 (2.2 nM) in decreasing the cAMP level was lower than that of morphine, and the Emax of Compound 67 was similar to orphanin FQ.

This result indicates that Compound 67 was also an NOP agonist.

In addition to the cAMP pathway, β-arrestin-2 recruitment assay was further performed to determine the effect of compound 67 on NOP. In CHO-K1-NOP cell, the $EC_{50}$ of Compound 67 was lower than that of orphanin FQ and the dose-response curve of Compound 67 was similar to morphine.

In sum, Compound 67 had G protein-coupling and GIRK channels activation potency similar to morphine and induced more MOR internalization and β-arrestin recruitment in human MOR expression cells than that with morphine. In addition, Compound 67 also induced significant NOP-mediated cAMP inhibition and β-arrestin-2 recruitment.

These results show that Compound 67 was a dual agonist for MOR and NOP.

Compound 67 Induced Antinociception in Mice

To investigate in vivo acute opioid pharmacology, thermal stimuli using tail-flick test and mechanical stimuli using tail-clip test were performed to evaluate the nociceptive effects of Compound 67 and morphine. Thermal nociception behavior of B6 mice was detected at the indicated time points (30, 60, 90, and 120 min) after a single dose subcutaneous injection. After detection of basal latencies, each mouse was injected with either morphine or Compound 67 to detect post-test latencies. The time-response curves were calculated and presented as percentage of MPE and AUC. Morphine induced antinociception at doses of 2.4-7.2 mg/kg (all P<0.001; two-way ANOVA). Quantitative results (AUC) showed significant differences between the vehicle control and morphine-treated mice (all P<0.001; one-way ANOVA). Compound 67 produced equi-antinociceptive effects at doses of 0.6-1.8 mg/kg (all P<0.001; two-way ANOVA). The time-response curves and AUC both showed significant differences between the vehicle control and Compound 67-treated mice (all P<0.001; one-way ANOVA). Maximum antinociception for both morphine and Compound 67 was sustained up to 30-60 min after the injection.

These results indicate that Compound 67 induced antinociception in mice.

A study was further carried out to determine whether Compound 67 induced antinociception was dependent on MOR activation. MOR knockout mice were subcutaneously injected with vehicle, 7.2 mg/kg morphine, or equi-antinociceptive dose of Compound 67. In MOR knockout mice model, there was no antinociception induced by morphine (all P>0.05; two-way ANOVA) or Compound 67 (all P>0.05; two-way ANOVA). Quantitative results (AUC) also revealed no significant differences between the vehicle control and morphine-treated groups or between vehicle control and Compound 67-treated groups (P>0.05; one-way ANOVA). Furthermore, both morphine and Compound 67 were evaluated on antinociception of mechanical pain in wildtype B6 mice in a tail clip test (P<0.001; one-way ANOVA). Unexpectedly, Compound 67 showed a higher antinociceptive effect with mechanical stimuli than morphine.

These results show that Compound 67 exhibited the antinociceptive effect in acute mechanical pain, dependent on MOR activation, better than that exhibited by morphine.

Tolerance and Cross-Tolerance Between Compound 67 and Morphine

A study was performed to investigate whether Compound 67 produced antinociceptive tolerance and whether there was cross-tolerance between Compound 67 and morphine.

With 5 days of twice-daily treatment, tail-flick tests were performed at 30 min after equianalgesic doses of Compound 67 and morphine. The time-response curves indicated that there were no significant differences between the Compound 67- and morphine-treated groups (treatment; P>0.05, day; P<0.001, interaction; P>0.05; two-way ANOVA).

These results indicate that both morphine and Compound 67 produced similar antinociceptive tolerance after subchronic treatment.

To investigate the cross-tolerance interaction between Compound 67 and morphine, mice tolerant with these molecules were separately challenged with vehicle, morphine, or compound 67 on day 6. The antinociceptive effects in Compound 67-tolerant mice were rescued after treatment with equianalgesic dose of morphine (7.2 mg/kg) (P<0.001; Student's t test) but not Compound 67. Compared with vehicle treatment, morphine-tolerant mice challenged with equianalgesic dose of Compound 67 (1.8 mg/kg) unexpectedly exhibited a significant increase in antinociceptive effects (P<0.001; Student's t test), which was not observed in mice treated with morphine.

Compared to the morphine-tolerant mice challenged with equi-analgesic dose of Compound 67, the Compound 67-tolerant mice challenged with equi-analgesic dose of morphine produced significantly lower antinociceptive efficacy (P<0.01; Student's t test).

These results indicate that there was asymmetric cross-tolerance between morphine and Compound 67.

Constipating Potency of Compound 67 in Mice

Constipatory effects of single subcutaneous injection of morphine and Compound 67 were assessed by charcoal meal and glass bead tests in mice. The GI inhibition potency of morphine and Compound 67 were investigated using a charcoal meal test. Both Compound 67 and morphine showed GI inhibition potency. The mice treated with morphine had an $ED_{50}$ of gastrointestinal transit inhibition, i.e., 1.8 mg/kg, significantly lower than that of antinociception, i.e., 2.4 mg/kg. By contrast, the mice treated with Compound 67 had an $ED_{50}$ of antinociception, i.e., 0.78 mg/kg, markedly lower than that of gastrointestinal transit inhibition, i.e., 1.6 mg/kg. The maximal antinociceptive effects of Compound 67 and morphine were similar (P>0.05; Student's t test) at their respective single high analgesic doses. Unexpectedly, administration of Compound 67 caused less gastrointestinal dysfunction than morphine at equianalgesic doses (P<0.05; Student's t test).

In addition, morphine and Compound 67 were investigated using the glass bead test in order to assess their effects on colon motility. Both Compound 67 and morphine increased the glass bead expulsion times compared to the vehicle group (P<0.001; one-way ANOVA). However, the bead expulsion time of Compound 67 group was significantly shorter than the morphine-treated group. Thus, use of Compound 67 as an analgesic produced antinociception, while exerting less constipation than morphine.

Effects of Compound 67 on Respiratory and Cardiovascular Dysfunction

Opioids have been shown to regulate both cardiovascular and respiratory function. See, e.g., Feng et al., Current Drug Targets, 2012, 13:230-246. A study was performed to examine the acute effects of analgesic, respiratory and cardiac regulation by treating with equi-antinociceptive doses of morphine or Compound 67 in B6 mice. Baseline was detected before treatment. Mice treated with morphine or Compound 67 then underwent 10 min to 60 min recording. After acute injection, analgesic effects were exerted by either morphine at 20 min (one-way ANOVA) or Compound 67 at 10 min (P<0.05; one-way ANOVA), which sustained until 60 min at last.

All mice treated with morphine or Compound 67 induced respiratory frequency depression after 10 min (P<0.05; one-way ANOVA). Notably, morphine also significantly reduced respiratory amplitude (tidal volume) at 10 to 20 min (P<0.05; one-way ANOVA) but not Compound 67 (P>0.05; one-way ANOVA). Unexpectedly, the mice treated with morphine exhibited marked respiratory depression at 10 min and keep falling of respiratory frequency going through 60 min and, by contrast, the mice treated with Compound 67 kept recovery of respiratory frequency after 30 min. This result indicates that Compound 67 demonstrated an early return of lung function.

Although there was non-significant effect on blood pressure in mice treated with morphine (P>0.05; one-way ANOVA), pulse (heart rate) and rate-pressure product (heart rate×systolic blood pressure) were downregulated (P<0.05; one-way ANOVA). The morphine-treated mice showed that the heart rate was reduced from 10 to 30 min and the rate-pressure product was reduced from 10 to 20 min. By contrast, Compound 67-treated mice demonstrated a minimal effect on cardiovascular function (systolic blood pressure: P>0.05, one-way ANOVA; pulse: P<0.05, one-way ANOVA; rate pressure product: P<0.05, one-way ANOVA).

These result showed that the onset time of Compound 67 in analgesia was shorter than morphine. In addition, morphine-treated mice exhibited marked contractile dysfunction after acute injection, whereas Compound 67-treated mice showed less respiratory depression and cardiovascular dysfunction than morphine.

Anti-Nociception Efficacy of Compound 67 in Mice in Neuropathic and Cancer Pain Models An oxaliplatin-induced neuropathic pain model was used to investigate antinociceptive effect of Compound 67. In this neuropathic pain model, mechanical allodynia attach to maximal hyposensitive on 3 to 5 days after oxaliplantin single injection. See, e.g., Nassini et al., PAIN, 2011, 152: 1621-1631. The mechanical thresholds of oxaliplatin-injected mice were measured using the Von Frey test to examine the antinociceptive effects of each treatment and were significantly decreased on postinoculation day 3 (PID 3) as compared to sham-treated mice (P<0.05; Student's t test). This treatment paradigm was followed to produce neuropathic pain mice.

These mice were injected with vehicle, Compound 67, or morphine on PID 3 with the equi-antinociceptive doses. Compared to vehicle group, both the Compound 67- and morphine-treated mice exerted similar antinociceptive effects at 30 min after treatment (P>0.05; Student's t test). The antinociceptive effect of Compound 67 was comparable to that of morphine in oxaliplatin-induced sensory allodynia.

Compound 67 was also examined on its antinociception in a skin cancer pain model. Sensory allodynia almost went through maximal state in 2 weeks after intraplantar implantation of melanoma cells in mice. The threshold of mechanical allodynia in melanoma cell-implanted foot was significantly decreased on PID 18 as compared to sham-treated mice (P<0.05; Student's t test).

The cold allodynia was tested using acetone drop test and mechanical allodynia was measured using the Von Frey test to examine the antinociceptive effects of each drug treatment. Mice were injected with equi-antinociceptive doses of Compound 67 or morphine. In acetone drop test, the licking and shaking frequency of Compound 67-treated group was less than that of morphine at 30 min after treatment in melanoma cell-implanted mice on PID18 (P<0.05; one-way ANOVA). In Von Frey test, the withdrawal threshold of Compound 67-treated group was greater than that of morphine at 30 min after treatment in melanoma cell-implanted mice on PID19 (P<0.05; one-way ANOVA). Both Compound 67 and morphine exerted antinociceptive effects on PID 19, after twice daily injection, the antinociceptive effect of Compound 67 was more than that of morphine at 30 min on PID 21 and PID 23.

These results suggest that Compound 67 produced antinociceptive effect of mechanical comparable to morphine in a model of chemotherapy drug induced neuropathic pain. In addition, Compound 67 produced a better antinociceptive effect of mechanical and cold allodynia than morphine in the cancer induced pain model.

Antinociceptive and Gastrointestinal Mobility Effects of Compound 67 Related to NOP Signaling Pathway As described above, Compound 67 demonstrated marked potency in modulating both MOR and NOP. To determine whether Compound 67-mediated antinociception and gastrointestinal mobility was related to NOP, the activity of Compound 67 was examined by pretreatment with a NOP specific antagonist, i.e., BANORL24, by using the tail-flick test and tail-clip test for antinociceptive test, and using the charcoal meal test for gastrointestinal inhibition. 30 Minutes-pretreatment with BANORL24 did not inhibit Compound 67-induced antinociception during the beginning 30 min. Yet, a significant difference was observed from 60 to 120 min post-injection between the Compound 67-treated group and the Compound 67 plus BANORL24-treated group (all P<0.001; two-way ANOVA). Notably, Compound 67 induced antinociception of mechanical pain was not inhibited by BANORL24 in the tail-clip test (P<0.01; one-way ANOVA).

Furthermore, to determine whether Compound 67-mediated gastrointestinal inhibition was dependent on NOP activation, wildtype B6 mice were pretreated with either the vehicle or BANORL24 (10 mg/kg, iv.) at 30 min before the injection of Compound 67 (1.8 mg/kg). The charcoal meal test was performed after 30 or 90 min. It was observed that BANORL24 did not attenuate Compound 67-mediated gastrointestinal dysfunction, but enhanced Compound 67-mediated gastrointestinal inhibition after 90 min (P<0.001; one-way ANOVA).

These results suggest that Compound 67 induced long-term thermal antinociception related to NOP activation.

Effect of Compound 67 on Reinstatement of Morphine CPP

Morphine conditioned mice showed a place preference during the expression test, and the place preference was attenuated by repeated extinction testing. Significant difference was observed between extinction test and reinstatement in morphine-challenged groups, but not in Compound 67-challenged group (P<0.001; one-way ANOVA). In addition, this study also showed significant difference between Compound 67- and morphine-challenged groups (P<0.001; one-way ANOVA). It revealed that morphine, not Compound 67, induced reinstatement of morphine CPP.

These results demonstrate that administration of Compound 67 attenuates opioid addiction-related behaviors.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of formula (I) below or a pharmaceutically acceptable salt thereof:

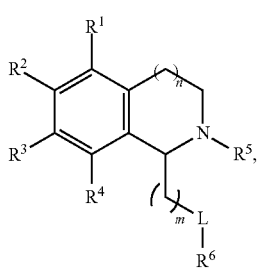

(I)

wherein each of $R^1$-$R^4$, independently, is H;

$R^5$ is H;

$R^6$ is

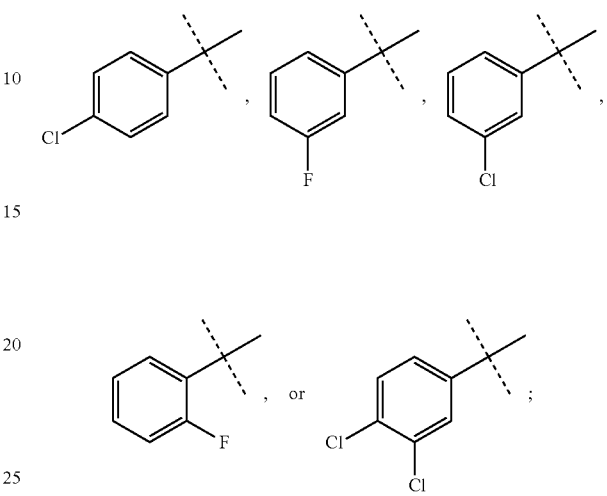

L is NHC(O)—;

m is 1; and n is 1.

2. The compound of claim 1 or a pharmaceutically acceptable salt thereof, wherein the ring carbon attached to both the phenyl ring and the ring nitrogen atom has a stereoisomeric configuration of R or S, and the compound has an enantiomeric excess of 90% or higher.

3. A compound of formula (I) below or a pharmaceutically acceptable salt thereof,

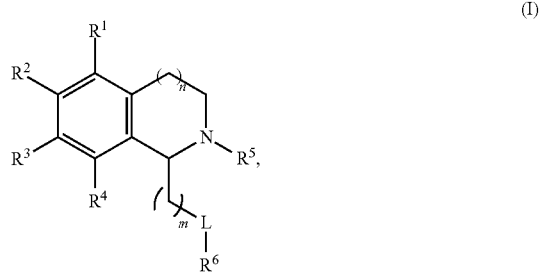

(I)

wherein each of $R^1$-$R^4$, independently, is H;

$R^5$ is —S(O)$_2$R, in which R is $C_{6-14}$ aryl that is either unsubstituted, or mono-, di-, or tri-substituted with halo, $CF_3$, OMe, $OCF_3$, or $C_{1-6}$ alkyl;

$R^6$ is unsubstituted $C_{6-14}$ aryl;

L is —NHC(O)—;

m is 1; and n is 1.

4. The compound of claim 3 or a pharmaceutically acceptable salt thereof, wherein the compound is Compound 24 shown below:

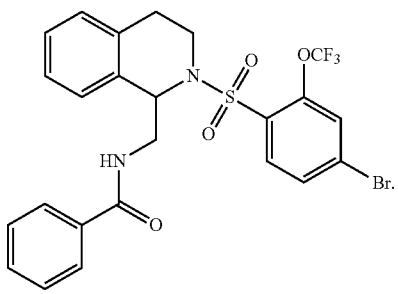

24

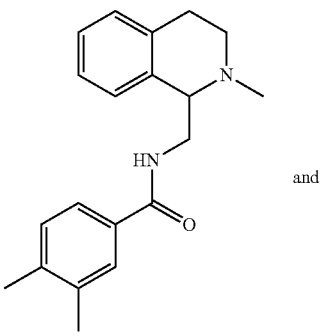

5

5. A pharmaceutical composition for treating an opioid receptor-associated condition, the pharmaceutical composition comprising a compound of claim 1 or a pharmaceutically acceptable salt thereof and a pharmaceutically acceptable carrier.

6. A compound of formula (I) below or a pharmaceutically acceptable salt thereof,

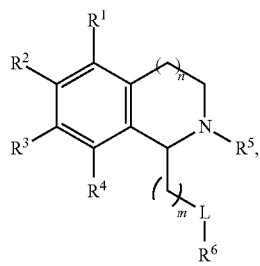

(I)

wherein each of $R^1$-$R^4$, independently, is H;

$R^5$ is $C_{1-6}$ alkyl that is either unsubstituted or substituted with Cl;

$R^6$ is $C_{6-14}$ aryl mono-, di-, or tri-substituted with halo or $C_{1-6}$ alkyl;

L is —NHC(O)—;

m is 1; and n is 1.

7. The compound of claim 6 or a pharmaceutically acceptable salt thereof, wherein the compound is one of Compounds 65-67, the structures of which are shown below:

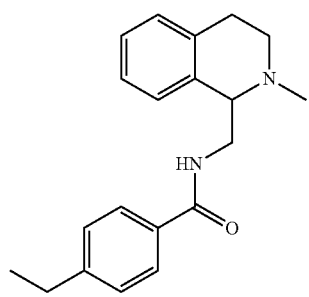

65

-continued

66 and

67

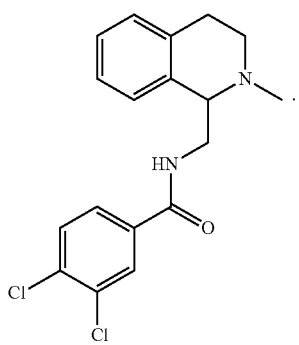

8. The compound of claim 6 or a pharmaceutically acceptable salt thereof, wherein the compound is one of Compounds 61-64, the structures of which are shown below:

61

62

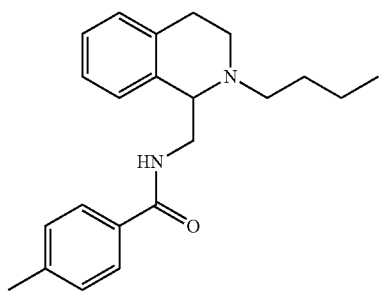

63
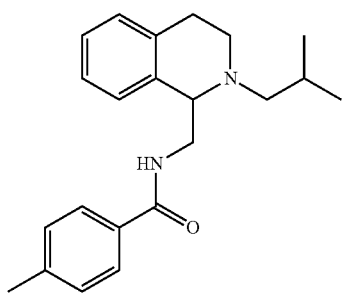
and
64
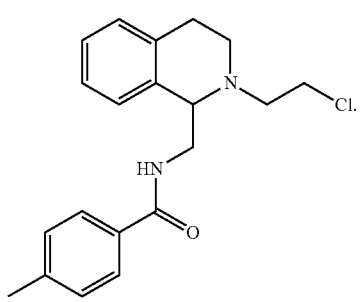
9. A compound or a pharmaceutically acceptable salt thereof, wherein the compound is one of Compounds 47 and 49-60 shown below and the ring carbon attached to both the phenyl ring and the ring nitrogen atom has a stereoisomeric configuration of R or S, and the compound has an enantiomeric excess of 90% or higher:
47
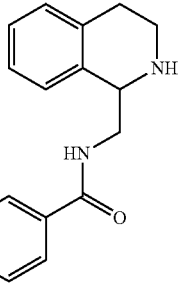
49
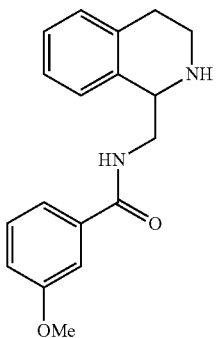
50
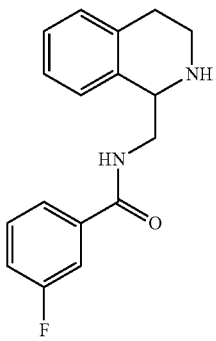
51
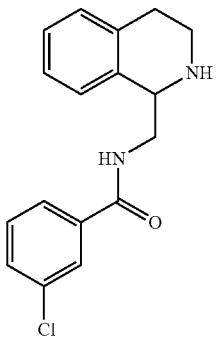
52
53
54
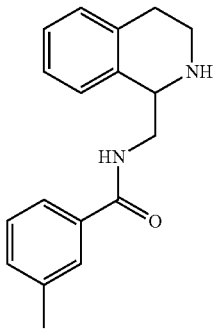

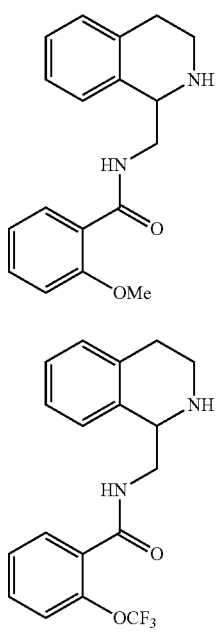
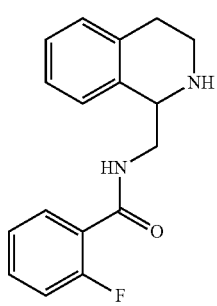
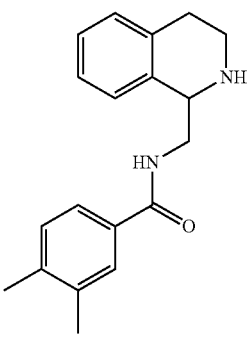
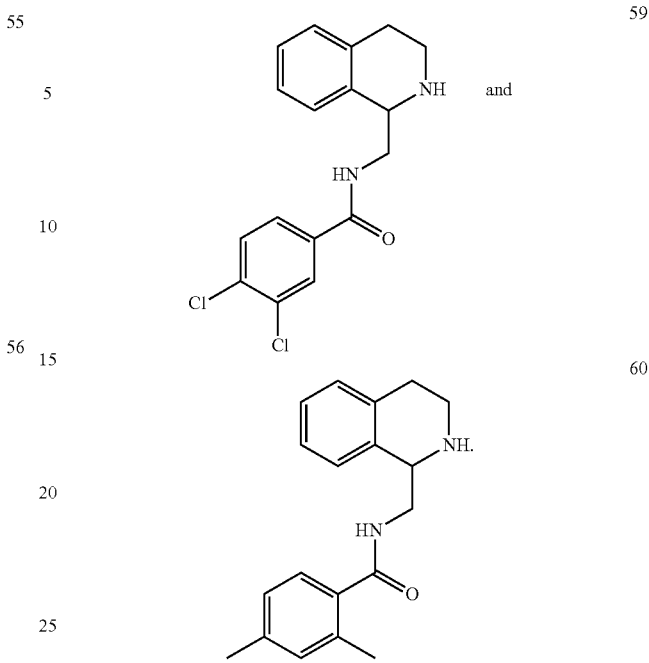

10. The compound of claim 6 or a pharmaceutically acceptable salt thereof, wherein the ring carbon attached to both the phenyl ring and the ring nitrogen atom has a stereoisomeric configuration of R or S, and the compound has an enantiomeric excess of 90% or higher.

11. The compound of claim 7 or a pharmaceutically acceptable salt thereof, wherein the ring carbon attached to both the phenyl ring and the ring nitrogen atom has a stereoisomeric configuration of R or S, and the compound has an enantiomeric excess of 90% or higher.

12. The compound of claim 8 or a pharmaceutically acceptable salt thereof, wherein the ring carbon attached to both the phenyl ring and the ring nitrogen atom has a stereoisomeric configuration of R or S, and the compound has an enantiomeric excess of 90% or higher.

13. A pharmaceutical composition for treating an opioid receptor-associated condition, the pharmaceutical composition comprising a compound of claim 6 or a pharmaceutically acceptable salt thereof and a pharmaceutically acceptable carrier.

14. A pharmaceutical composition for treating an opioid receptor-associated condition, the pharmaceutical composition comprising a compound of claim 7 or a pharmaceutically acceptable salt thereof and a pharmaceutically acceptable carrier.

15. A pharmaceutical composition for treating an opioid receptor-associated condition, the pharmaceutical composition comprising a compound of claim 8 or a pharmaceutically acceptable salt thereof and a pharmaceutically acceptable carrier.

\* \* \* \* \*